United States Patent
Stumpp et al.

(10) Patent No.: US 7,417,130 B2
(45) Date of Patent: Aug. 26, 2008

(54) COLLECTION OF REPEAT PROTEINS COMPRISING REPEAT MODULES

(75) Inventors: Michael Tobias Stumpp, Zürich (CH); Patrick Forrer, Zürich (CH); Hans Kaspar Binz, Zürich (CH); Andreas Plückthun, Zürich (CH)

(73) Assignee: University of Zurich, Zurich (CH)

( * ) Notice: Subject to any disclaimer, the term of this patent is extended or adjusted under 35 U.S.C. 154(b) by 666 days.

(21) Appl. No.: 10/363,552

(22) PCT Filed: Sep. 10, 2001

(86) PCT No.: PCT/EP01/10454

§ 371 (c)(1), (2), (4) Date: Jul. 6, 2003

(87) PCT Pub. No.: WO02/20565

PCT Pub. Date: Mar. 14, 2002

(65) Prior Publication Data

US 2004/0132028 A1    Jul. 8, 2004

(30) Foreign Application Priority Data

Sep. 8, 2000 (EP) .................................. 00119670

(51) Int. Cl.
*C07H 21/04* (2006.01)
*C07H 21/02* (2006.01)
*C12N 15/11* (2006.01)

(52) U.S. Cl. ..................................... 536/23.1; 435/91.1
(58) Field of Classification Search .................. None
See application file for complete search history.

(56) References Cited

FOREIGN PATENT DOCUMENTS

| WO | WO96/06166 | 2/1996 |
| WO | WO98/06845 | 2/1998 |
| WO | WO/00/34784 | 6/2000 |
| WO | WO01/61005 | 8/2001 |
| WO | WO01/85909 | 11/2001 |

OTHER PUBLICATIONS

Bork, Proteins: Structure, Function, and Genetics 17: 363 (1993).*
Kajava, J. Mol. Biol. 277: 519-527 (1998).
Kobe et al., Nature 374(9): 183-186 (1995).
Lehmann et al., Protein Eng. 13(1): 49-57 (2000) (Abstract PMID 10679530).
Lehmann et al., Protein Eng. 15(5): 403-4011 (2002) (Abstract PMID 12034860).
Nygren et al., Current Opinion in Structural Biology 7: 463-469 (1997).
Sedgwick et al., TIBS 24(8): 311-316 (1999).
Zhang et al., J. Mol. Biol. 299: 1121-1132 (2000).
Russ, William P. et al., "Knowledge-based potential functions in protein design", Current Opinion in Structural Biology, 2002, 12:447-452, Elsevier Science, New York, NY, USA.
Forrer, Patrik et al., "A novel strategy to design binding molecules harnessing the modular nature of repeat proteins", FEBS Letters 539 (2003) 2-6, Elsevier Science B.V., New York, NY, USA.
Groves, Matthew R. et al., "Topological characteristics of helical repeat proteins", Current Opinion in Structural Biology 1999, 9:383-389, Elsevier Science Ltd., New York, NY, USA.
Kobe, Bostjan et al., "The leucine-rich repeat: a versatile binding motif", TIBS 19, Oct. 1994, p. 415, abstract, Elsevier Science, New York, NY, USA.

* cited by examiner

*Primary Examiner*—James Martinell
(74) *Attorney, Agent, or Firm*—Arent Fox

(57) ABSTRACT

The present invention relates to collections of repeat proteins comprising repeat modules which are derived from one or more repeat units of a family of naturally occurring repeat proteins, to collections of nucleic acid molecules encoding said repeat proteins, to methods for the constructions and application of such collections and to individual members of such collections.

16 Claims, 53 Drawing Sheets

Figure 1
Repeat Protein
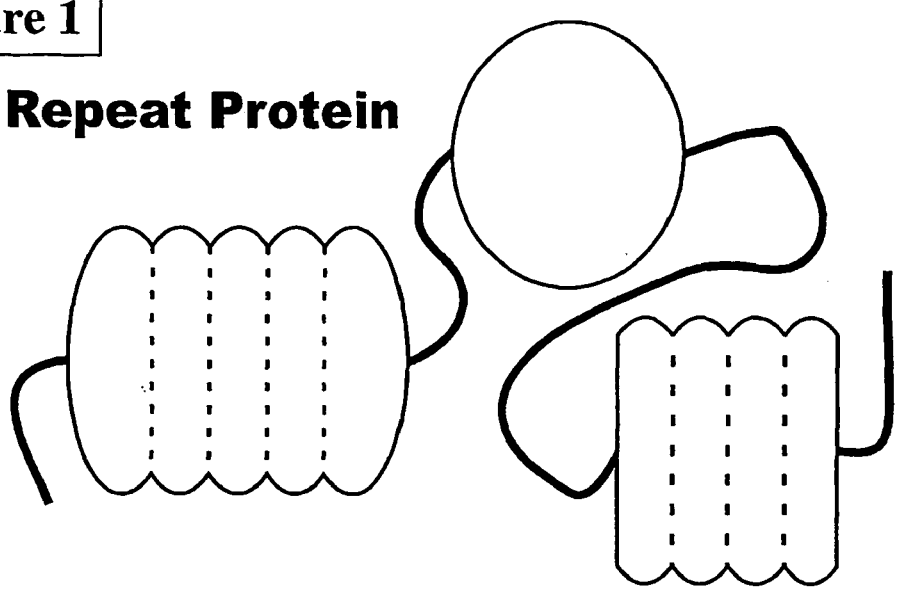
Repeat Domains
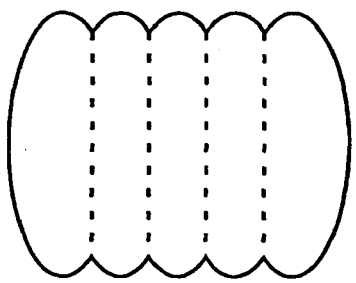
Non-repeat Domain
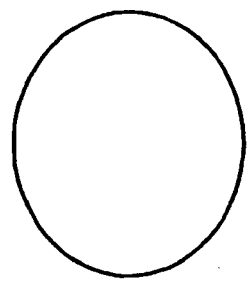
Repeat Module
Capping Modules
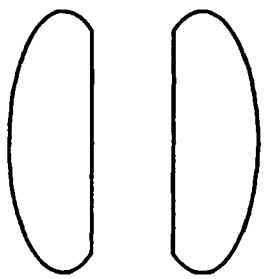
Linker

Figure 2B:
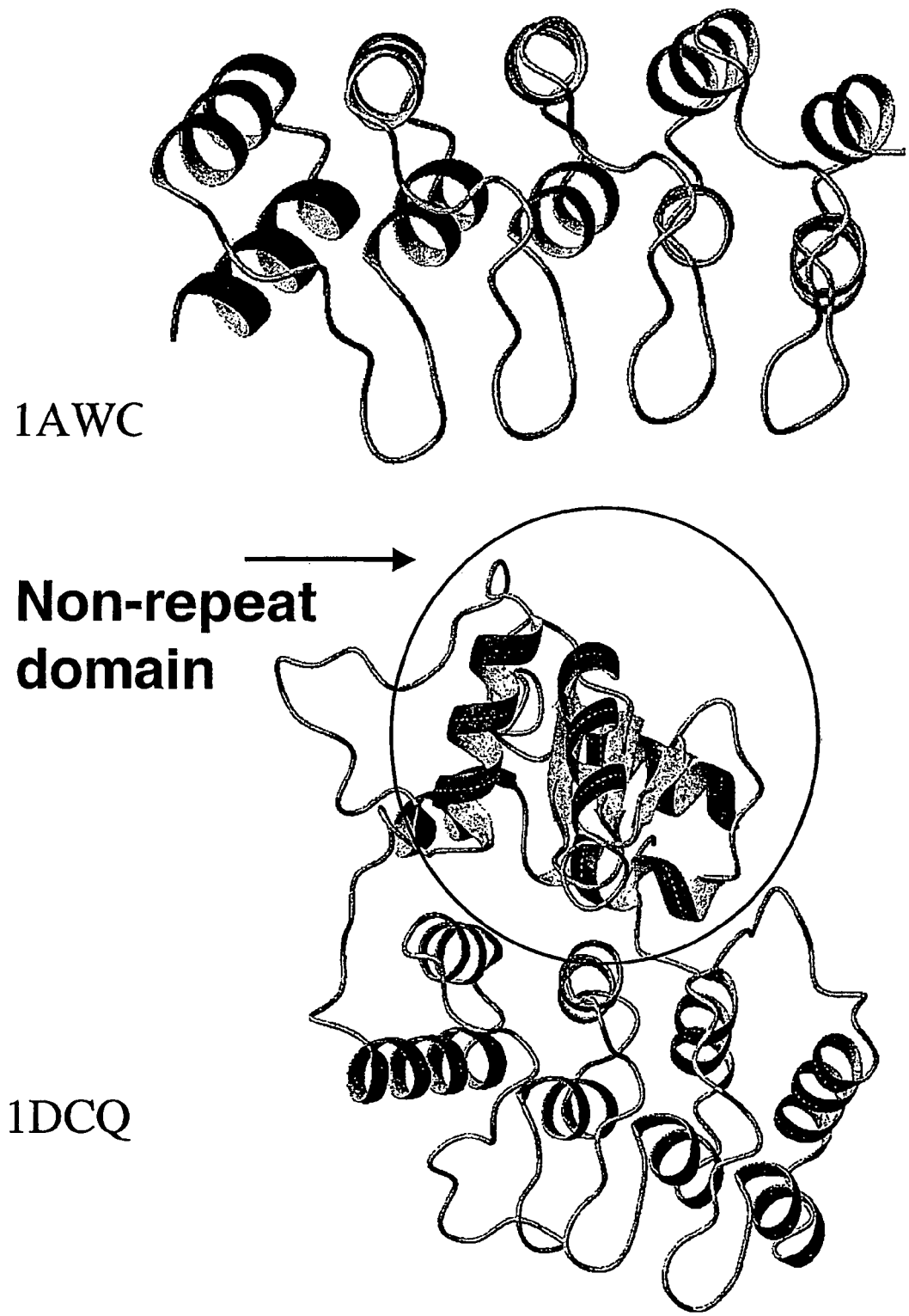

Figure 2a
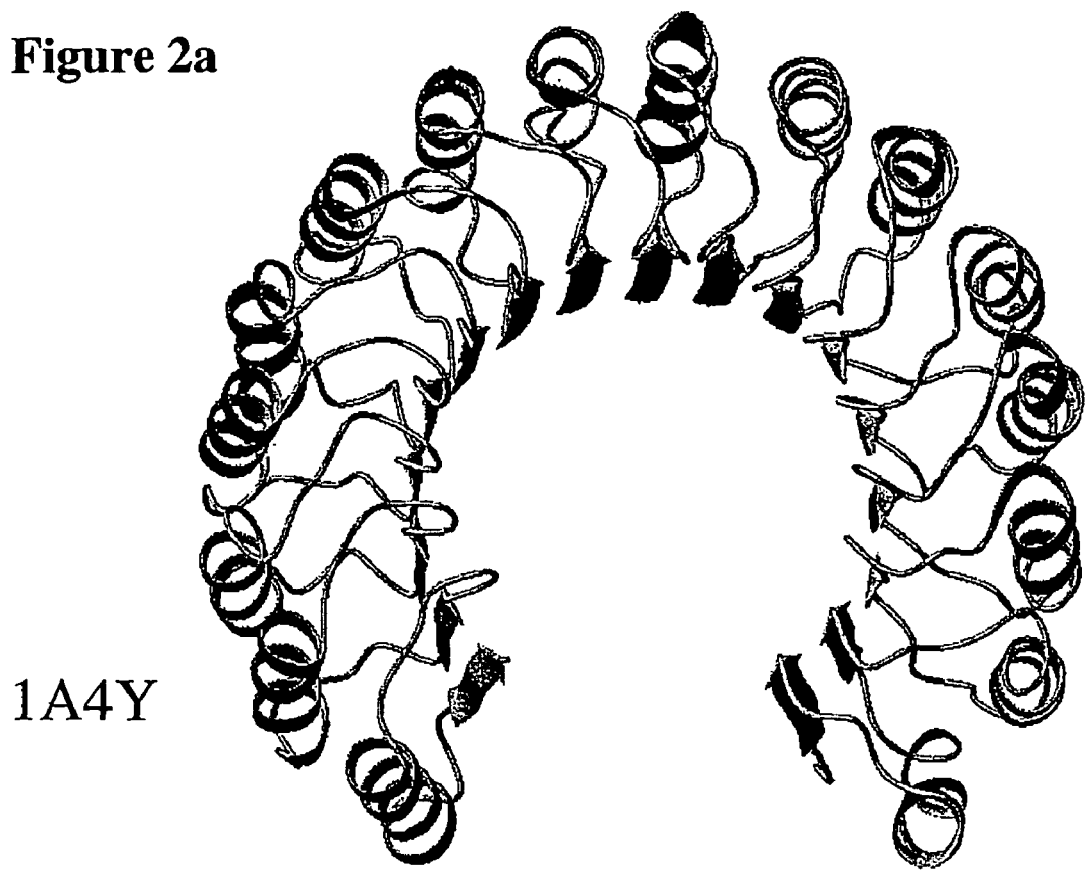
1A4Y
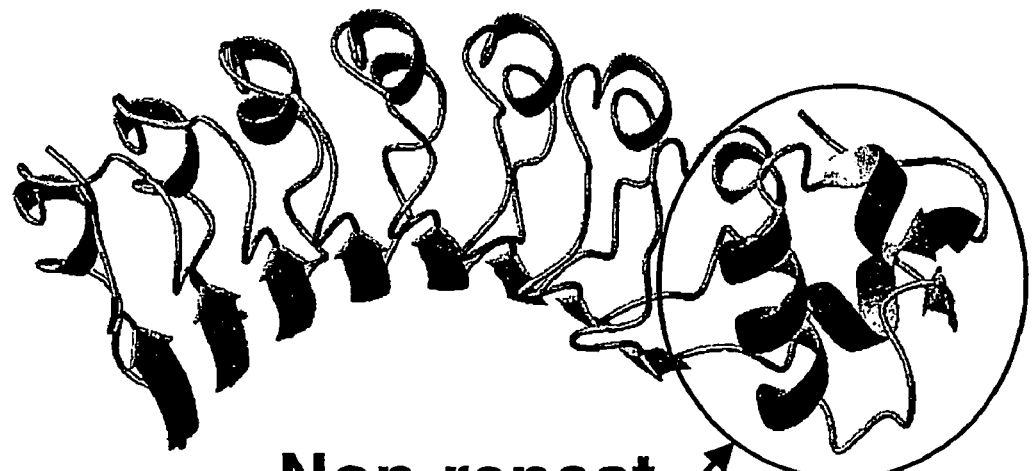
1D0B     Non-repeat domain

Figure 5a

Figure 5c human RI (P13489)
N-terminal

| | 1 | | | | 5 | | | | | 10 | | | | | 15 | | | | | 20 | | | | | 25 | | | |
|---|---|---|---|---|---|---|---|---|---|---|---|---|---|---|---|---|---|---|---|---|---|---|---|---|---|---|---|---|
| 1 | | Q | V | V | R | L | D | D | C | G | L | T | E | A | R | C | K | D | I | S | S | A | L | R | V | N | P |
| 2 | K | I | Q | K | L | S | L | Q | N | C | C | L | T | G | A | G | C | G | V | L | S | S | T | L | R | T | L | P |
| 3 | R | L | E | K | L | Q | L | E | Y | C | S | L | S | A | A | S | C | E | P | L | A | S | V | L | R | A | K | P |
| 4 | Q | L | E | A | L | K | L | E | S | C | G | V | T | S | D | N | C | R | D | L | C | G | I | V | A | S | K | A |
| 5 | R | L | R | T | L | W | I | W | E | C | G | I | T | A | K | G | C | G | D | L | C | R | V | L | R | A | K | E |
| 6 | Q | L | E | S | L | W | V | K | S | C | S | F | T | A | A | C | C | S | H | F | S | S | V | L | A | Q | N | R |
| 7 | V | L | R | V | L | W | L | A | D | C | D | V | S | D | S | S | C | S | S | L | A | A | T | L | L | A | N | H |

C-terminal L L E Q L V L Y D I Y W S E M E D R L Q A L E K D K P proportion 0.83 0.43 0.86 0.43 0.71 1.00 0.43 0.43 0.71 0.43 0.57 1.00 0.43 0.71 0.43 0.57 0.43 0.86 0.57 0.43 0.57 0.43
residue L E L W L C G L T A A C D L S S V L R A N P pig RI (P10775)
N-terminal

| | 1 | | | | 5 | | | | | 10 | | | | | 15 | | | | | 20 | | | | | 25 | | | |
|---|---|---|---|---|---|---|---|---|---|---|---|---|---|---|---|---|---|---|---|---|---|---|---|---|---|---|---|---|
| 1 | | E | V | V | R | L | D | D | C | G | L | T | E | H | C | K | D | I | G | S | A | L | R | A | N | P | |
| 2 | K | I | Q | K | L | S | L | Q | N | C | S | L | T | E | A | G | C | G | V | L | P | S | T | L | R | S | L | P |
| 3 | H | L | E | K | L | Q | L | E | Y | C | R | L | T | A | A | S | C | E | P | L | A | S | V | L | R | A | T | R |
| 4 | Q | L | E | T | L | R | L | E | N | C | G | L | T | P | A | N | C | K | D | L | C | G | I | V | A | S | Q | A |
| 5 | R | L | K | T | L | W | L | W | E | C | D | I | T | A | S | G | C | R | D | L | C | R | V | L | Q | A | K | E |
| 6 | Q | L | E | S | L | W | V | K | S | C | S | L | T | A | A | C | C | Q | H | V | S | L | M | L | T | Q | N | K |
| 7 | T | L | R | V | L | C | L | G | D | C | E | V | T | N | S | G | C | S | S | L | A | L | L | L | A | N | R | |

C-terminal A L E Q L V L Y D T Y W T E V E D R L Q A L E G S K P proportion 0.83 0.57 0.86 0.86 1.00 0.71 1.00 0.43 0.57 0.43 1.00 0.71 0.57 0.86 0.43 0.57 0.43
residue L E L L C L T A A G C L S L R A N rat RI (P29315)
N-terminal

| | 1 | | | | 5 | | | | | 10 | | | | | 15 | | | | | 20 | | | | | 25 | | | |
|---|---|---|---|---|---|---|---|---|---|---|---|---|---|---|---|---|---|---|---|---|---|---|---|---|---|---|---|---|
| 1 | | Q | V | V | R | L | D | D | C | G | L | T | E | V | R | C | K | D | I | R | S | A | I | Q | A | N | P | |
| 2 | K | I | Q | K | L | S | L | Q | N | C | S | L | T | E | A | G | C | G | V | L | P | D | V | L | R | S | L | S |
| 3 | R | L | E | K | L | Q | L | E | Y | C | N | L | T | A | T | S | C | E | P | L | A | S | V | L | R | V | K | P |
| 4 | Q | L | E | S | L | A | N | C | G | I | T | S | A | N | C | K | D | L | C | D | V | V | A | S | K | A | | |
| 5 | R | L | R | T | L | W | L | W | D | C | D | V | T | A | E | G | C | K | D | L | C | R | V | L | R | A | K | Q |
| 6 | Q | L | E | S | L | W | V | K | T | C | S | L | T | A | A | S | C | P | H | F | C | S | V | L | T | K | N | S |
| 7 | V | L | R | V | L | W | L | G | D | C | D | V | T | D | S | G | C | S | S | L | A | T | V | L | L | A | N | R |

C-terminal I L Q Q L V L Y D I Y W T D E V E · D Q L R A L E E R P proportion 0.83 0.43 0.86 0.86 0.43 1.00 0.57 1.00 0.43 0.43 0.43 1.00 0.43 0.43 0.71 0.43 0.43 0.86 0.71 0.43 0.43 0.43
residue L E L L D C L T A A G C K D L C S V L R A N or K mouse RI (AAE58859)
N-terminal

| | 1 | | | | 5 | | | | | 10 | | | | | 15 | | | | | 20 | | | | | 25 | | | |
|---|---|---|---|---|---|---|---|---|---|---|---|---|---|---|---|---|---|---|---|---|---|---|---|---|---|---|---|---|
| 1 | | E | V | V | R | L | D | D | C | G | L | T | E | V | R | C | K | D | I | S | S | A | V | Q | A | N | P | |
| 2 | K | I | Q | K | L | S | L | Q | N | C | G | L | T | E | A | G | C | G | I | L | P | G | M | L | R | S | L | S |
| 3 | R | L | E | K | L | Q | L | E | Y | C | N | L | T | A | T | S | C | E | P | L | A | S | V | L | R | V | K | A |
| 4 | Q | L | E | S | L | K | L | E | N | C | G | I | T | A | A | N | C | K | D | L | C | D | V | V | A | S | K | A |
| 5 | K | L | G | T | L | W | L | W | E | C | D | I | T | A | E | G | C | K | D | L | C | R | V | L | R | A | N | Q |
| 6 | Q | L | E | S | L | W | I | K | T | C | S | L | T | A | A | S | C | P | Y | F | C | S | V | L | T | K | S | R |
| 7 | V | L | R | E | L | W | L | G | D | C | D | V | T | N | S | G | C | S | S | L | A | N | V | L | L | A | N | R |

C-terminal T L Q Q L V L Y D I Y W T N E V E E Q L R A L E E G R P proportion 0.83 0.57 0.86 0.43 0.86 1.00 0.43 0.57 1.00 0.57 0.43 0.43 1.00 0.43 0.43 0.71 0.43 0.43 0.71 0.71 0.43 0.43 0.43
residue L E L W L C G L T A A G C K D L C S V L R A N all RI  0.46 0.83 0.50 0.29 0.86 0.39 0.82 0.29 0.32 1.00 0.36 0.57 0.93 0.46 0.50 0.39 1.00 0.32 0.43 0.71 0.36 0.50 0.57 0.79 0.46 0.46 0.43 0.29
50%- L E - L - L - - C - L T - A - C - - L - S V L - - -
40% pos. L E - L - L - - C - L T A A - C - D L - S V L R A N -
30% pos. L E - L W L - D C G L T A A G C K D L C S V L R A N -
25% pos. L E K L W L E D C G L T A A G C K D L C S V L R A N P
module R L E  1 L  1 L  1  1  2 D L T E A G  4 K D L A S V L R S N P
           2        5       7         10   12             17    20         24

Figure 5d human RI (P13489)

N-terminal: D I Q S L D I Q C E E L S D A R W A E L L P L L Q Q C

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|
| 1 | A | L | A | E | N | L | R | S | N | E | L | G | D | V | G | V | H | C | V | L | Q | G | L | Q | T | P | S | C |
| 2 | T | L | Q | E | L | H | L | S | D | N | L | L | G | D | A | G | L | Q | L | L | C | E | G | L | L | D | P | Q | C |
| 3 | D | F | K | E | L | T | V | S | N | N | D | I | N | E | A | G | V | R | V | L | C | Q | G | L | K | D | S | P | C |
| 4 | S | L | R | E | L | A | L | G | S | N | K | L | G | D | V | G | M | A | E | L | C | P | G | L | L | H | P | S | S |
| 5 | S | L | K | E | L | S | L | A | G | N | E | L | G | D | E | G | A | R | L | L | C | E | T | L | L | E | P | G | C |
| 6 | F | L | L | E | L | Q | I | S | N | N | R | L | E | D | A | G | V | R | B | L | C | Q | G | L | G | Q | P | G | S |
| 7 | S | L | R | E | L | D | L | S | N | N | C | L | G | D | A | G | I | L | Q | L | V | E | S | V | R | Q | P | G | C |

C-terminal: S L R V I S proportion: 0.43 0.86    1.00 1.00    0.71 0.57 0.43 1.00    0.86 0.71 0.86 0.57 1.00 0.43 0.43    0.86 0.71 0.43 0.71 0.86 0.43    0.86 0.43 0.71
residue: S L    E L    L S N N    L G D A G V R    L C E or G L L    P G C pig RI (P10775)

N-terminal: M N L D I H C E Q L S D A R W T E L L P L L Q Q Y

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|
| 1 | S | L | T | E | L | C | L | R | T | N | E | L | G | D | A | G | V | H | L | V | L | Q | G | L | Q | S | P | T | C |
| 2 | T | L | R | E | L | H | L | S | D | N | P | L | G | D | A | G | L | R | L | L | C | E | G | L | L | D | P | Q | C |
| 3 | A | L | K | E | L | T | V | S | N | N | D | I | G | E | A | G | A | R | V | L | G | Q | G | L | A | D | S | A | C |
| 4 | S | L | R | E | L | D | L | G | S | N | G | L | G | D | A | G | I | A | E | L | C | P | G | L | L | S | P | A | S |
| 5 | T | L | K | E | L | S | L | A | G | N | K | L | G | D | E | G | A | R | L | L | C | E | S | L | L | Q | P | G | C |
| 6 | H | L | L | E | L | Q | L | S | S | N | K | L | G | D | S | G | I | Q | E | L | C | Q | A | L | S | Q | P | G | T |
| 7 | S | L | R | E | L | D | L | S | N | N | C | V | G | D | P | G | V | L | Q | L | L | G | S | L | E | Q | P | G | C |

C-terminal: G L R V I S proportion: 0.43 1.00 0.43 1.00 1.00    0.86 0.57    1.00    0.71 1.00 0.86 0.57 1.00 1.00 0.43 0.43 0.86 0.57 0.43 0.57 1.00 0.43 0.43 0.86 0.43 0.71
residue: S L R E L    L S    N    L G D A G a R L L C Q G L L Q P G C rat RI (P29315)

N-terminal: M S L D I Q C E Q L S D A R W T E L L P L I Q Q Y

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|
| 1 | A | L | T | E | L | S | L | R | T | N | E | L | G | D | A | G | V | H | L | V | L | Q | G | L | Q | N | P | T | C |
| 2 | T | L | R | E | L | H | L | N | D | N | P | L | G | D | E | G | L | K | L | L | C | E | G | L | R | D | P | Q | C |
| 3 | D | F | K | E | L | V | L | S | N | N | D | F | H | E | A | G | I | H | T | L | C | Q | G | L | K | D | S | A | C |
| 4 | S | L | Q | E | L | D | L | G | S | N | K | L | G | N | T | G | I | A | A | L | C | S | G | L | L | L | P | S | C |
| 5 | S | L | K | E | L | S | L | A | G | N | E | L | K | D | E | G | A | Q | L | L | C | E | S | L | L | E | P | G | C |
| 6 | S | L | F | E | L | Q | M | S | S | N | P | L | G | D | S | G | V | V | E | L | C | K | A | L | G | Y | P | D | T |
| 7 | S | L | R | E | L | D | L | S | N | N | C | M | G | D | N | G | V | L | Q | L | L | E | S | L | K | Q | P | S | C |

C-terminal: S L R I I S proportion: 0.57 0.86    1.00 1.00    0.86 0.43    1.00    0.71 0.71 0.71    1.00 1.00    0.43 0.86 0.71 0.43 0.57 1.00    0.86    0.86
residue: S L    E L    L S    N    L G D    G a    L L C E G L    P    C mouse RI (AAK68859)

N-terminal: M S L D I Q C E Q L G D A R W T E L L P L I Q Q Y

|   | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|
| 1 | A | L | T | E | L | S | L | R | T | N | E | L | G | D | G | G | A | G | L | V | L | Q | G | L | Q | N | P | T | C |
| 2 | T | L | R | E | L | H | L | N | D | N | P | M | G | D | A | G | L | K | L | L | C | E | G | L | R | D | P | Q | C |
| 3 | D | F | K | E | L | V | L | S | N | N | D | L | H | E | P | G | V | R | I | L | C | Q | G | L | K | D | S | A | C |
| 4 | S | L | Q | E | L | D | L | S | S | N | K | L | G | N | A | G | I | A | A | L | C | P | G | L | L | L | P | S | C |
| 5 | S | L | K | E | L | S | L | A | S | N | E | L | K | D | E | G | A | R | L | L | C | E | S | L | L | E | P | X | C |
| 6 | S | L | L | E | L | Q | M | S | S | N | P | L | G | D | E | G | V | Q | E | L | C | K | A | L | S | Q | P | D | T |
| 7 | S | L | R | E | L | D | L | S | N | N | C | M | G | G | P | G | V | L | Q | L | L | E | S | L | K | Q | P | S | C |

C-terminal: S L R I I S proportion: 0.57 0.86    1.00 1.00    0.86 0.57 0.43 1.00    0.71 0.71 0.57    1.00 0.43    0.43 0.86 0.71 0.43 0.57 1.00    0.86    0.86
residue: S L    E L    L S S N    L G D    G V    L L C E G L    P    C all RI proportion: 0.50 0.89 0.32 1.00 1.00 0.25 0.82 0.54 0.32 1.00 0.25 0.75 0.79 0.75 0.43 1.00 0.39 0.29 0.4 0.86 0.68 0.39 0.61 0.61 0.36 0.29 0.86 0.26 0.79

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|
| 50%S | L | - | E | L | - | L | S | - | N | - | L | G | D | - | G | - | - | - | L | C | - | G | L | - | - | P | - | C |
| 40%S | L | - | E | L | - | L | S | - | N | - | L | G | D | A | G | - | - | - | L | C | - | G | L | - | - | P | - | C |
| 30%S | L | - | E | L | - | L | S | S/N | N | - | L | G | D | A | G | V | - | - | L | C | E | G | L | L | - | P | - | C |
| 25%S | L | R | E | L | D | L | S | S/N | N | E | L | G | D | A | G | V | R | L | L | C | E | L | L | L | D/Q | P | G | C |
| module | S | L | R | E | L | | 3 L | S | | 3 N | K | L | G | D | A | G | V | R | L | L | L | Q | G | L | L | D | P | G | T |
| | | 2 | | | 5 | | 7 | | | 10 | | 12 | | | | | 17 | | | 20 | 21 | | | 24 | | | | | 29 |

[1] MluI and BssHII have compatible ends
[2] Ligation leads to either the original sites or the combined site termed *.

Figure 7a
I) PCR assembly of a module
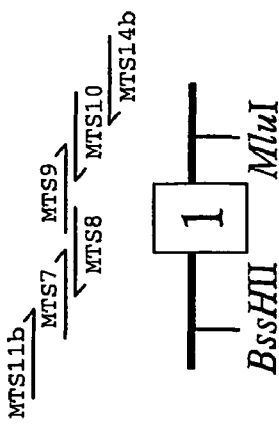
II) Separate digestion with *Mlu*I or *Bss*HII and dimerization by ligation
III) Amplification of the dimer by PCR
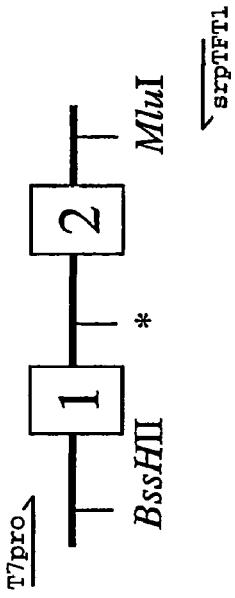

Figure 7b
IV) Separate digestion of the dimer with *Mlu*I or *Bss*HII
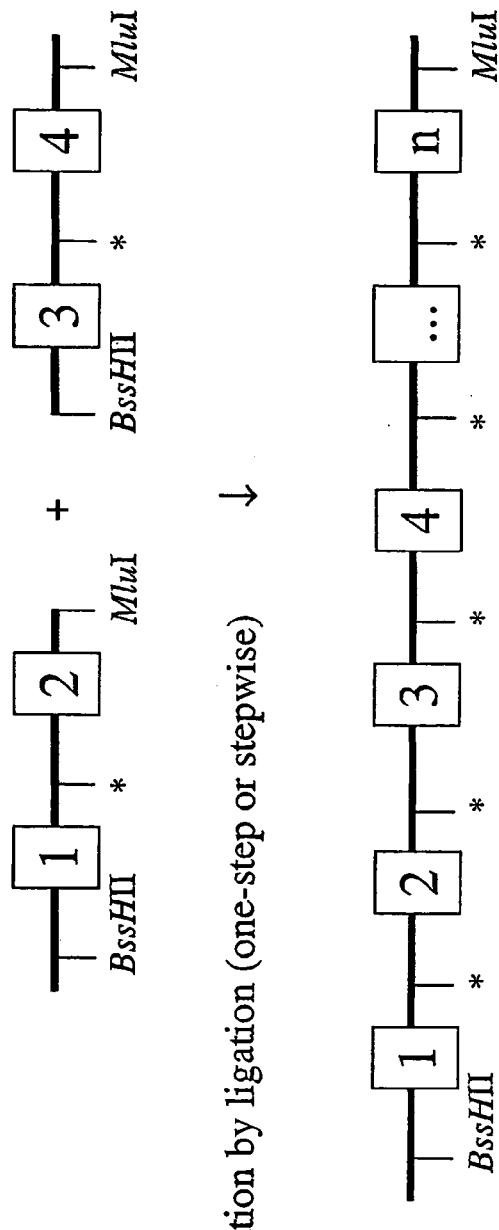
V) Polymerization by ligation (one-step or stepwise)
VI) PCR amplification of a "capping" module and digestion with *Bss*HII
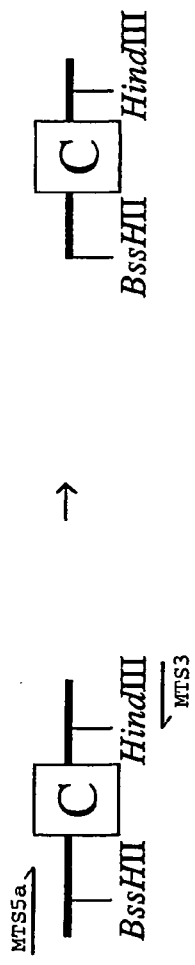

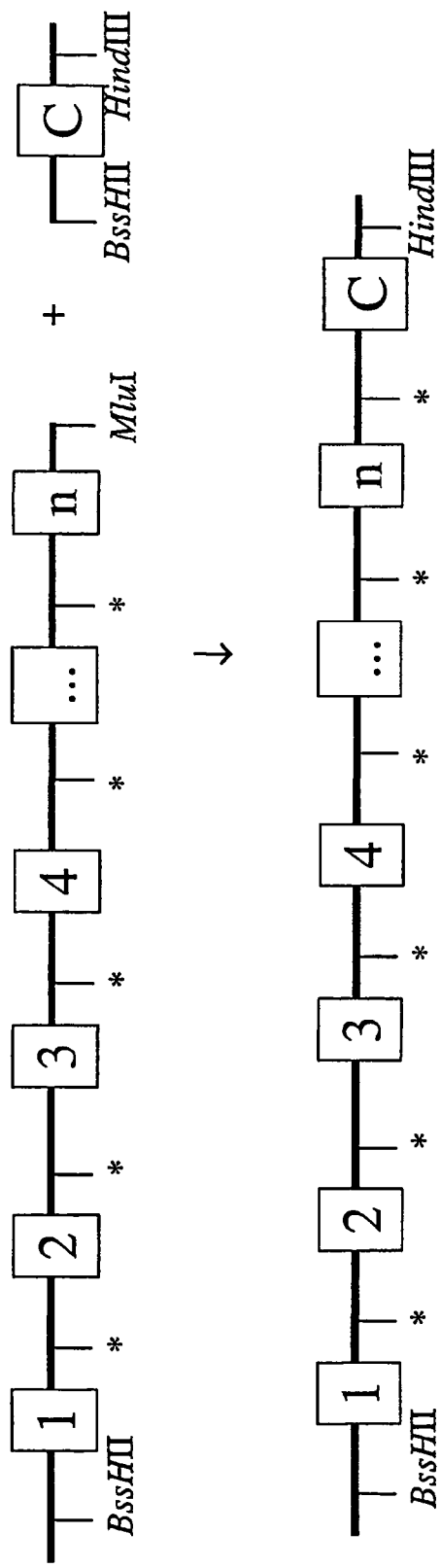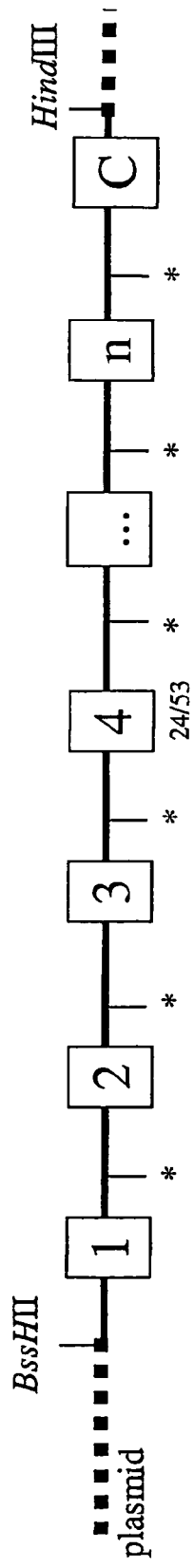
Figure 7c VII) Capping the *Mlu*I digested polymer by ligation
VIII) Cloning into the appropriate plasmid after *Bss*HII, *Mlu*I and *Hind*III digestion

Figure 8

```
          NcoI                              BamHI
           |                                 |
         TCCATGGACTACAAGGATCATCACCATCACCATCACGGATCCctggacatccagAGCCTG
    114  ------+---------+---------+---------+---------+---------+---  173
         AGGTACCTGATGTTCCTAGTAGTGGTAGTGGTAGTGCCTAGGgacctgtaggtcTCGGAC a           M  D  Y  K  D  H  H  H  H  H  G  S  L  D  I  Q  S  L    -

GACATCCAGTGTGAGGAGCTGAGCGACGCTAGATGGGCCGAGCTCCTCcctctgctccag
    174  ------+---------+---------+---------+---------+---------+---  233
         CTGTAGGTCACACTCCTCGACTCGCTGCGATCTACCCGGCTCGAGGAGggagacgaggtc a           D  I  Q  C  E  E  L  S  D  A  R  W  A  E  L  L  P  L  L  Q  -

BssHII
                |
         cagCCGTACGCGCGCCTGGAGNNNCTGNNNCTGNNNNNNNNNNNGACCTCACCGAGGCCGGC
    234  ------+---------+---------+---------+---------+---------+---  293
         gtcGGCATGCGCGCGGACCTCNNNGACNNNGACNNNNNNNNNNNCTGGAGTGGCTCCGGCCG a           Q  P  Y  A  R  L  E  ?  L  ?  L  ?  ?  ?  D  L  T  E  A  G  -

NTGAAGGACCTGGCCAGCGTGCTCCGCTCCAACCCGAGCCTGCGGGAGCTGNNNCTGAGC
    294  ------+---------+---------+---------+---------+---------+---  353
         NACTTCCTGGACCGGTCGCACGAGGCGAGGTTGGGCTCGGACGCCCTCGACNNNGACTCG a           ?  K  D  L  A  S  V  L  R  S  N  P  S  L  R  E  L  ?  L  S  -

NNNAACAAGCTCGGCGATGCAGGCGTGCGGCTGCTCTTGCAGGGGCTGCTGGACCCCGGC
    354  ------+---------+---------+---------+---------+---------+---  413
         NNNTTGTTCGAGCCGCTACGTCCGCACGCCGACGAGAACGTCCCCGACGACCTGGGGCCG a           ?  N  K  L  G  D  A  G  V  R  L  L  L  Q  G  L  L  D  P  G  -

MluI  XhoI
             |    |
         ACGCGTCTCGAGcagctggtccTGTACGACATTTACTGGTCTGAGGAGATGGAGGACCGG
    414  ------+---------+---------+---------+---------+---------+---  473
         TGCGCAGAGCTCgtcgaccaggACATGCTGTAAATGACCAGACTCCTCTACCTCCTGGCC a           T  R  L  E  Q  L  V  L  Y  D  I  Y  W  S  E  E  M  E  D  R  -

CTGCAGGCCCTGGAGAAGGACAAGCCATCcctgagggtcatctccGGTTCCGCTGGCTCC
    474  ------+---------+---------+---------+---------+---------+---  533
         GACGTCCGGGACCTCTTCCTGTTCGGTAGggactcccagtagaggCCAAGGCGACCGAGG a           L  Q  A  L  E  K  D  K  P  S  L  R  V  I  S  G  S  A  G  S  -

NheI  EcoRI  HindIII
                        |     |      |
         GCTGCTGGTTCTGGCGAGGCTAGCGAATTCTGATAAGCTT
    534  ------+---------+---------+---------+---  573
         CGACGACCAAGACCGCTCCGATCGCTTAAGACTATTCGAA a           A  A  G  S  G  E  A  S  E  F  *  *        -
```

Figure 10b

```
       AGGAGCTGCAGCTGCGTAATACTGACCTCACCGAGGCCGgCGTGGAGGACCTGGCCAGCG
  481  ---------+---------+---------+---------+---------+---------+ 540
       TCCTCGACGTCGACGCATTATGACTGGAGTGGCTCCGGCcGCACCTCCTGGACCGGTCGC c         E  L  Q  L  R  N  T  D  L  T  E  A  G  V  E  D  L  A  S  V -

TgCTCCGCTCCAACCCGAGcCTGCGGGAGCTGTCTCTGAGCAATAACAAGCTCGGCGATG
  541  ---------+---------+---------+---------+---------+---------+ 600
       AcGAGGCGAGGTTGGGCTCgGACGCCCTCGACAGAGACTCGTTATTGTTCGAGCCGCTAC c         L  R  S  N  P  S  L  R  E  L  S  L  S  N  N  K  L  G  D  A -

CAGGCGTGCGGCTGCTCTTGCAGGGGCTGCTGGACCCCGGCACGCGCCTGGAGAAGCTGT
  601  ---------+---------+---------+---------+---------+---------+ 650
       GTCCGCACGCCGACGAGAACGTCCCCGACGACCTGGGGCCGTGCGCGGACCTCTTCGACA c         G  V  R  L  L  L  Q  G  L  L  D  P  G  T  R  L  E  K  L  Y -

ATCTGCGTAATACTGACCTCACCGAGGCCGGCATGAAGGACCTGGCCAGCGTgCTCCGCT
  661  ---------+---------+---------+---------+---------+---------+ 720
       TAGACGCATTATGACTGGAGTGGCTCCGGCCGTACTTCCTGGACCGGTCGCAcGAGGCGA c         L  R  N  T  D  L  T  E  A  G  M  K  D  L  A  S  V  L  R  S -

CCAACCCGAGCCTGCGGGAGCTGTCTCTGAGCACTAACAAGCTCGGCGATGCAGGCGTGC
  721  ---------+---------+---------+---------+---------+---------+ 780
       GGTTGGGCTCGGACGCCCTCGACAGAGACTCGTGATTGTTCGAGCCGCTACGTCCGCACG c         N  P  S  L  R  E  L  S  L  S  T  N  K  L  G  D  A  G  V  R -

XhoI
                                                |
       GGCTGcTcTTGCAGGGGCTGCTGGaCCTCGGCACGCGCCTCGAGCAGCTGGTCCTGTACG
  781  ---------+---------+---------+---------+---------+---------+ 840
       CCGACgAgAACGTCCCCGACGACCTGGAGCCGTGCGCGGAGCTCGTCGACCAGGACATGC c         L  L  L  Q  G  L  L  D  L  G  T  R  L  E  Q  L  V  L  Y  D -

ACATTTACTGGTCTGAGGAGATGGAGGACCGGCTGCAGGCCCTGGAGAAGGACAAGCCAT
  841  ---------+---------+---------+---------+---------+---------+ 900
       TGTAAATGACCAGACTCCTCTACCTCCTGGCCGACGTCCGGGACCTCTTCCTGTTCGGTA c         I  Y  W  S  E  E  M  E  D  R  L  Q  A  L  E  K  D  K  P  S -

HindIII
                   |
       CCCTGAGGGTCATCTCCTGATAAgctt
  901  ---------+---------+------- 927
       GGGACTCCCAGTAGAGGACTATTcgaa c         L  R  V  I  S  *  *        -
```

Figure 17

Type II restriction enzymes:

BamHI:  5'...G·GATC·C...3'
        3'...C·CTAG·G...5'

HindIII: 5'...A·AGCT·T...3'
         3'...T·TCGA·A...5'

Type IIs restriction enzymes:

BpiI:  5'...GAAGACNN·NNNN...3'
       3'...CTTCAGNN·NNNN...5'

BsaI:  5'...GGTCTCN·NNNN...3'
       3'...CCAGAGN·NNNN...5'

Figure 21

```
E3-5    1  MRGSHHHHHGSDLGKKLLEAARAGQDDEVRIILMANGADVNATDNDGYTP   50
              · · *** *
              ||| ||  | · ·|
GABP    1  .........DLGKKLLEAARAGQDDEVRIILMANGAPF.TTDWLGTSP    37

**                  * ***·*
E3-5   51  LHLAASNGHLEIVEVLLKNGADVNASDLTGITPLHLAAATGHLEIVEVLL  100
           ||| ||  ||·|||||  |||·|·   ·|||||||·|·||·||·|||||
GABP   38  LHLAAQYGHFSTTEVLLRAGVSRDARTKVDRTPLHMAASEGHANIVEVLL   87

* ***                     *
E3-5  101  KHGADVNAYDNDGHTPLHLAAKYGHLEIVEVLLKHGADVNAQDKFGKTAF  150
           |||||||| · ·||·|||| ||·|·|||·  |||||||·   ·|  |||
GABP   88  KHGADVNAKDMLKMTALHWATEHNHQEVVELLIKYGADVHTQSKFCKTAF  137

E3-5  151  DISIDNGNEDLAEILQ  166
           ||||||||||||||||
GABP  138  DISIDNGNEDLAEILQ  153
```

COLLECTION OF REPEAT PROTEINS COMPRISING REPEAT MODULES

This application is a 371 of PCT/EP01/10454 filed on Sep. 10, 2001, which is hereby incorporated by reference.

The present invention relates to collections of repeat proteins comprising repeat modules which are derived from one or more repeat units of a family of naturally occurring repeat proteins, to collections of nucleic acid molecules encoding said repeat proteins, to methods for the construction and application of such collections and to individual members of such collections.

A number of documents are cited throughout this specification. The disclosure content of these documents is herewith incorporated by reference.

Protein-protein interactions, or more generally, protein-ligand interactions, play an important role in all organisms and the understanding of the key features of recognition and binding is one focus of current biochemical research. Up to now, antibodies and any of the derivatives, which have been elaborated, are mainly used in this field of research. However, antibody technology is afflicted with well-known disadvantages. For instance, antibodies can hardly be applied intracellularly due to the reductive environment in the cytoplasm. Thus, there exists a need for high affinity binding molecules with characteristics that overcome the restriction of antibodies. Such molecules will most probably provide new solutions in medicine, biotechnology, and research, where intracellular binders will also become increasingly important in genomics.

Various efforts to construct novel binding proteins have been reported (reviewed in Nygren and Uhlen, 1997). The most promising strategy seemed to be a combination of limited library generation and screening or selection for the desired properties. Usually, existing scaffolds were recruited to randomise some exposed amino acid residues after analysis of the crystal structure. However, despite progress in terms of stability and expressibility, the affinities reported so far are considerably lower than the ones of antibodies (Ku and Schultz, 1995). A constraint might be the limitation to targets for which the crystal structure is known (Kirkham et al., 1999) or which are homologous to the original target molecule, so that no universal scaffold for binding has been identified so far. To increase the apparent affinity of binders after screening, several approaches have used multimerisation of single binders to take advantage of avidity effects.

Thus, the technical problem underlying the present invention is to identify novel approaches for the construction of collections of binding proteins.

The solution to this technical problem is achieved by providing the embodiments characterised in the claims. Accordingly, the present invention allows constructing collections of repeat proteins comprising repeat modules. The technical approach of the present invention, i.e. to derive said modules from the repeat units of naturally occurring repeat proteins, is neither provided nor suggested by the prior art.

Thus, the present invention relates to collections of nucleic acid molecules encoding collections of repeat proteins, each repeat protein comprising a repeat domain, which comprises a set of consecutive repeat modules, wherein each of said repeat modules is derived from one or more repeat units of one family of naturally occurring repeat proteins, wherein said repeat units comprise framework residues and target interaction residues, wherein said repeat proteins differ in at least one position corresponding to one of said target interaction residues.

In the context of the present invention, the term "collection" refers to a population comprising at least two different entities or members. Preferably, such a collection comprises at least $10^5$, more preferably more than $10^7$, and most preferably more that $10^9$ different members. A "collection" may as well be referred to as a "library" or a "plurality".

The term "nucleic acid molecule" refers to a polynucleotide molecule, which is a ribonucleic acid (RNA) or deoxyribonucleic acid (DNA) molecule, either single stranded or double stranded. A nucleic acid molecule may either be present in isolated form, or be comprised in recombinant nucleic acid molecules or vectors.

The term "repeat proteins" refers to a (poly)peptide/protein comprising one or more repeat domains (FIG. 1). Preferably, each of said repeat proteins comprises up to four repeat domains. More preferably, each of said repeat proteins comprises up to two repeat domains. However, most preferably, each of the repeat proteins comprises one repeat domain. Furthermore, said repeat protein may comprise additional non-repeat protein domains (FIGS. 2a and 2b), (poly)peptide tags and/or (poly)peptide linker sequences (FIG. 1). The term "(poly)peptide tag" refers to an amino acid sequence attached to a (poly)peptide/protein, where said amino acid sequence is usable for the purification, detection, or targeting of said (poly)peptide/protein, or where said amino acid sequence improves the physio-chemical behavior of said (poly)peptide/protein, or where said amino acid sequence possesses an effector function. Such (poly)peptide tags may be small polypeptide sequences, for example, $His_n$ (Hochuli et al., 1988; Lindner et al., 1992), myc, FLAG (Hopp et al., 1988; Knappik and Plückthun, 1994), or Strep-tag (Schmidt and Skerra, 1993; Schmidt and Skerra, 1994; Schmidt et al., 1996. These (poly)peptide tags are all well known in the art and are fully available to the person skilled in the art. Additional non-repeat domains may be further moieties such as enzymes (for example enzymes like alkaline phosphatase), which allow the detection of said repeat proteins, or moieties which can be used for targeting (such as immunoglobulins or fragments thereof) and/or as effector molecules. The individual (poly)peptide tags, moieties and/or domains of a repeat protein may be connected to each other directly or via (poly)peptide linkers. The term "(poly)peptide linker" refers to an amino acid sequence, which is able to link, for example two protein domains, a (poly)peptide tag and a protein domain or two sequence tags. Such linkers for example glycine-serine-linkers of variable lengths (e.g. Forrer and Jaussi, 1998), are known to the person skilled in the relevant art.

In the context of the present invention, the term "(poly)peptide" relates to a molecule consisting of one or more chains of multiple, i.e. two or more, amino acids linked via peptide bonds.

The term "protein" refers to a (poly)peptide, where at least part of the (poly)peptide has, or is able to, acquire a defined three-dimensional arrangement by forming secondary, tertiary, or quaternary structures within and/or between its (poly)peptide chain(s). If a protein comprises two or more (poly)peptides, the individual (poly)peptide chains may be linked non-covalently or covalently, e.g. by a disulfide bond between two (poly)peptides. A part of a protein, which individually has, or is able to, acquire a defined three-dimensional arrangement by forming secondary or tertiary structures is termed "protein domain". Such protein domains are well known to the practitioner skilled in the relevant art.

The term "family of naturally occurring repeat proteins" refers to a group of naturally occurring repeat proteins, where the members of said group comprise similar repeat units. Protein families are well known to the person skilled in the art.

Figures 2C, 4A:
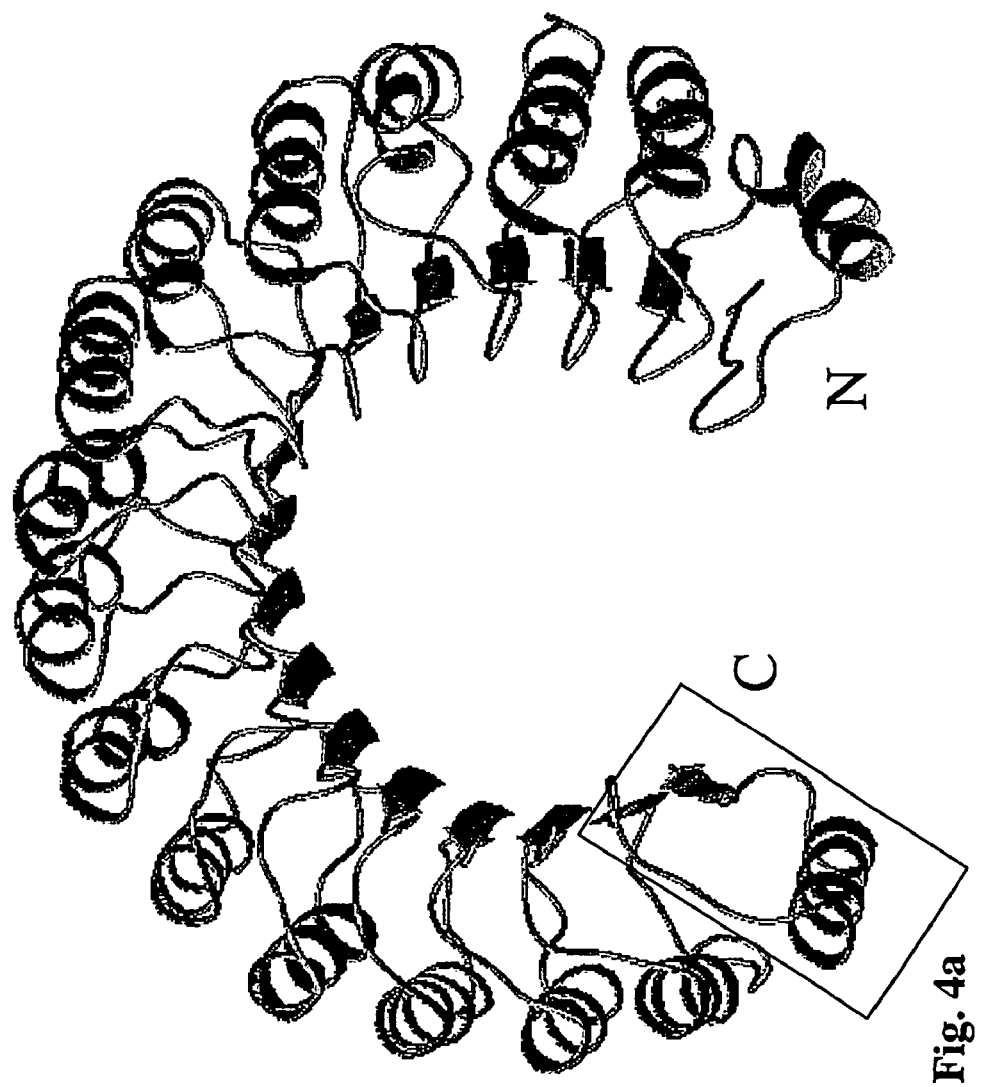

The term "repeat domain" refers to a protein domain comprising two or more consecutive repeat units (modules) as structural units (FIG. 1), wherein said structural units have the same fold, and stack tightly to create a superhelical structure having a joint hydrophobic core (for a review see Kobe and Kajava, 2000). The term "structural unit" refers to a locally ordered part of a (poly)peptide, formed by three-dimensional interactions between two or more segments of secondary structure that are near one another along the (poly)peptide chain. Such a structural unit comprises a structural motif. The term "structural motif" refers to a three-dimensional arrangement of secondary structure elements present in at least one structural unit. For example, the structural motif repetitively present in LRR proteins consists of a β-strand and an opposing antiparallel helical segment connected by a loop (FIG. 4a). Structural motifs are well known to the person skilled in the relevant art. Said structural units are alone not able to acquire a defined three-dimensional arrangement; however, their consecutive arrangement as repeat modules in a repeat domain leads to a mutual stabilization of neighbouring units resulting in said superhelical structure.

Figure 3:
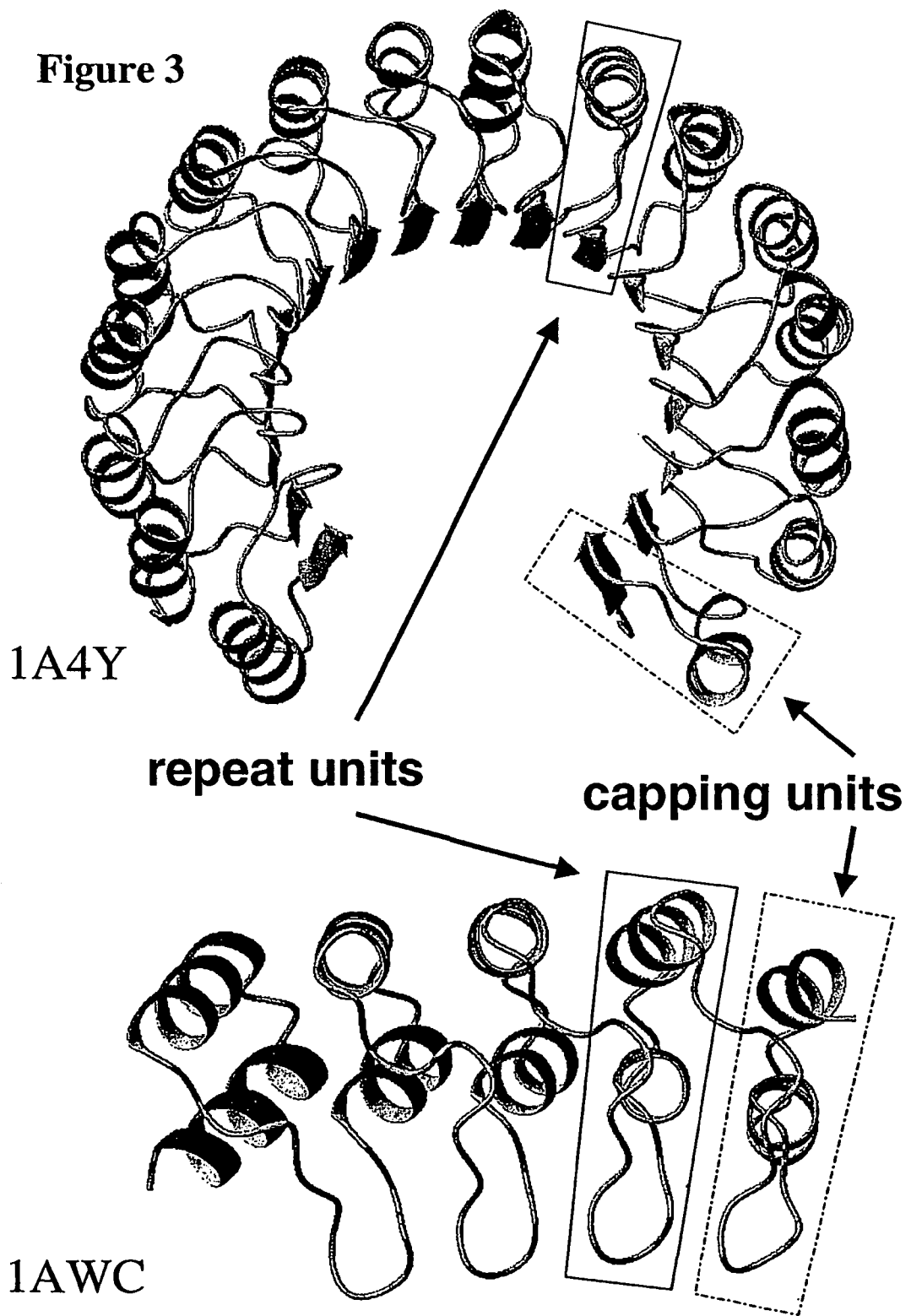

The term "repeat modules" refers to the repeated amino acid sequences of the repeat proteins encoded by the nucleic acid molecules of the collection of the present invention, which are derived from the repeat units (FIG. 3) of naturally occurring proteins. Each repeat module comprised in a repeat domain is derived from one or more repeat units of one family of naturally occurring repeat proteins.

Such "repeat modules" may comprise positions with amino acid residues present in all copies of the repeat module ("fixed positions") and positions with differing or "randomised" amino acid residues ("randomised positions").

The term "set of repeat modules" refers to the total number of repeat modules present in a repeat domain. Such "set of repeat modules" present in a repeat domain comprises two or more consecutive repeat modules, and may comprise just one type of repeat module in two or more copies, or two or more different types of modules, each present in one or more copies. The collection of repeat proteins according to the present invention may comprise repeat domains with identical number of repeat modules per corresponding repeat domain (i.e. one set with a fixed number of repeat modules), or may comprise repeat domains, which differ in the number of repeat modules per corresponding repeat domain (i.e. two or more sets with different numbers of repeat modules).

Preferably, the repeat modules comprised in a set are homologous repeat modules. In the context of the present invention, the term "homologous repeat modules" refers to repeat modules, wherein more than 70% of the framework residues of said repeat modules are homologous. Preferably, more than 80% of the framework residues of said repeat modules are homologous. Most preferably, more than 90% of the framework residues of said repeat modules are homologous. Computer programs to determine the percentage of homology between polypeptides, such as Fasta, Blast or Gap, are known to the person skilled in the relevant art.

Preferably, a repeat module of the present invention is derived from one repeat unit. This may refer to a situation where a collection of nucleic acid molecules, each molecule encoding a repeat domain of the invention, is obtained by random mutagenesis of a nucleic acid molecule encoding a naturally occurring repeat domain. Thus, said repeat domain of the present invention comprises a set of repeat modules, wherein each of said modules is derived from the corresponding repeat unit of said naturally occurring repeat domain. Methods for random mutagenesis of nucleic acid molecules such as error-prone PCR (Wilson and Keefe, 2000) or DNA shuffling (Volkov and Arnold, 2000) are well known to the person skilled in the relevant art. In another situation, a single naturally occurring repeat unit may be used to derive a repeat sequence motif of the present invention.

More preferably, a repeat module of the present invention is derived from one or more repeat units. This may refer to a situation where two or more homologous nucleic acid molecules, each encoding a naturally occurring repeat domain, are subjected to DNA recombination or random chimeragenesis (Volkov and Arnold, 2000). Thus, said repeat domain of the present invention comprises a set of repeat modules, wherein each of said modules is derived from one or more corresponding repeat units of said homologous naturally occurring repeat domains. Preferably, said homologous nucleic acid molecules possess a DNA sequences identity of at least 75%. More preferably said sequence identity is at least 85%.

Most preferably, a repeat module of the present invention is derived from two or more repeat units, where two or more homologous repeat units are used to derive a repeat sequence motif of the present invention. Descriptions of such a derivation process are presented in the examples.

The term "a repeat module derived from one or repeat units" refers to
(i) a process comprising the analysis of one or more repeat units of naturally occurring repeat proteins and the deduction of a repeat module. This process may comprise the steps of:
(a) identifying naturally occurring repeat units;
(b) determining an initial repeat sequence motif by sequence alignments;
(c) refining the repeat sequence motif by sequence analysis and structural analysis of said repeat units;
(d) constructing a repeat module according to the repeat sequence motif of (c); or
(ii) a process comprising the process of (i) followed by further evolution of the repeat module by random mutagenesis or random chimeragenesis.

Figure 4A:
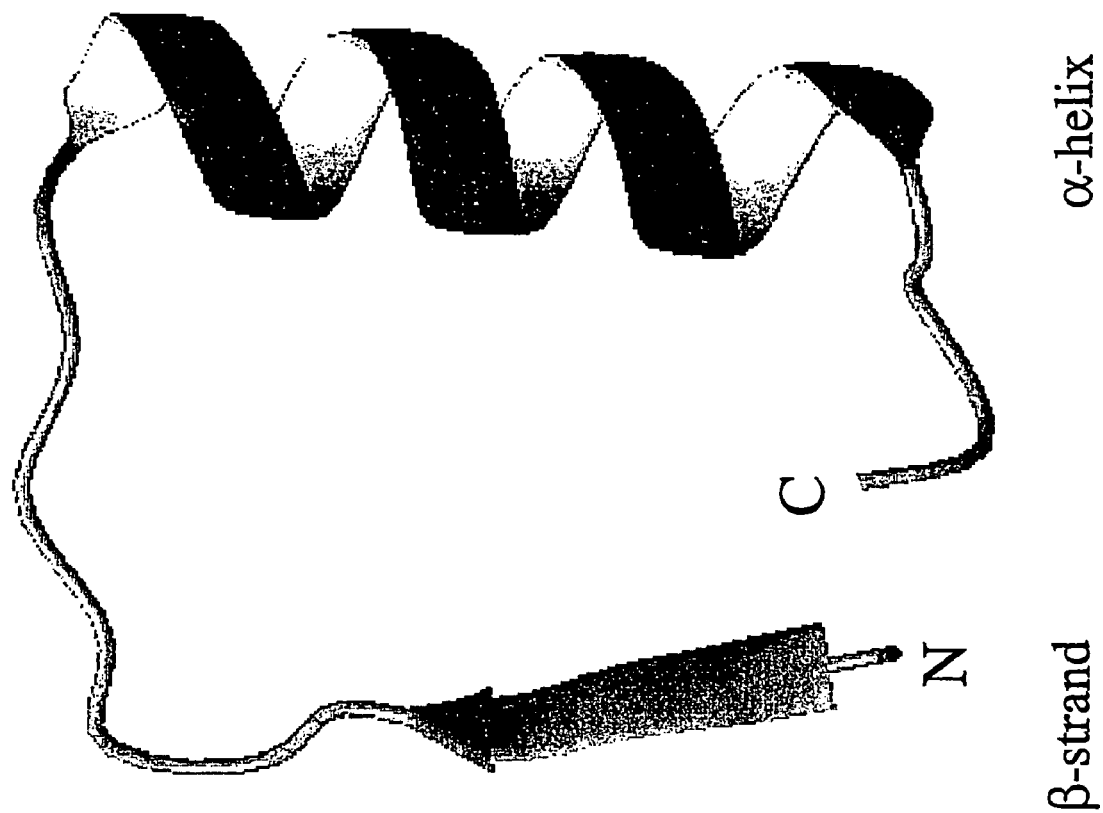
Figure 4B:
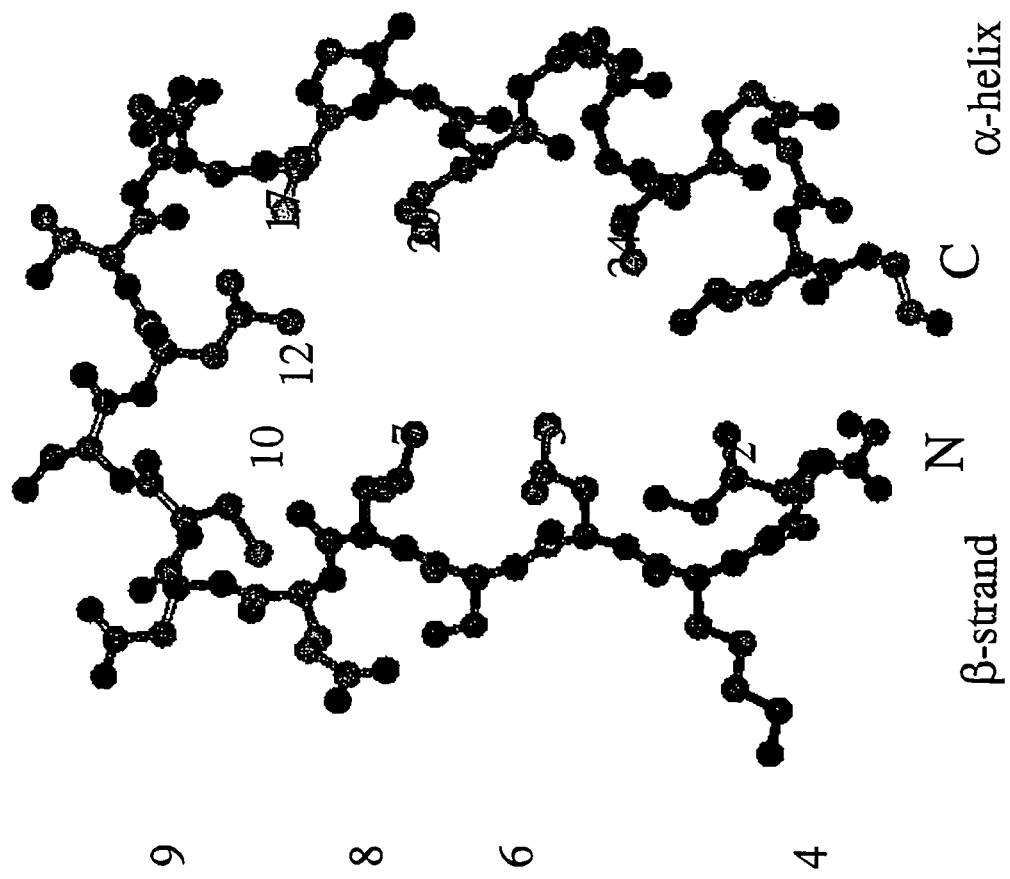

The term "repeat unit" refers to amino acid sequences comprising sequence motifs of one or more naturally occurring proteins, wherein said "repeat units" are found in multiple copies, and which exhibit a defined folding topology common to all said motifs determining the fold of the protein. Such repeat units comprise framework residues (FIG. 4d) and interaction residues (FIG. 4e). Examples of such repeat units include leucine-rich repeat units, ankyrin repeat units, armadillo repeat units, tetratricopeptide repeat units, HEAT repeat units, and leucine-rich variant repeat units (reviewed in Kobe & Deisenhofer, 1994; Groves & Barford, 1999; Marino et al., 2000; Kobe, 1996). Naturally occurring proteins containing two or more such repeat units are referred to as "naturally occurring repeat proteins". The amino acid sequences of the individual repeat units of a repeat protein may have a significant number of mutations, substitutions, additions and/or deletions when compared to each other, while still substantially retaining the general pattern, or motif, of the repeat units.

Preferably, the repeat units used for the deduction of a repeat sequence motif are homologous repeat units, wherein the repeat units comprise the same structural motif and wherein more than 70% of the framework residues of said repeat units are homologous. Preferably, more than 80% of the framework residues of said repeat units are homologous. Most preferably, more than 90% of the framework residues of said repeat units are homologous.

The term "repeat sequence motif" refers to an amino acid sequence, which is deduced from one or more repeat units.

Such repeat sequence motifs comprise framework residue positions and target interaction residue positions. Said framework residue positions correspond to the positions of framework residues of said repeat units. Said target interaction residue positions correspond to the positions of target interaction residues of said repeat units. Such repeat sequence motifs comprise fixed positions and randomized positions. The term "fixed position" refers to an amino acid position in a repeat sequence motif, wherein said position is set to a particular amino acid. Most often, such fixed positions correspond to the positions of framework residues. The term "randomized position" refers to an amino acid position in a repeat sequence motif, wherein two or more amino acids are allowed at said amino acid position. Most often, such randomized positions correspond to the positions of target target interaction residues. However, some positions of framework residues may also be randomized. Amino acid sequence motifs are well known to the practitioner in the relevant art.

The term "folding topology" refers to the tertiary structure of said repeat units. The folding topology will be determined by stretches of amino acids forming at least parts of α-helices or β-sheets, or amino acid stretches forming linear polypeptides or loops, or any combination of α-helices, β-sheets and/or linear polypeptides/loops.

The term "consecutive" refers to an arrangement, wherein said modules are arranged in tandem.

In repeat proteins, there are at least 2, usually about 2 to 6, more usually at least about 6, frequently 20 or more repeat units. For the most part, the repeat proteins are structural proteins and/or adhesive proteins, being present in prokaryotes and eukaryotes, including vertebrates and non-vertebrates. An analogy of ankyrin proteins to antibodies has been suggested (Jacobs and Harrison, 1998).

In most cases, said repeat units will exhibit a high degree of sequence identity (same amino acid residues at corresponding positions) or sequence similarity (amino acid residues being different, but having similar physicochemical properties), and some of the amino acid residues might be key residues being strongly conserved in the different repeat units found in naturally occurring proteins.

However, a high degree of sequence variability by amino acid insertions and/or deletions, and/or substitutions between the different repeat units found in naturally occurring proteins will be possible as long as the common folding topology is maintained.

Methods for directly determining the folding topology of repeat proteins by physicochemical means such as X-ray crystallography, NMR or CD spectroscopy, are well known to the practitioner skilled in the relevant art. Methods for identifying and determining repeat units or repeat sequence motifs, or for identifying families of related proteins comprising such repeat units or motifs, such as homology searches (BLAST etc.) are well established in the field of bioinformatics, and are well known to the practitioner in such art. The step of refining an initial repeat sequence motif may comprise an iterative process.

Crystal structures have been reported for ankyrin-type repeats (Bork, 1993; Huxford et al., 1998, see FIGS. 2g and 2h), the ribonuclease inhibitor (RI) of the leucine-rich repeat (LRR) superfamily (Kobe and Deisenhofer, 1993, see FIG. 2c) and other LRR proteins (see FIG. 2d to 2f). Inspection of these structures revealed an elongated shape in the case of the ankyrin repeats, or a horseshoe shape in the case of the leucine-rich repeats giving rise to an extraordinarily large surface.

The term "framework residues" relates to amino acid residues of the repeat units, or the corresponding amino acid residues of the repeat modules, which contribute to the folding topology, i.e. which contribute to the fold of said repeat unit (or module) or which contribute to the interaction with a neighboring unit (or module). Such contribution might be the interaction with other residues in the repeat unit (module) (4d), or the influence on the polypeptide backbone conformation as found in α-helices or β-sheets, or amino acid stretches forming linear polypeptides or loops. The term "target interaction residues" refers to amino acid residues of the repeat units, or the corresponding amino acid residues of the repeat modules, which contribute to the interaction with target substances. Such contribution might be the direct interaction with the target substances (FIG. 4e), or the influence on other directly interacting residues, e.g. by stabilising the conformation of the (poly)peptide of said repeat unit (module) to allow or enhance the interaction of said directly interacting residues with said target. Such framework and target interaction residues may be identified by analysis of the structural data obtained by the physicochemical methods referred to above, or by comparison with known and related structural information well known to practitioners in structural biology and/or bioinformatics.

The term "interaction with said target substances" may be, without being limited to, binding to a target, involvement in a conformational change or a chemical reaction of said target, or activation of said target.

A "target" may be an individual molecule such as a nucleic acid molecule, a (poly)peptide protein, a carbohydrate, or any other naturally occurring molecule, including any part of such individual molecule, or complexes of two or more of such molecules. The target may be a whole cell or a tissue sample, or it may be any non-naturally occurring molecule or moiety.

The term "differ in at least one position" refers to a collection of repeat proteins, which have at least one position where more than one amino acid may be found. Preferably, such positions are randomised. The term "randomised" refers to positions of the repeat modules, which are variable within a collection and are occupied by more than one amino acid residue in the collection. Preferably, the randomised positions vary additionally between repeat modules within one repeat domain. Preferably, such positions may be fully randomised, i.e. being occupied by the full set of naturally occurring, proteinogenic amino acid residues. More preferably, such positions may be partially randomised, i.e. being occupied by a subset of the full set of naturally occurring amino acid residues. Subsets of amino acid residues may be sets of amino acid residues with common physicochemical properties, such as sets of hydrophobic, hydrophilic, acidic, basic, aromatic, or aliphatic amino acids, subsets comprising all except for certain non-desired amino acid residues, such as sets not comprising cysteines or prolines, or subsets comprising all amino acid residues found at the corresponding position in naturally occurring repeat proteins. The randomisation may be applied to some, preferably to all of the target interaction residues. Methods for making "randomised" repeat proteins such as by using oligonucleotide-directed mutagenesis of the nucleic acid sequences encoding said repeat proteins (e.g. by using mixtures of mononucleotides or trinucleotides (Virnekäs et al., 1994)), or by using error-prone PCR during synthesis of said nucleic acid sequences, are well known to the practitioner skilled in the art.

In a preferred embodiment, each of said repeat modules has an amino acid sequence, wherein at least 70% of the amino acid residues correspond either (i) to consensus amino acid residues deduced from the amino acid residues found at the corresponding positions of at least two naturally occurring repeat units; or (ii) to the amino acid residues found at the corresponding positions in a naturally occurring repeat unit.

Figure 5A:
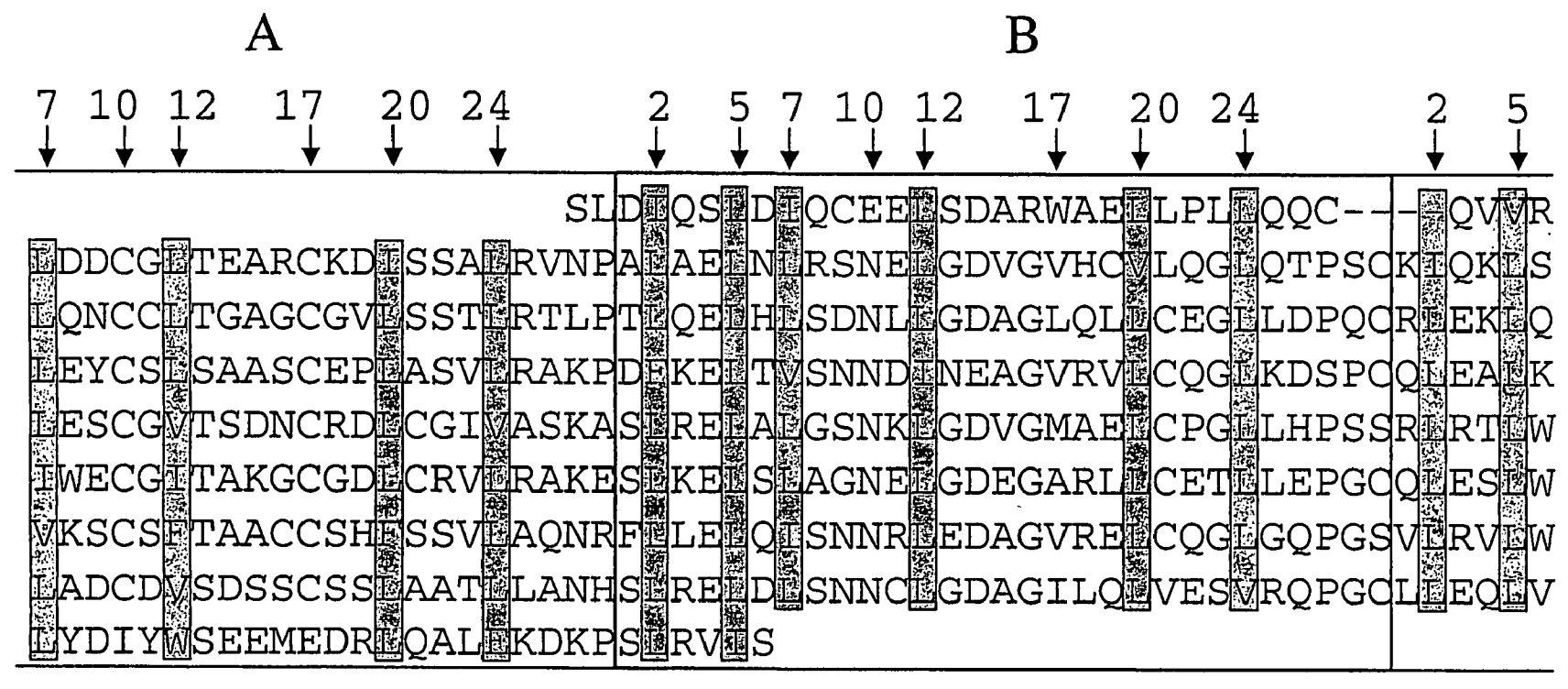
Figure 5B:
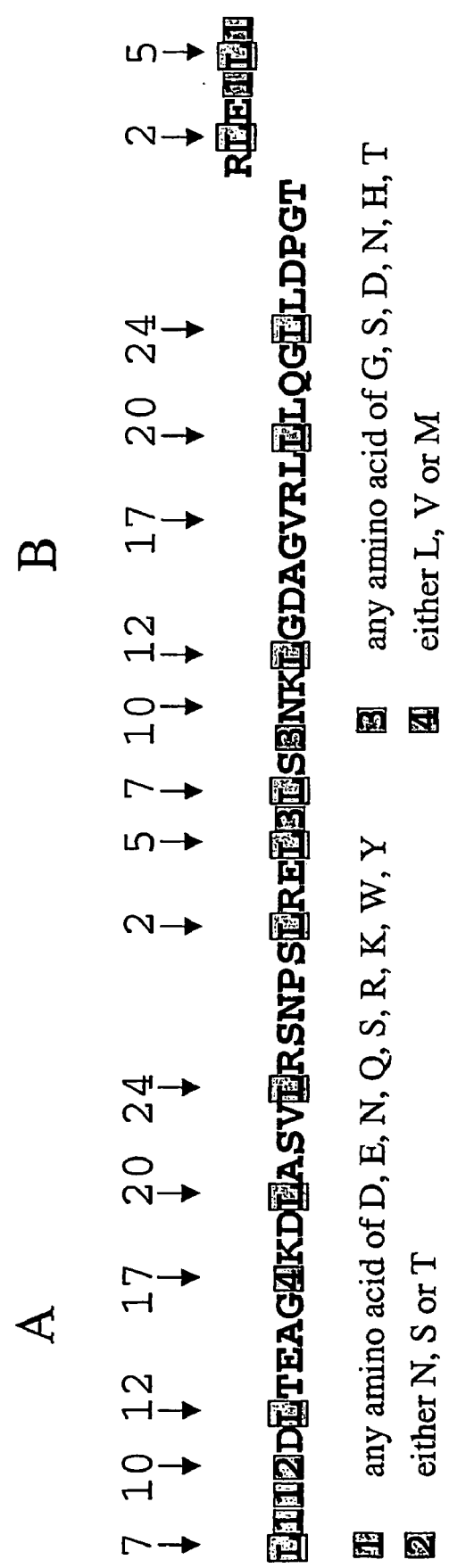

A "consensus amino acid residue" may be found by aligning two or more repeat units based on structural and/or sequence homology determined as described above, and by identifying one of the most frequent amino acid residue for each position in said units (an example is shown in FIGS. 5a and 5b). Said two or more repeat units may be taken from the repeat units comprised in a single repeat protein, or from two or more repeat proteins. If two or more amino acid residues are found with a similar probability in said two ore more repeat units, the consensus amino acid may be one of the most frequently found amino acid or a combination of said two or more amino acid residues.

Further preferred is a collection, wherein said set consists of between two and about 30 repeat modules.

More preferably, said set consists of between 6 and about 15 repeat modules.

In a yet further preferred embodiment of the present invention, said repeat modules are directly connected.

In the context of the present invention, the term "directly connected" refers to repeat modules, which are arranged as direct repeats in a repeat protein without an intervening amino acid sequence.

In a still further preferred embodiment, said repeat modules are connected by a (poly)peptide linker.

Thus, the repeat modules may be linked indirectly via a (poly)peptide linker as intervening sequence separating the individual modules. An "intervening sequence" may be any amino acid sequence, which allows to connect the individual modules without interfering with the folding topology or the stacking of the modules. Preferentially, said intervening sequences are short (poly)peptide linkers of less than 10, and even more preferably, of less than 5 amino acid residues.

In a still further preferred embodiment of the collection of the present invention, each of said repeat proteins further comprises an N- and/or a C-terminal capping module (FIG. 1) having an amino acid sequence different from any one of said repeat modules.

The term "capping module" refers to a polypeptide fused to the N- or C-terminal repeat module of a repeat domain, wherein said capping module forms tight tertiary interactions with said repeat module thereby providing a cap that shields the hydrophobic core of said repeat module at the side not in contact with the consecutive repeat module from the solvent (FIG. 1).

Said N- and/or C-terminal capping module may be, or may be derived from, a capping unit (FIG. 3) or other domain found in a naturally occurring repeat protein adjacent to a repeat unit. The term "capping unit" refers to a naturally occurring folded (poly)peptide, wherein said (poly)peptide defines a particular structural unit which is N- or C-terminally fused to a repeat unit, wherein said (poly)peptide forms tight tertiary interactions with said repeat unit thereby providing a cap that shields the hydrophobic core of said repeat unit at one side from the solvent. Such capping units may have sequence similarities to said repeat sequence motif.

In a preferred embodiment, the present invention relates to a collection of nucleic acid molecules, wherein said repeat units are ankyrin repeat units.

The characteristics of ankyrin repeat proteins have been reviewed (Sedgwick and Smerdon, 1999) and one minimal folding unit has been investigated (Zhang and Peng, 2000). Ankyrin repeat proteins have been studied in some detail, and the data can be used to exemplify the construction of repeat proteins according to the present invention.

Ankyrin repeat proteins have been identified in 1987 through sequence comparisons between four such proteins in *Saccharomyces cerevisiae, Drosophila melanogaster* and *Caenorhabditis elegans*. Breeden and Nasmyth reported multiple copies of a repeat unit of approximately 33 residues in the sequences of swi6p, cdc10p, notch and lin-12 (Breeden and Nasmyth, 1987). The subsequent discovery of 24 copies of this repeat unit in the ankyrin protein led to the naming of this repeat unit as the ankyrin repeat (Lux et al., 1990). Later, this repeat unit has been identified in several hundreds of proteins of different organisms and viruses (Bork, 1993; SMART database, Schultz et al., 2000). These proteins are located in the nucleus, the cytoplasm or the extracellular space. This is consistent with the fact that the ankyrin repeat domain of these proteins is independent of disulfide bridges and thus independent of the oxidation state of the environment. The number of repeat units per protein varies from two to more than twenty (SMART database, Schultz et al., 2000). A minimum number of repeat units seems to be required to form a stable folded domain (Zhang and Peng, 2000). On the other hand, there is also some evidence for an upper limit of six repeat units being present in one folded domain (Michaely and Bennet, 1993).

Figure 4C:
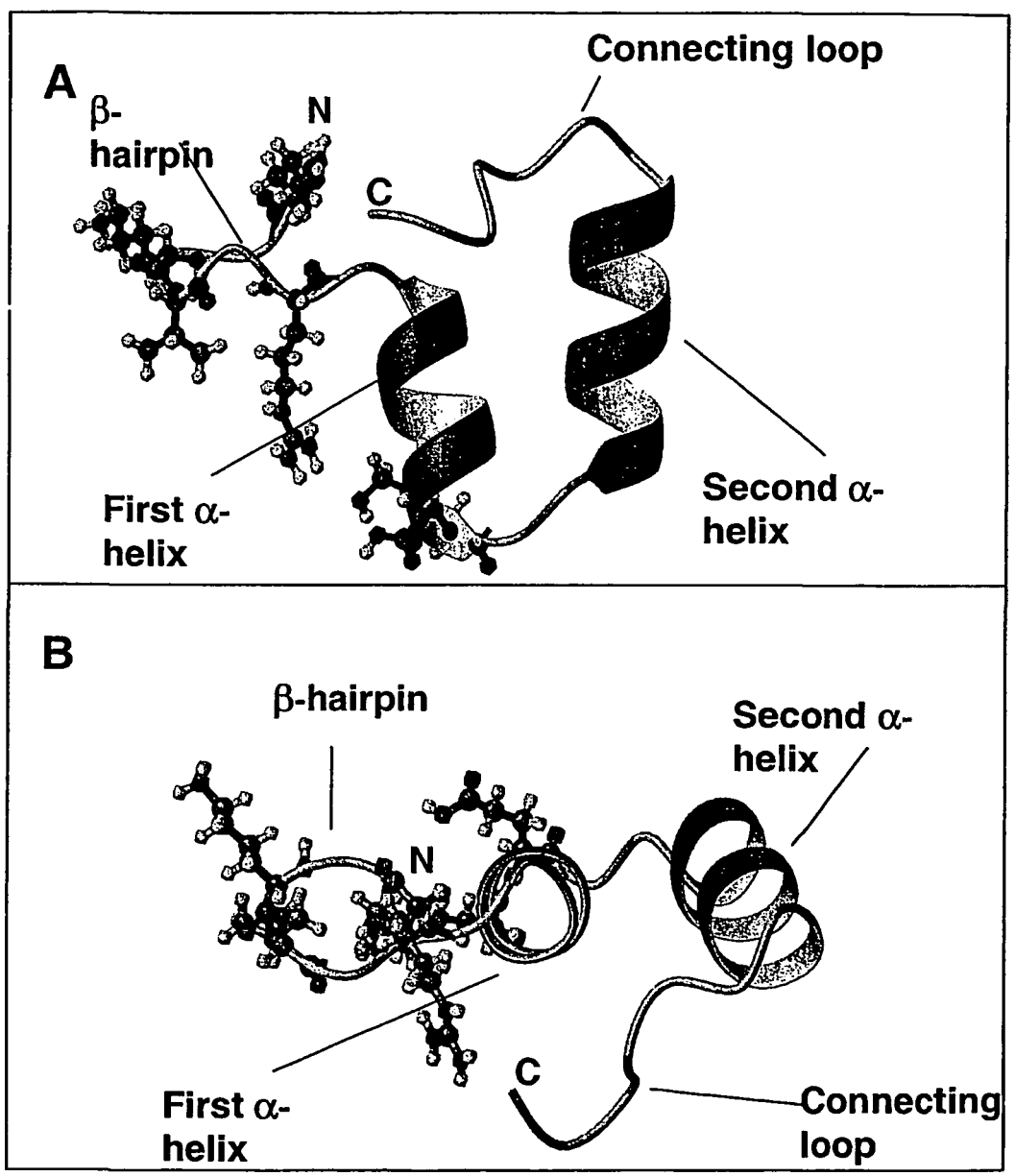
Figure 4D:
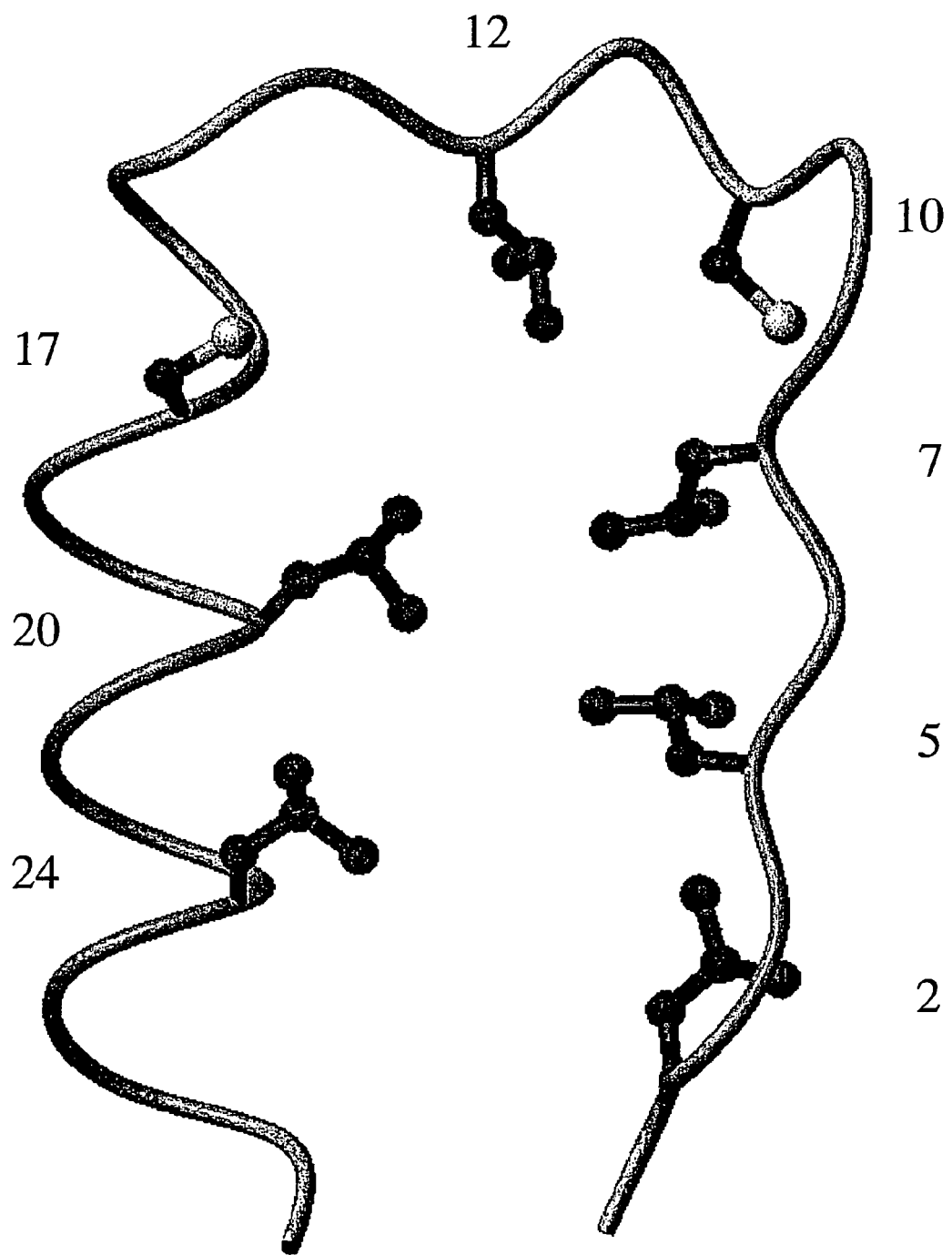
Figure 4E:
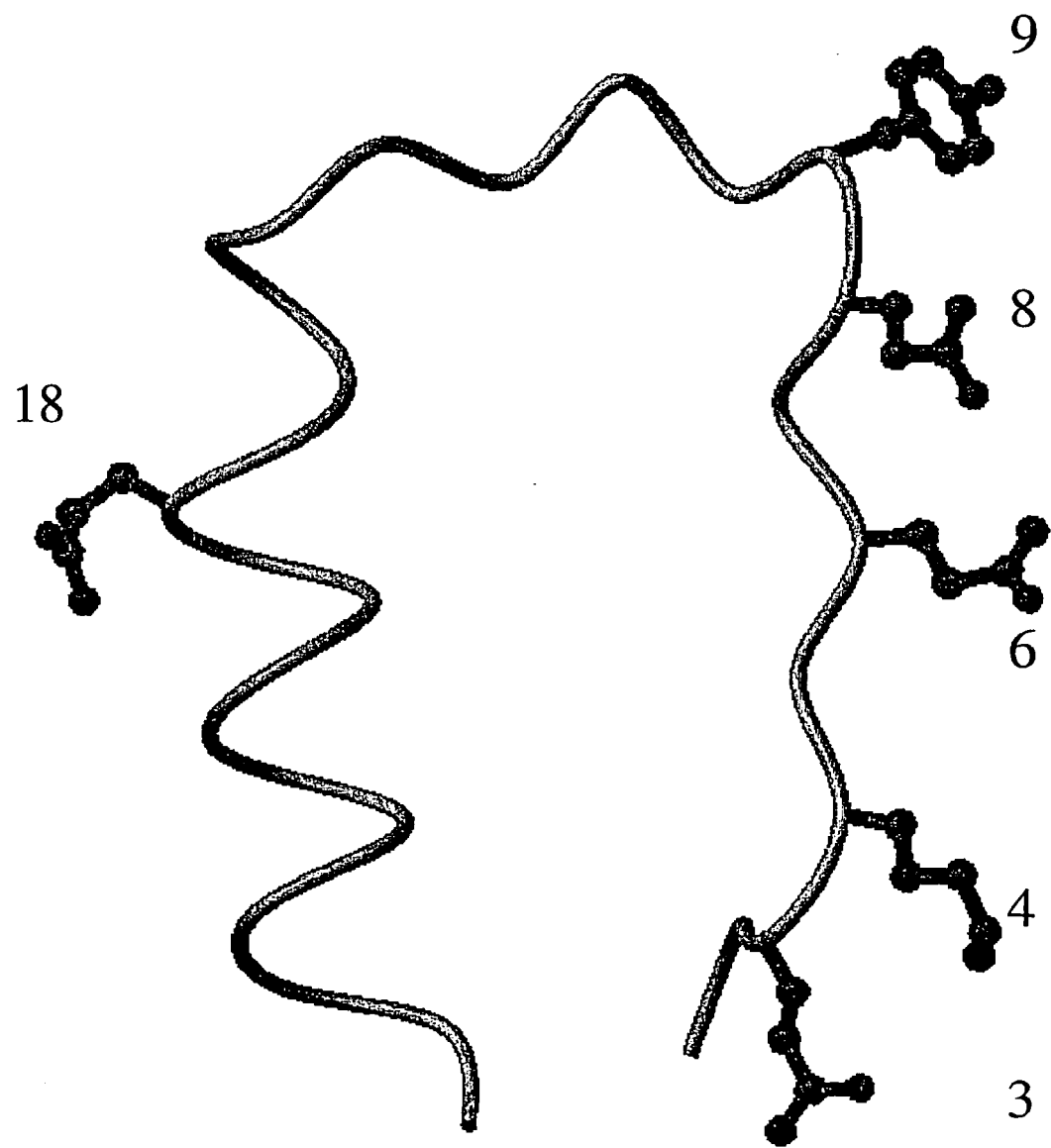

All so far determined tertiary structures of ankyrin repeat units share a characteristic fold (Sedgwick and Smerdon, 1999) composed of a β-hairpin followed by two antiparallel α-helices and ending with a loop connecting the repeat unit with the next one (FIG. 4c). Domains built of ankyrin repeat units are formed by stacking the repeat units to an extended and curved structure. This is illustrated by the structure of the mouse GA-binding protein beta 1 subunit in FIG. 2h.

Proteins containing ankyrin repeat domains often contain additional domains (SMART database, Schultz et al., 2000). While the latter domains have variable functions, the function of the ankyrin repeat domain is most often the binding of other proteins, as several examples show (Batchelor et al., 1998; Gorina and Pavletich, 1996; Huxford et al., 1999; Jacobs and Harrisson, 1999; Jeffrey et al., 2000). When analysing the repeat units of these proteins, the target interaction residues are mainly found in the β-hairpin and the exposed part of the first α-helix (FIG. 4c). These target interaction residues are hence forming a largecontact surface on the ankyrin repeat domain. This contact surface is exposed on a framework built of stacked units of α-helix 1, α-helix 2 and the loop (FIG. 4c). For an ankyrin repeat protein consisting of five repeat units, this interaction surface contacting other proteins is approximately 1200 Å$^2$. Such a large interaction surface is advantageous to achieve high affinities to target molecules. The affinity of IkBa (which contains a domain of six ankyrin repeat units) to the NF-kB heterodimer for example is $K_D$=3 nM (Malek et al., 1998), whereas the dissociation constant of human GA-binding protein beta 1 to its alpha unit is $K_D$=0.78 nM (Suzuki et al., 1998 An advantage of the use of ankyrin repeat proteins according to the present invention over widely used antibodies is their potential to be expressed in a recombinant fashion in large amounts as soluble, monomeric and stable molecules (example 2).

Further preferred is a collection, wherein each of said repeat modules comprises the ankyrin repeat consensus sequence DxxGxTPLHLAaxx±±±±±±±±±±±GpxpaVpxLLpxGA±±±±±DVNAx (SEQ ID NO: 1), wherein "x" denotes any amino acid, "±" denotes any amino acid or a deletion, "a" denotes an amino acid with an apolar side chain, and "p" denotes a residue with a polar sidechain. Most preferred is a collection, wherein one or more of the positions denoted "x" are randomised.

Particularly preferred is a collection, wherein each of said repeat modules comprises the ankyrin repeat consensus sequence DxxGxTPLHLAxxxGxxxVVxLLLxxGADVNAx(SEQ ID NO: 2), wherein "x" denotes any amino acid.

Even more preferred is a diverse collection, wherein each of said repeat modules comprises the ankyrin repeat sequence motif DxxGxTPLHLAxxxGxxxIVxVLLxxGADVNAx(SEQ ID NO: 3), wherein "x" denotes any amino acid.

Yet more preferred is a diverse collection, wherein each of said repeat modules comprises the ankyrin repeat sequence motif

D11G1TPLHLAA11GHLEIVEVLLK2GADVNA1 (SEQ ID NO: 4), wherein 1 represents an amino acid residue selected from the group:
A, D, E, F, H, I, K, L, M, N, Q, R, S, T, V, W and Y;
wherein 2 represents an amino acid residue selected from the group:
H, N and Y.

In a further preferred embodiment, the present invention relates to a collection of nucleic acid molecules, wherein said repeat units are leucine-rich repeats (LRR).

The characteristics and properties of the LRR repeat have been reviewed (Kobe and Deisenhofer, 1994). LRR proteins have been studied in some detail, and the data can be used to exemplify the behaviour of repeat proteins.

Figure 2D:
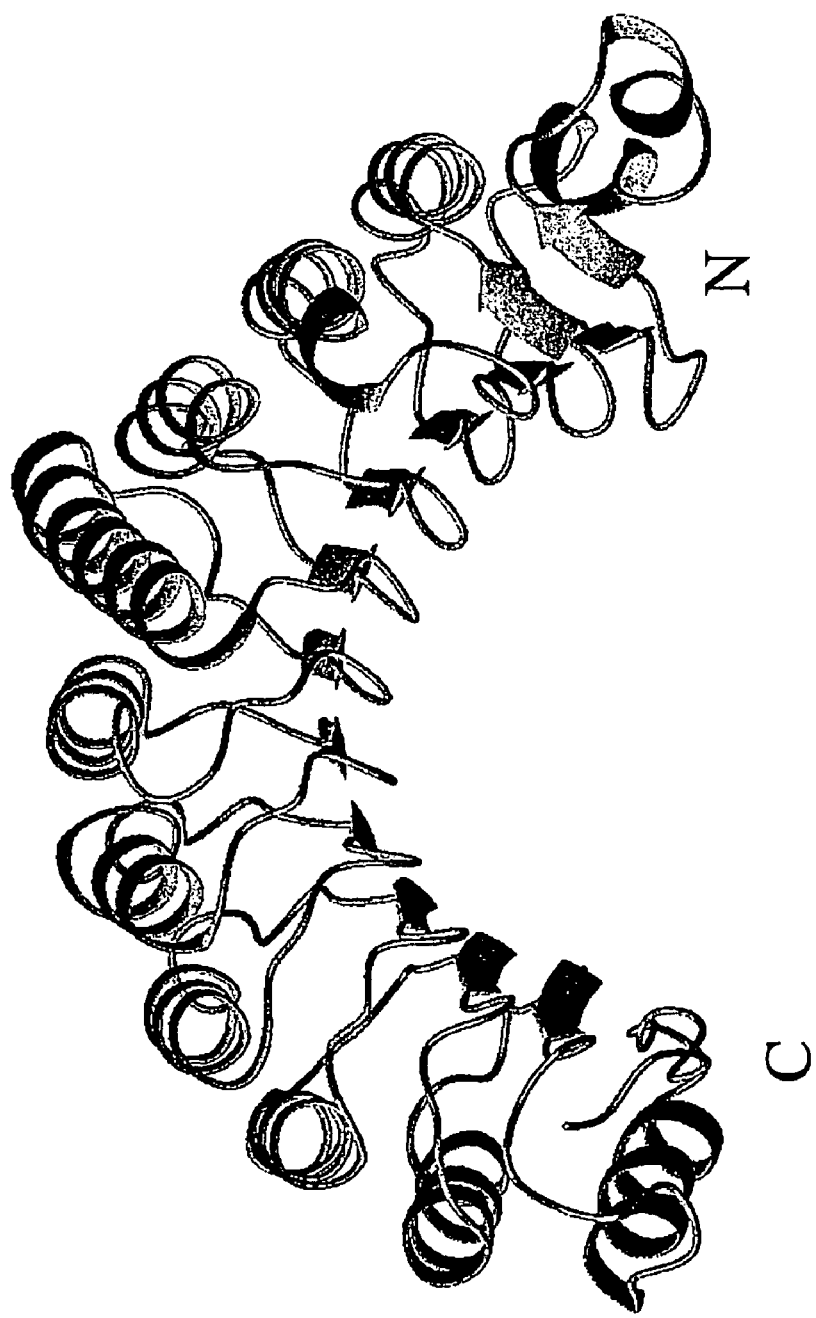
Figure 2E:
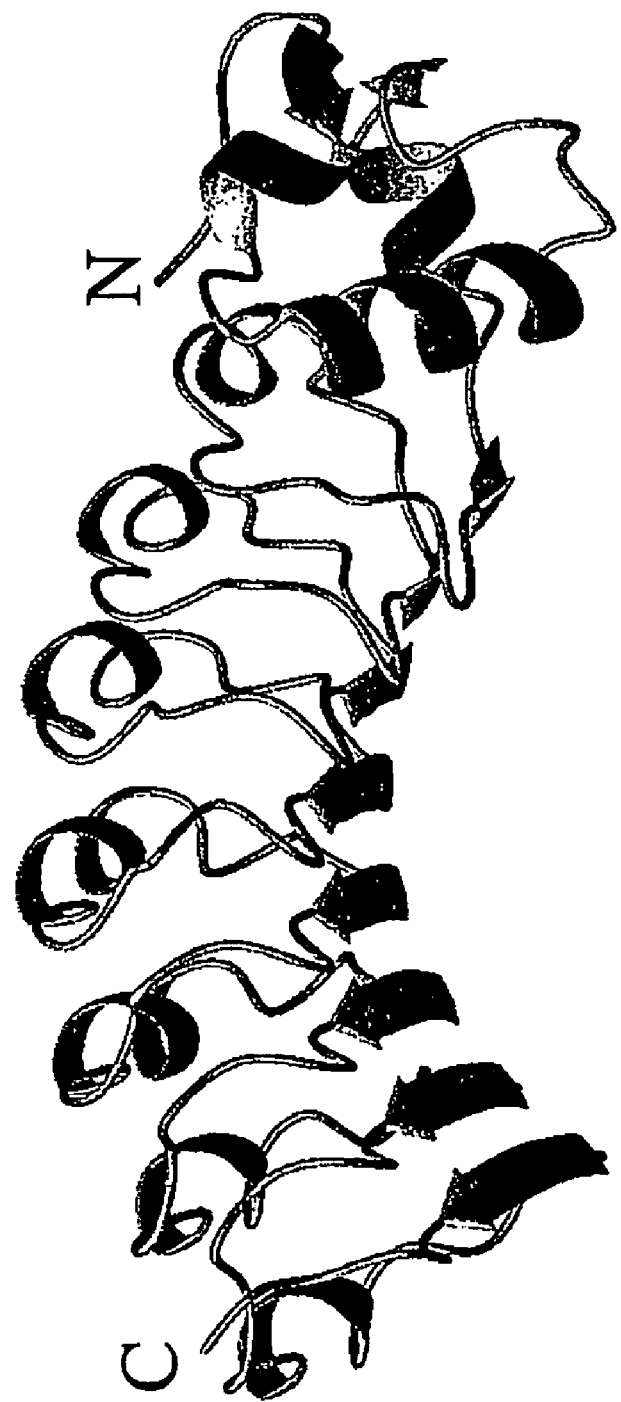
Figure 2F:
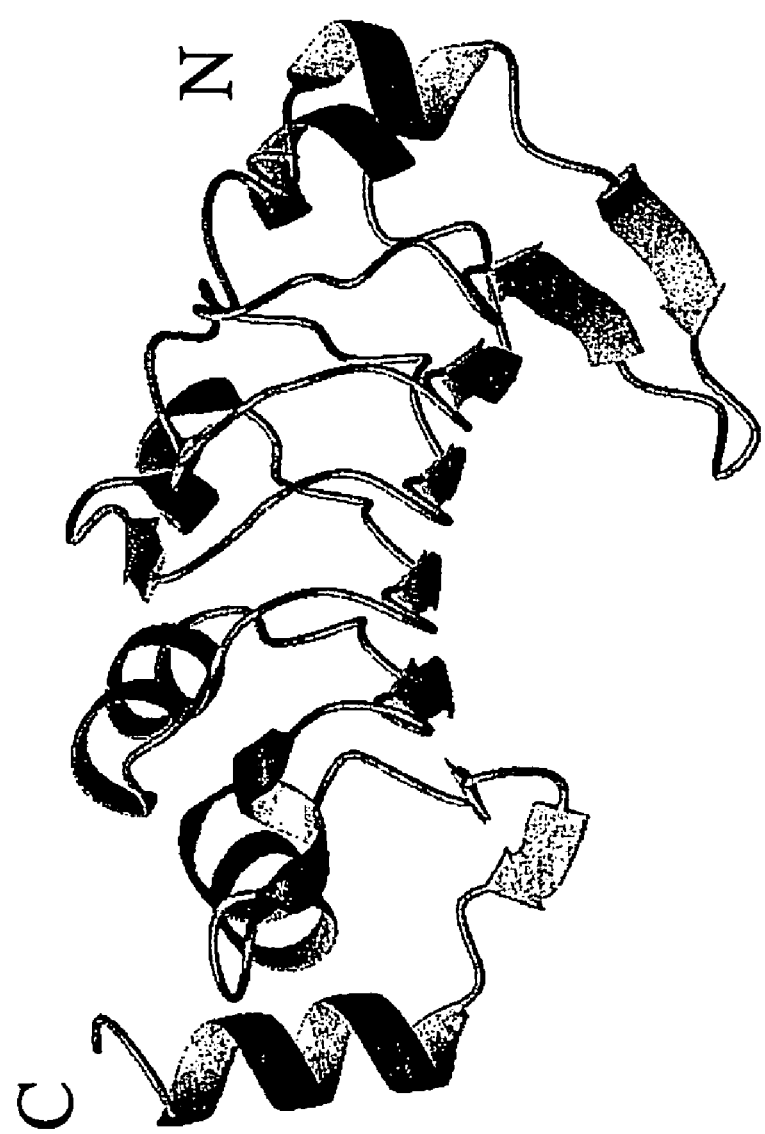
Figure 2G:
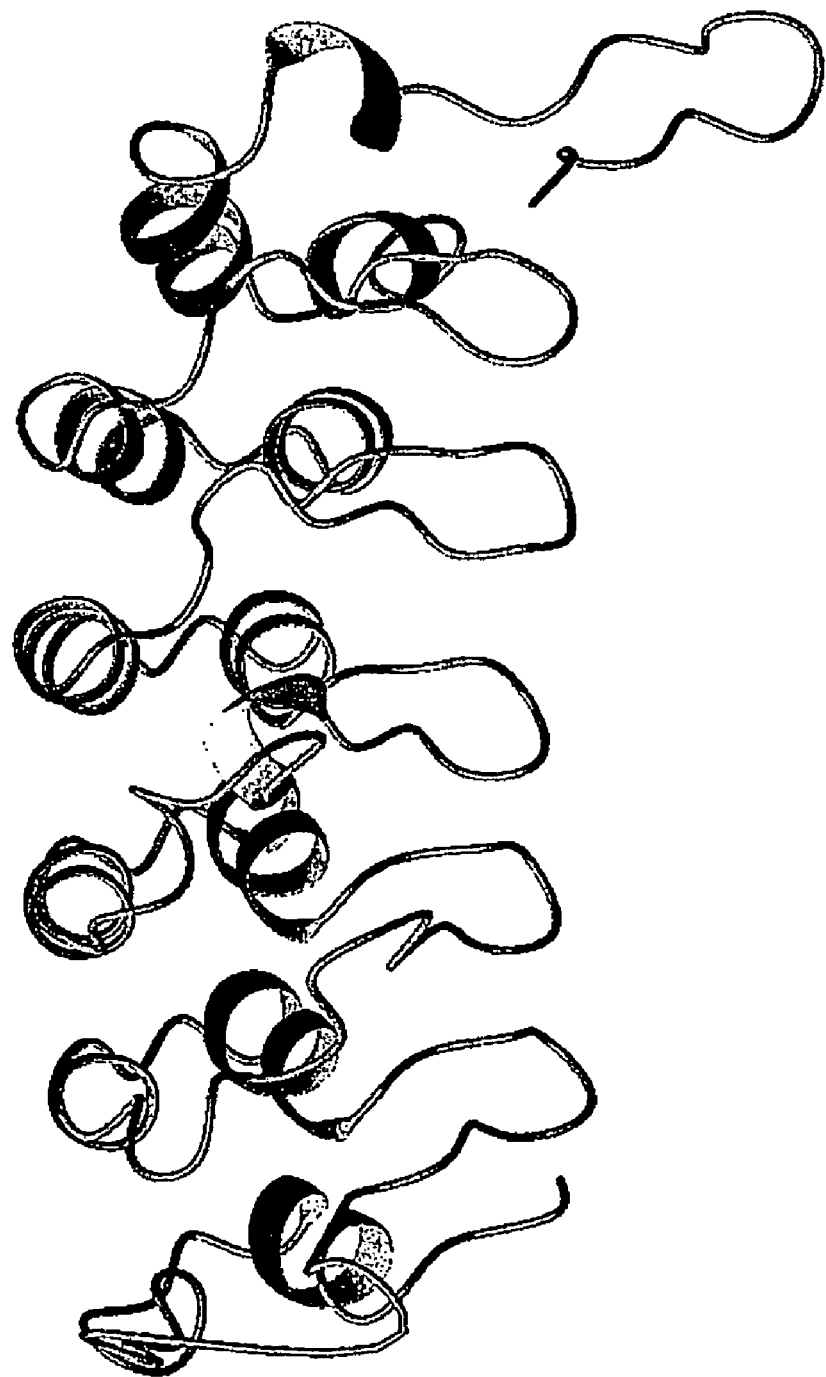
Figure 2H:
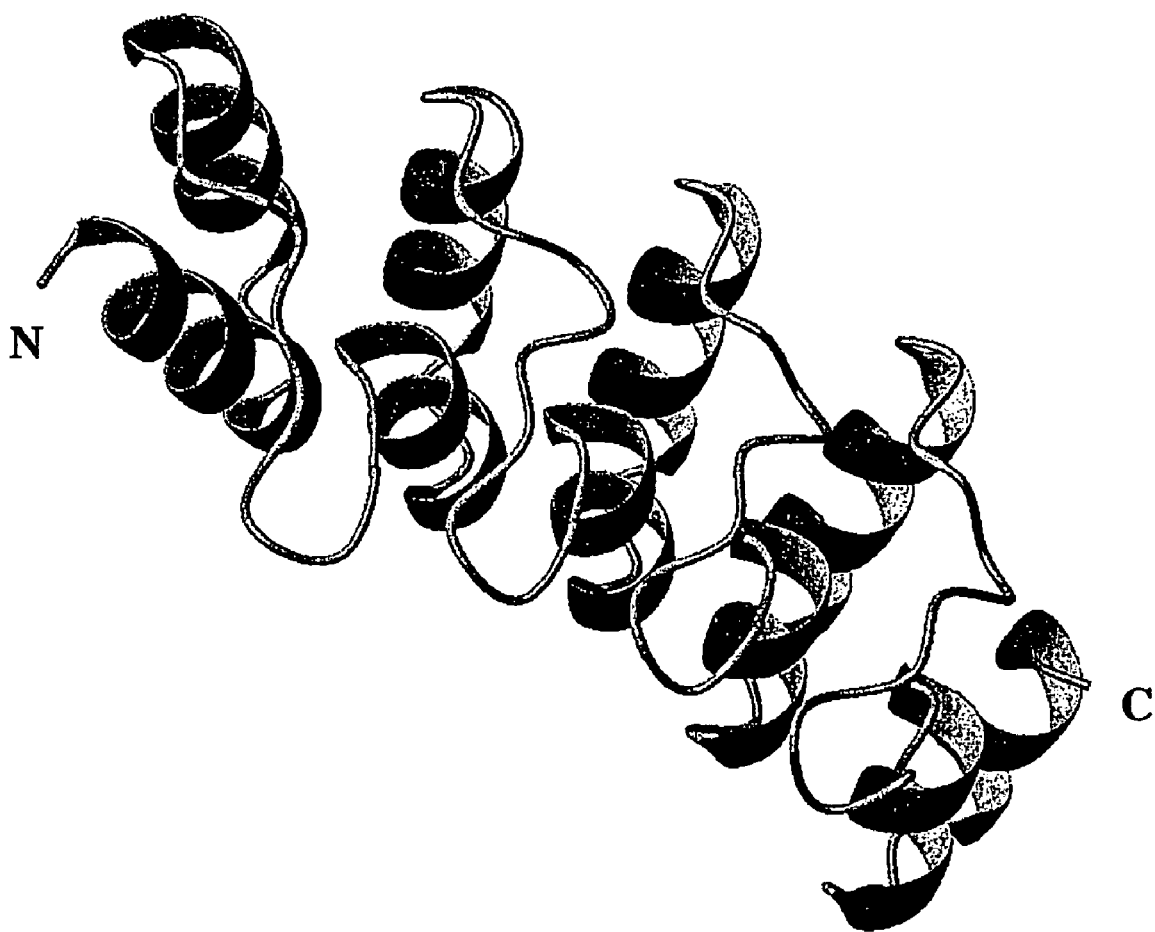

LRR proteins have been identified by their highly conserved consensus of leucine or other hydrophobic residues at positions 2, 5, 7, and 12 (FIG. 4b). However, the significance of this amino acid distribution pattern was only understood, when the first structure of an LRR, the ribonuclease inhibitor protein was solved (FIG. 2c). Recently, further LRR crystal structures have been elucidated (FIGS. 2d-2f). A structure of a typical ankyrin repeat domain protein is shown for comparison (FIG. 2g). A single LRR is postulated to always correspond to a β-strand and an antiparallel α-helix (a unique α/β fold, FIG. 4a), surrounding a core made up from leucine or other aliphatic residues only (Kajava, 1998). The overall shape of ribonuclease inhibitor (RI), a LRR protein, could be described as a horseshoe (FIG. 2c) formed by 15 tandem homologous repeats of strictly alternating A-type (29 amino acids) and B-type (28 amino acids) LRR. The alternating nature of the protein was already recognised when the sequence was analysed (FIG. 5a, (Lee et al., 1988)).

Interestingly, mammalian RI are characterised by their extreme affinity to their target proteins. For the binding of RNase A to human RI a $K_i=5.9\times10^{-14}$ M (Kobe and Deisenhofer, 1996) was reported, whereas angiogenin was found to be inhibited with $K_i=7.1\times10^{-16}$ M by pig RI (Lee et al., 1989), thus becoming one of the strongest interaction known between proteins. Even the best-binding antibodies feature affinities only up $1.5\times10^{-11}$M (Yang et al., 1995). To better understand the outstanding affinity, two RI were co-crystallised with their target proteins. Subsequent analysis of the crystal structures showed that the interactions are mainly electrostatic (Kobe and Deisenhofer, 1996) and the involved amino acids were predominantly found emanating from the inner β-sheet and the loop connecting each unit to its α-helix (FIG. 4b, Kobe and Deisenhofer, 1995). Moreover, the width of the horseshoe-like fold can change slightly to accommodate the target protein (Kobe and Deisenhofer, 1994). The interface between target and inhibitor consists of a "patchwork" of interactions and the tight association originates from the large buried surface area (about 2550 $A^2$) when the target protein is bound inside the horseshoe, rather than shape complementarity (Kobe and Deisenhofer, 1996).

When comparing the detailed binding of RNase A and angiogenin (two molecules with only 30% sequence identity) to RI, significant differences became apparent (Chen and Shapiro, 1997). Whereas largely the same residues were involved on the side of RI, the residues of the target protein were not homologous or used different types of bonding (Papageorgiou et al., 1997). In other words, RI evolved in a way which allowed it to bind and inhibit different target molecules by relying on a large number of contacts presented in correct geometrical orientation, rather than optimal complementarity of the residues. This is the basis for a design of new binding molecules, which will have new binding specificities. The shape seems to be predestined for the recognition of large surfaces thereby allowing a much greater variety of random amino acids to generate a library as compared to the relatively small "variable" domains of antibodies. However, the loops of antibodies seem to be superior if small haptens or deep clefts have to be recognised. In addition, not only the repeats themselves can be varied but also their number depending on the target molecules.

Further preferred is a collection, wherein each of said modules comprises the LRR consensus sequence xLxxLxLxxN±xaxx±a±±±±a±±a±±x±±(SEQ ID NO: 5), wherein "x" denotes any amino acid, "a" denotes an aliphatic amino acid, and "±" denotes any amino acid or a deletion.

The term "aliphatic amino acid" refers to an amino acid taken from the list of Ala, Gly, Ile, Leu and Val.

Particularly preferred is a collection, wherein at least one of said modules comprises the LRR consensus sequence XLExLxLxxCxLTxxxCxxLxxaLxxxx (SEQ ID NO: 6), wherein "x" denotes any amino acid, and "a" denotes an aliphatic amino acid (A-type LRR).

Particularly preferred is furthermore a collection, wherein at least one of said modules comprises the LRR consensus sequence XLxELxLxxNxLGDxGaxxLxxxLxxPxx (SEQ ID NO: 7), wherein "x" denotes any amino acid, and "a" denotes an aliphatic amino acid (B-type LRR).

Most preferred is a collection, wherein one or more of the positions denoted "x" and/or "±" are randomised.

Further preferred is a collection, wherein the cysteine residue at position 10 in the A-type LRR consensus sequence is replaced by a hydrophilic amino acid residue, and wherein the cystein residue at position 17 is replaced by a hydrophobic amino acid residue.

A hydrophilic amino acid residue may be taken from the list of Ser, Thr, Tyr, Gln, and Asn.

A hydrophobic amino acid residue may be taken from the list of Ala, Ile, Leu, Met, Phe, Trp, and Val.

Compared to single-chain Fv or conventional antibodies, several advantages can be enumerated. Whereas disulfide bridges are crucial for the stability of most antibodies (Proba et al., 1997), no disulfide bonds are required in LRR proteins, which makes intracellular applications possible.

Therefore, new binding molecules can be generated for application in a reducing environment. This could become an enormously powerful tool in elucidating the function of the numerous proteins identified by the genome sequencing projects by direct inhibition in the cytosol. As for many applications in biotechnology large amounts of expressed and correctly folding proteins are required, a production in *E. coli* is preferable but very difficult for antibodies which evolved in the oxidising extracellular environment. In contrast, folding or refolding of RI variants are more efficient as they are naturally found in the cytosol (see Example 1).

In a further preferred embodiment of a collection according to the present invention, one or more of the amino acid residues in an ankyrin or LRR repeat module as described above are exchanged by an amino acid residue found at the corresponding position in a corresponding naturally occurring repeat unit.

Preferably, up to 30% of the amino acid residues are exchanged, more preferably, up to 20%, and most preferably, up to 10% of the amino acid residues are exchanged.

Particularly preferred is a collection, wherein said set consists of one type of repeat modules.

The term "type of repeat module" refers to the characteristics of a module determined by the length of the module, the number and composition of its "fixed positions" as well as of its "randomised positions". "Different types of modules" may differ in one or more of said characteristics.

Further preferred is a collection, wherein said set consists of two different types of repeat modules.

In a still further preferred embodiment, the present invention relates to a collection, wherein said set comprises two different types of consecutive repeat modules as pairs in said repeat proteins.

Most preferred is a collection, wherein said two different types of modules are based on said A-type LRR and B-type LRR.

Further preferred is a collection, wherein the amino acid sequences of the repeat modules comprised in said set are identical for each said type except for the randomised residues.

Yet further preferred is a collection, wherein the nucleic acid sequences encoding the copies of each said type are identical except for the codons encoding amino acid residues at positions being randomised.

Particularly preferred is a collection, wherein the nucleic acid molecules encoding said repeat proteins comprise identical nucleic acid sequences of at least 9 nucleotides between said repeat modules.

Said "identical nucleic acid sequences of at least 9 nucleotides" may be part of the end of only one repeat module, or be formed by the ends of two adjacent repeat modules, or may be part of a (poly)peptide linker connecting two repeat modules.

In a further preferred collection according to the present invention, the nucleic acid molecules encoding said repeat proteins comprise identical nucleic acid sequences of at least 9 nucleotides between said pairs.

Said "identical nucleic acid sequences of at least 9 nucleotides" may be part of the end of only one pair of repeat modules, or be formed by the ends of two adjacent pairs of repeat modules, or may be part of a (poly)peptide linker connecting two pairs of repeat modules.

Most preferable is a collection, wherein each of the nucleic acid sequences between said modules, or said pairs, comprises a restriction enzyme recognition sequence. The term "restriction enzyme recognition sequence" refers to a nucleic acid sequence being recognised and cleaved by a restriction endonuclease. Said restriction enzyme recognition sequence may be divided symmetrically between the 3' and 5' ends (e.g. 3 nucleotides of a 6 base pair recognition sequence on both ends), or non-symmetrically (e.g. 2 nucleotides on one end, 4 on the corresponding end).

Particularly preferred is a collection, wherein each of the nucleic acid sequences between said modules, or said pairs, comprises a nucleic acid sequence formed from cohesive ends created by two compatible restriction enzymes.

The term "compatible restriction enzymes" refers to restriction enzymes having different recognition sequences but forming compatible cohesive ends when cleaving double stranded DNA. After re-ligation of sticky-end double-stranded DNA fragments produced from two compatible restriction enzymes, the product DNA does no longer exhibit the recognition sequences of both restriction enzymes.

In a further most preferred embodiment of the collection of the present invention, said identical nucleic acid sequences allow a PCR-based assembly of the nucleic acid molecules encoding said repeat proteins.

In a most preferred embodiment of the collection according to the present invention, said repeat proteins comprise one or more pairs of modules based on said A-type LRR and B-type LRR, wherein each of said pairs has the sequence

RLE1L1L112DLTEAG4KDLASVLRSNPSLREL3LS
3NKLGDAGVRLLLQGLLDPGT (SEQ ID NO: 8), wherein 1 represents an amino acid residue selected from the group:
D, E, N, Q, S, R, K, W and Y;

wherein 2 represents an amino acid residue selected from the group:
N, S and T;

wherein 3 represents an amino acid residue selected from the group:
G, S, D, N, H and T; and wherein 4 represents an amino acid residue selected from the group:
L, V and M.

Most preferably, each of said pairs of modules is encoded by the nucleic acid molecule

```
CGC CTG GAG 111 CTG 111 CTG 111 111 222 GAG CTC
ACC GAG GCC GGC 444 AAG GAC CTG GCC AGC GTG CTC
CGC TCC AAC CCG AGC CTG CGG GAG CTG 333 CTG AGC
333 AAC AAG CTC GGC GAT GCA GGC GTG CGG CTG CTC
TTG CAG GGG CTG CTG GAC CCC GGC ACG (SEQ ID NO: 9)
``` wherein 111 represents a codon encoding an amino acid residue selected from the group:
D, E, N, Q, S, R, K, W and Y;

wherein 222 represents a codon encoding an amino acid residue selected from the group:
N, S and T;

wherein 333 represents a codon encoding an amino acid residue selected from the group:
G, S, D, N, H and T; and wherein 444 represents a codon encoding an amino acid residue selected from the group:
L, V and M.

In another preferred embodiment one or more of the amino acid residues in at least one pair of modules as listed above are exchanged by an amino acid residue found at the corresponding position in a naturally occurring LRR.

In yet another preferred embodiment, one or more of the amino acid codons in at least one pair of modules as listed above are exchanged by a codon encoding an amino acid residue found at the corresponding position in a naturally occurring LRR. Preferably, up to 30% of the amino acid residues, or amino acid codons, respectively, are exchanged, more preferably, up to 20%, and most preferably, up to 10% are exchanged.

In yet another preferred embodiment, one or more of the amino acid codons in at least one pair of modules as listed above are exchanged by a codon encoding an amino acid residue found at the corresponding position in a naturally occurring LRR.

In a further preferred embodiment, the present invention relates to a collection of recombinant nucleic acid molecules comprising a collection of nucleic acid molecules according to the present invention.

In the context of the present invention, the term "recombinant nucleic acid molecule" refers to a RNA or DNA molecule which comprises a nucleic acid sequence encoding said repeat protein and further nucleic acid sequences, e.g. non-coding sequences.

In a still further preferred embodiment, the present invention relates to a collection of vectors comprising a collection of nucleic acid molecules according to the present invention, or a collection of recombinant nucleic acid molecules according to the present invention.

A vector according to the present invention may be a plasmid, phagemid, cosmid, or a virus- or bacteriophage-based vector, and may be a cloning or sequencing vector, or preferably an expression vector, which comprises all elements required for the expression of nucleic acid molecules from said vector, either in prokaryotic or eukaryotc expression systems. Vectors for cloning, sequencing and expressing nucleic acid molecules are well known to any one of ordinary skill in the art. The vectors containing the nucleic acid molecules of the invention can be transferred into the host cell by well-known methods, which vary depending on the type of cellular host. For example, calcium chloride transfection is commonly utilised for prokaryotic cells, whereas, e.g., calcium phosphate or DEAE-Dextran mediated transfection or electroporation may be used for other cellular hosts; see Sambrook et al. (1989). Such vectors may comprise further genes such as marker genes which allow for the selection of said vector in a suitable host cell and under suitable conditions. Preferably, the nucleic acid molecules of the invention are operatively linked to expression control sequences allowing expression in prokaryotic or eukaryotic cells. Expression of said nucleic acid molecules comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and, optionally, a poly-A signal ensuring termination of transcription and stabilization of the transcript, and/or an intron further enhancing expression of said nucleic acid molecule. Additional regulatory elements may include transcriptional as well as translational enhancers, and/or naturally-associated or heterologous promoter regions. Possible regulatory elements permitting expression in prokaryotic host cells comprise, e.g., the pL, lac, trp or tac promoter in E. coli, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription, such regulatory elements may also comprise transcription termination signals, such as the SV40-poly-A site or the tk-poly-A site, downstream of the nucleic acid molecule. Furthermore, depending on the expression system used leader sequences capable of directing the (poly)peptide to a cellular compartment or secreting it into the medium may be added to the coding sequence of the nucleic acid molecule of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL) or pCI (Promega) or more preferably pTFT74 (Ge et al., 1995) or a member of the pQE series (Qiagen). Furthermore, the present invention relates to vectors, particularly plasmids, cosmids, viruses and bacteriophages used conventionally in genetic engineering that comprise the polynucleotide of the invention. Preferably, said vector is an expression vector. Methods which are well known to those skilled in the art can be used to construct recombinant viral vectors; see, for example, the techniques described in Sambrook et al., Molecular Cloning A Laboratory Manual, Cold Spring Harbor Laboratory (1989) N.Y. and Ausubel et al., Current Protocols in Molecular Biology, Green Publishing Associates and Wiley Interscience, N.Y. (1989).

Futhermore, the invention relates to a collection of host cells comprising a collection of nucleic acid molecules according to the present invention, a collection of recombinant nucleic acid molecules according to the present invention, or a collection of vectors according to the present invention.

In the context of the present invention the term "host cell" may be any of a number commonly used in the production of heterologous proteins, including but not limited to bacteria, such as *Escherichia coli* (Ge et al., 1995), or *Bacillus subtilis* (Wu et al., 1993a), fungi, such as yeasts (Horwitz et al., 1988; Ridder et al., 1995) or filamentous fungus (Nyyssönen et al., 1993), plant cells (Hiatt, 1990; Hiatt and Ma, 1993; Whitelam et al., 1994), insect cells (Potter et al., 1993; Ward et al., 1995), or mammalian cells (Trill et al., 1995).

In another embodiment, the present invention relates to a collection of repeat proteins encoded by a collection of nucleic acid molecules according to the present invention, by a collection of vectors according to the present invention, or produced by a collection of host cells according to the present invention.

Furthermore, the present invention relates to a method for the construction of a collection of nucleic acid molecules according to the present invention, comprising the steps of
   (a) identifying a repeat unit from a repeat protein family;
   (b) identifying framework residues and target interaction residues in said repeat unit;
   (c) deducing at least one type of repeat module comprising framework residues and randomised target interaction residues from at least one member of said repeat protein family; and
   (d) constructing nucleic acid molecules each encoding a repeat protein comprising two or more copies of said at least one type of repeat module deduced in step (c).

The modes how this method is to be carried out are explained above in connection with the embodiment of the collection of nucleic acid molecules of the present invention. Descriptions of two such modes are illustrated in the example.

In a preferred embodiment of this method, said at least one repeat module deduced in step (c) has an amino acid sequence, wherein at least 70% of the amino acid residues correspond either
  (i) to consensus amino acid residues deduced from the amino acid residues found at the corresponding positions of at least two naturally occurring repeat units; or
  (ii) to the amino acid residues found at the corresponding positions in a naturally occurring repeat unit.

Further preferred is a method for the production of a collection of poly)peptides/proteins according to the present invention, comprising the steps of
  (a) providing a collection of host cells according to the present invention; and
  (b) expressing the collection of nucleic acid molecules comprised in said host cells.

Particularly preferred is a method for obtaining a repeat protein having a predetermined property, comprising the steps of
  (a) providing a collection of repeat proteins according to the present invention; and
  (b) screening said collection and/or selecting from said collection to obtain at least one repeat protein having said predetermined property.

The diverse collection of repeat proteins may be provided by several methods in accordance with the screening and/or selection system being used, and may comprise the use of methods such as display on the surface of bacteriophages (WO 90/02809; Smith, 1985; Kay et al., 1996; Dunn, 1996) or bacterial cells (WO 93/10214), ribosomal display (WO 91/05058; WO 98/48008; Hanes et al., 1998), display on plasmids (WO 93/08278) or by using covalent RNA-repeat protein hybrid constructs (WO 00/32823), intracellular expression and selection/screening such as by protein complementation assay (WO 98/341120; Pelletier et al., 1998). In all these methods, the repeat proteins are provided by expression of a corresponding collection of nucleic acid molecules and subsequent screening of the repeat proteins followed by identification of one or more repeat proteins having the desired property via the genetic information connected to the repeat proteins.

In the context of the present invention the term "predetermined property" refers to a property, which one of the repeat proteins out of the collection of repeat proteins should have, and which forms the basis for screening and/or selecting the collection. Such properties comprise properties such as binding to a target, blocking of a target, activation of a target-mediated reaction, enzymatic activity, and further properties, which are known to one of ordinary skill. Depending on the type of desired property, one of ordinary skill will be able to identify format and necessary steps for performing screening and/or selection.

Most preferably, the present invention relates to a method, wherein said predetermined property is binding to a target.

In another embodiment, the invention relates to a repeat protein from a collection according to the present invention. Preferably said repeat protein has been obtained by the above-described method and has one of the predetermined properties.

Furthermore, the present invention relates to a nucleic acid molecule encoding the repeat protein according to the present invention.

In yet another embodiment, the present invention relates to a vector containing the nucleic acid molecule according to the present invention.

The present invention relates also to pharmaceutical compositions comprising a repeat protein from a collection of the present invention or a nucleic acid molecule encoding said repeat protein, and optionally a pharmaceutically acceptable carrier and/or diluent.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg (or of nucleic acid for expression or for inhibition of expression in this range); however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins or interferons depending on the intended use of the pharmaceutical composition.

The repeat proteins comprised in the pharmaceutical compositions of the present invention can comprise a further domain, said domain being linked by covalent or non-covalent bonds. The linkage can be based on genetic fusion according to the methods known in the art and described above or can be performed by, e.g., chemical cross-linking as described in, e.g., WO 94/04686. The additional domain present in the fusion protein comprising the peptide, polypeptide or antibody employed in accordance with the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the repeat protein or vice versa. The above described fusion protein may further comprise a cleavable linker or cleavage site for proteinases. Furthermore, said further domain may be of a predefined specificity or function. In this context, it is understood that the repeat proteins present in the pharmaceutical composition according to the invention may be further modified by conventional methods known in the art. This allows for the construction of fusion proteins comprising the repeat protein of the invention and other functional amino acid sequences, e.g., nuclear localization signals, transactivating domains, DNA-binding domains, hormone-binding domains, protein tags (GST, GFP, h-myc peptide, FLAG, HA peptide) which may be derived from heterologous proteins. Thus, administration of the composition of the invention can utilize unlabeled as well as labeled (poly)peptides or antibodies.

Further preferred is a nucleic acid molecule encoding a pair of repeat modules for the construction of a collection according to the present invention, wherein said nucleic acid molecule is:

```
                                                    (SEQ ID NO: 10)
CGC CTG GAG 111 CTG 111 CTG 111 111 222 GAC CTC ACC GAG GCC GGC

444 AAG GAC CTG GCC AGC GTG CTC CGC TCC AAC CCG AGC CTG CGG

GAG CTG 333 CTG AGC 333 AAC AAG CTC GGC GAT GCA GGC GTG CGG

CTG CTC TTG CAG GGG CTG CTG GAC CCC GGC ACG,
``` wherein 111 represents a codon encoding an amino acid residue selected from the group:

D, E, N, Q, S, R, K, W and Y;

wherein 222 represents a codon encoding an amino acid residue selected from the group:

N, S and T;

wherein 333 represents a codon encoding an amino acid residue selected from the group:

G, S, D, N, H and T; and wherein 444 represents a codon encoding an amino acid residue selected from the group:

L, V and M.

These and other embodiments are disclosed and encompassed by the description and examples of the present invention. Further literature concerning any one of the methods, uses and compounds to be employed in accordance with the present invention may be retrieved from public libraries, using for example electronic devices. For example database "PubMed" (Sequeira et al., 2001) may be utilised which is available on the Internet.

An overview of patent information in biotechnology and a survey or relevant sources of patent information useful for retrospective searching and for current awareness is given in Berks, (1994).

FIGURES

FIG. 1. Schematic representation of the terms "Repeat Protein", "Repeat Domains", "Non-repeat Domain", "Repeat Module", "Capping Modules", and "Linker".

FIG. 2*a*. Examples of leucine-rich repeat proteins featuring only a repeat domain (1A4Y) or both a repeat domain and a non-repeat domain (1D0B).

FIG. 2*b*. Examples of ankyrin repeat proteins featuring only a repeat domain (1AWC) or both a repeat domain and a non-repeat domain (1DCQ).

FIG. 2*c*. Crystal Structure of the Pig Liver Ribonuclease Inhibitor (Kobe and Deisenhofer, 1993).

FIG. 2*d*. Crystal Structure of the Yeast ma1p GTPase-activating Protein (Hillig et al., 1999).

FIG. 2*e*. Crystal Structure of the Listeria InIB Protein (Marino et al., 1999).

FIG. 2*f*. Crystal Structure of the Human Spliceosomal Protein U2A' (Price et al., 1998).

FIG. 2*g*. Crystal Structure of the Human Transcription Factor Inhibitor IκBα (Huxford et al., 1998).

FIG. 2*h*. X-ray structure of the ankyrin repeat domain of the mouse GA-binding protein beta 1 subunit [pdb entry 1AWC (Batchelor et al., 1998)]. The N- and C-termini of the domain are labeled. This image has been created using MOLMOL (Koradi et al., 1996).

FIG. 3. Examples of naturally occurring repeat units and capping units. A leucine-rich repeat protein (1A4Y) and an ankyrin repeat protein (1AWC) are shown.

FIG. 4*a*. β/α-Fold of the LRR unit from Pig Ribonuclease Inhibitor (Residue 423 to 450).

FIG. 4*b*. Leucines and Positions of Amino Acids Emanating from the β-strand of a LRR unit from Pig Ribonuclease Inhibitor (Residue 86 to 112).

FIG. 4*c*. Structural description of an ankyrin repeat unit. A: Sideview. B: Topview. Interacting residues are depicted as "balls and sticks". These pictures were made using the third repeat of the GA-binding protein (pdb entry 1AWC; Batchelor et al., 1998) displayed with MOLMOL (Koradi et al., 1996).

FIG. 4*d*. A subset of the framework residues of a LRR unit is shown as "ball and sticks". The numbering refers to the positions within a LRR unit.

FIG. 4*e*. A subset of the target interaction residues of a LRR unit is shown as "ball and sticks". The numbering refers to the positions within a LRR unit.

FIG. 4*f*. A model of a LRR repeat module pair is shown. The numbering refers to the positions within the derived LRR repeat motif pair.

FIG. 5*a*. Internal Amino Acid Alignment of Human Placental Ribonuclease Inhibitor (SEQ ID NO: 53)

FIG. 5*b*. Consensus (SEQ ID NO: 8) Defined on the Basis of all Ribonuclease Inhibitor Sequences FIG. 5*c*: Statistical analysis of the most frequent amino acids (SEQ ID NOS 54-57, respectively in order of appearance) at one positions in the A-type repeat units of mammalian RI. The sequences of the A-type repeat units of individual RIs are each presented in a box of 7 times 28 amino acids, since a preliminary analysis indicates that each RI possesses seven A-type repeat units having each a lenath of 28 amino acids.

FIG. 5*d*: Statistical analysis of the most frequent amino acids (SEQ ID NOS 58-61, respectively in order of appearance) at one positions in the B-type repeat units of mammalian RI. The sequences of B-type repeat units of individual RIs are each presented in a box of 7 times 29 amino acids, since a preliminary analysis indicates that each RI possesses seven B-type repeat units having each a length of 29 amino acids.

Figure 6:
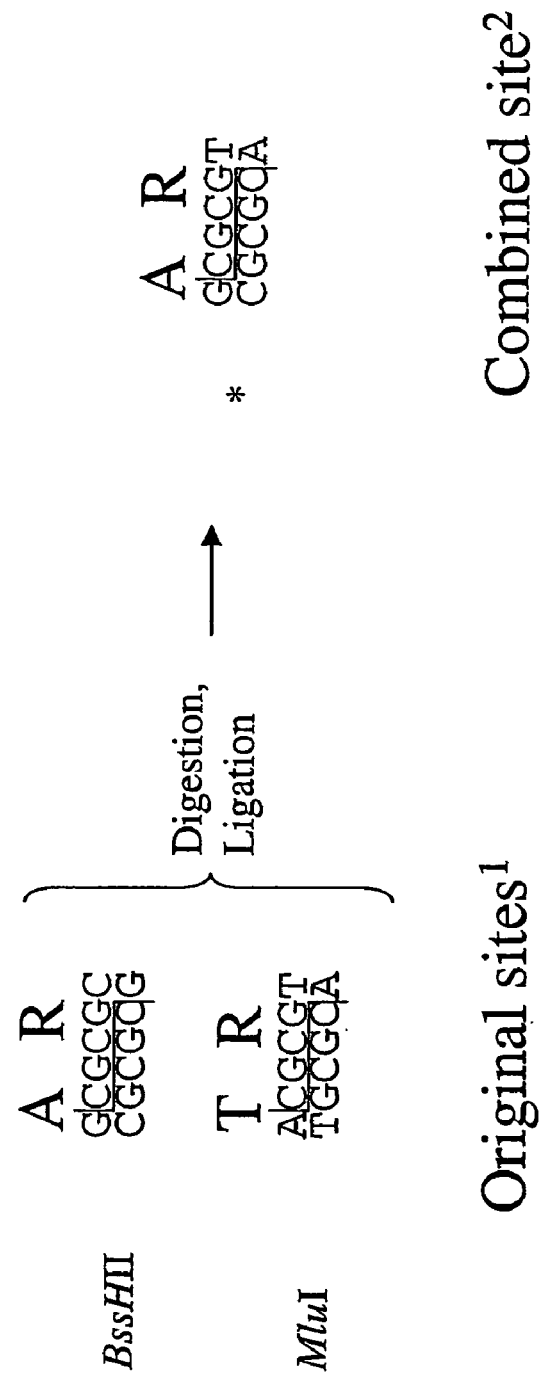

FIG. 6. Restriction Enzyme Recognition Sites and Encoded Amino Acids. The DNA recognized by BssHII codes for alanine and arginine (A and R) in the first reading frame. Accordingly, MluI codes for threonine and arginine (T and R) in the first reading frame. Combination of DNA molecules cut with BssHII and MluI give a new combined site not recognized by either restriction enzyme and coding for alanine and arginine (A and R).

FIG. 7a to 7c. Cloning of the library of repeat modules.

FIG. 8. DNA sequence (SEQ ID NO: 62) and translated amino acids (SEQ ID NO: 63) of the NcoI-HindIII insert in plasmid pTFT_N1CL. The abbreviation pTFT refers to all plasmids derived from pTFT74 (Ge et al., 1995). The abbreviation N1CL refers to an insert containing an N-terminal module, 1 repeat module, a C-terminal module, and a linker sequence.

Figure 9A:
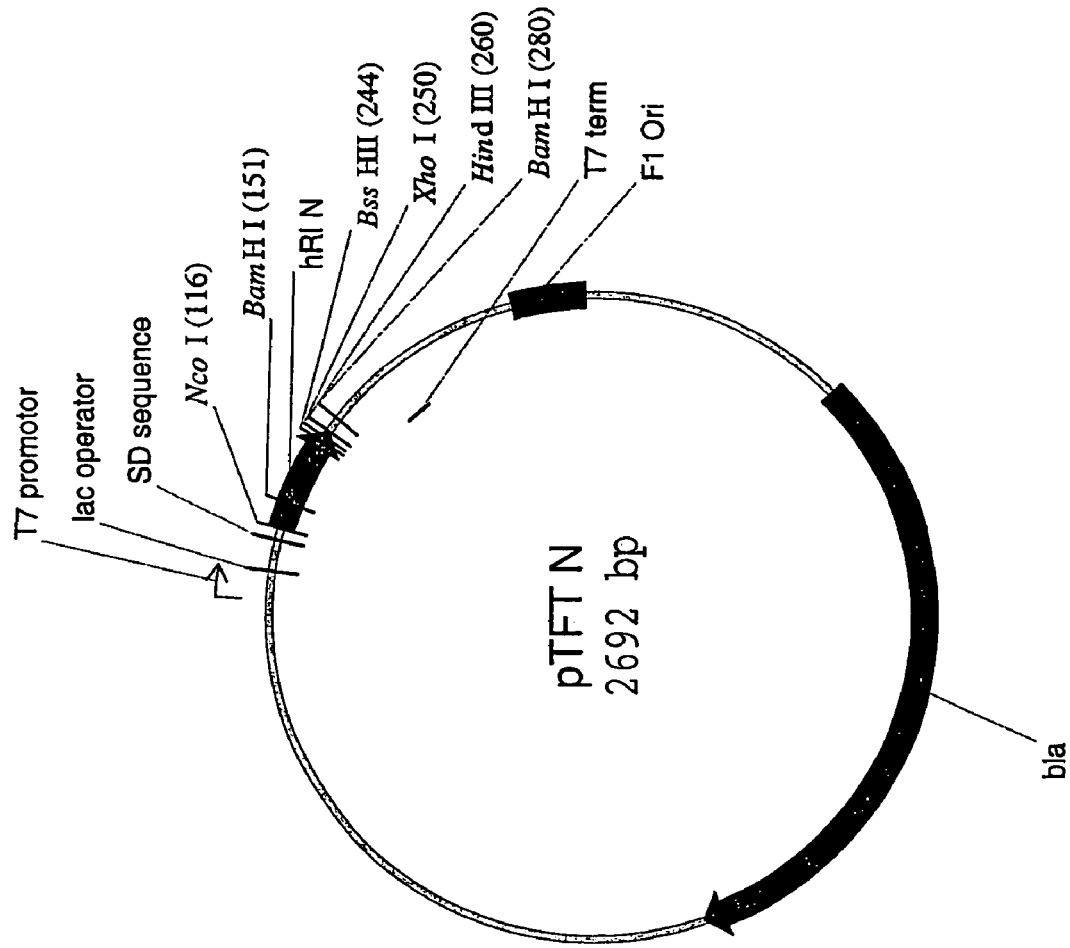
Figure 9B:
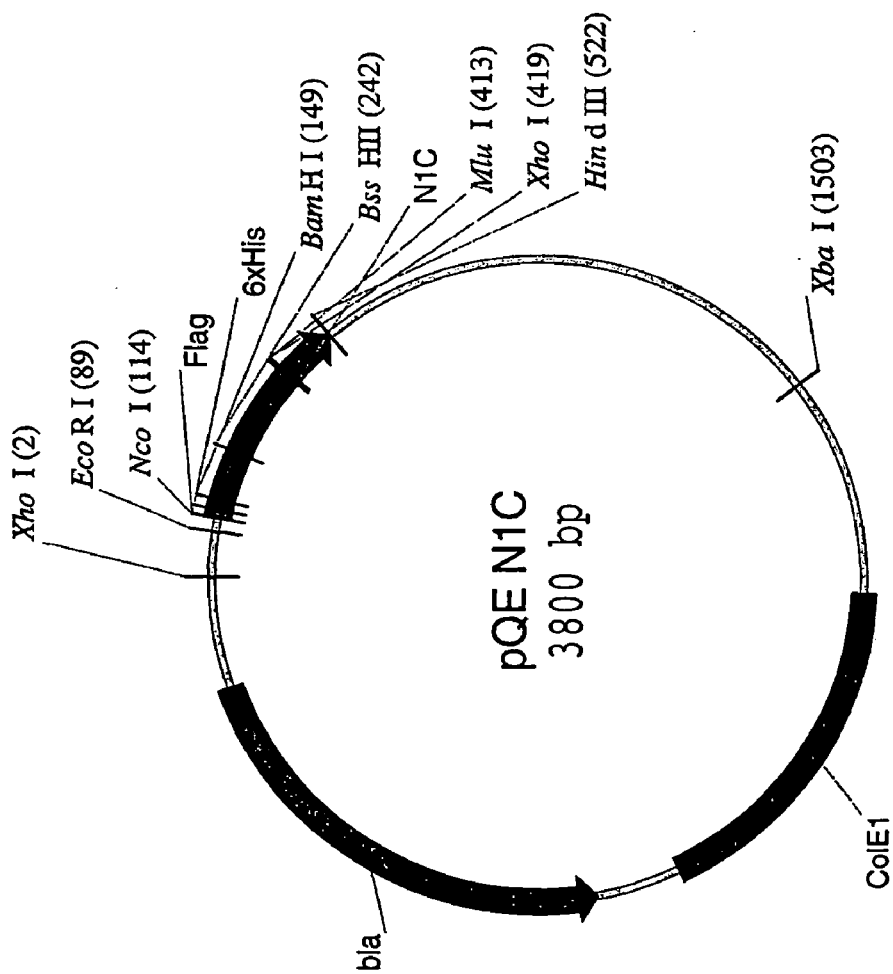
Figure 9C:
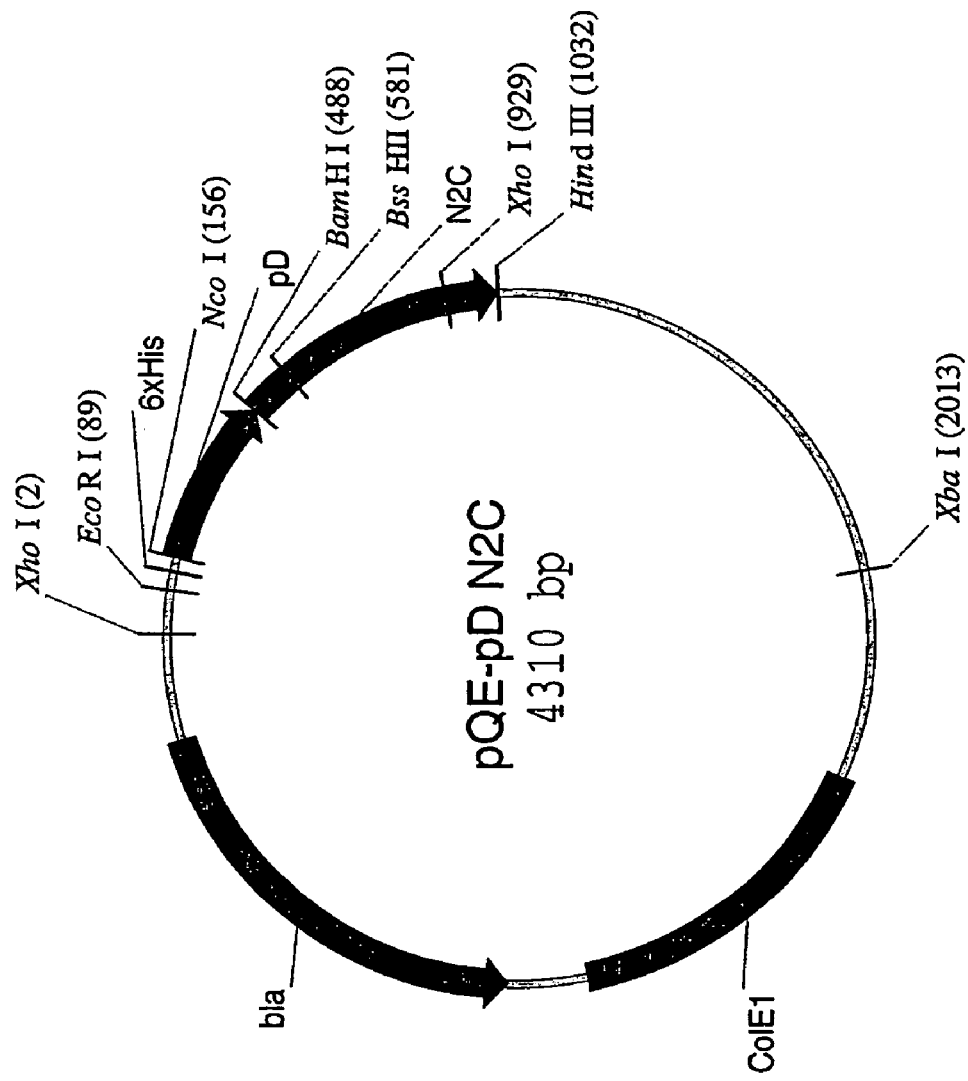

FIG. 9a to 9c. Diagrams of plasmids pTFT_N, pQE_N1C, and pQE-pD_N2C. The nomenclature is as described in the caption of FIG. 8. The name of plasmids derived from pQE30 (Qiagen) always starts with pQE. The abbreviation pD refers to lambda phage protein D (Forrer and Jaussi, 1998).

Figure 10A:
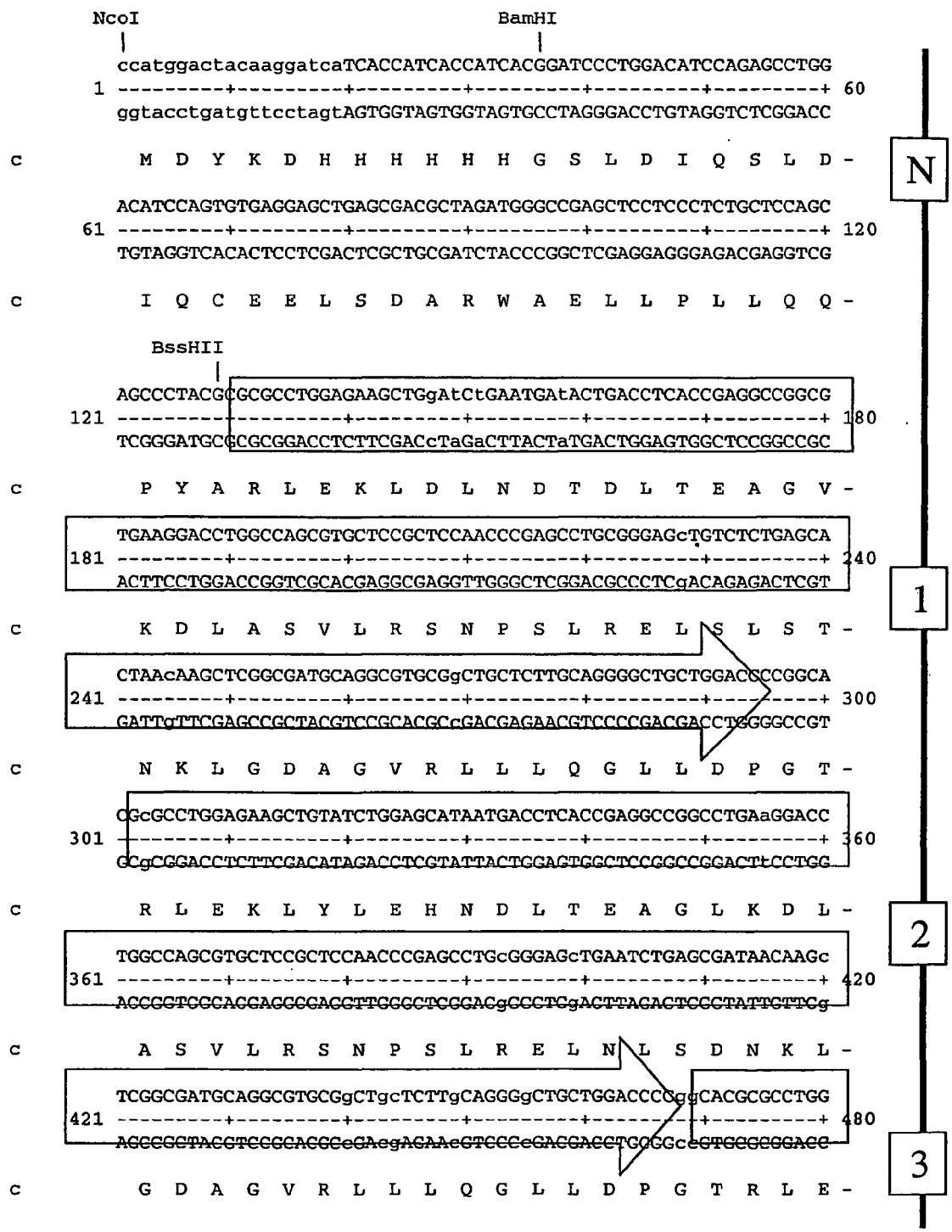

FIGS. 10a and 10b, DNA sequence of the NcoI-HindIII insert of plasmid pQE_N4C clone D17.

Figure 11A:
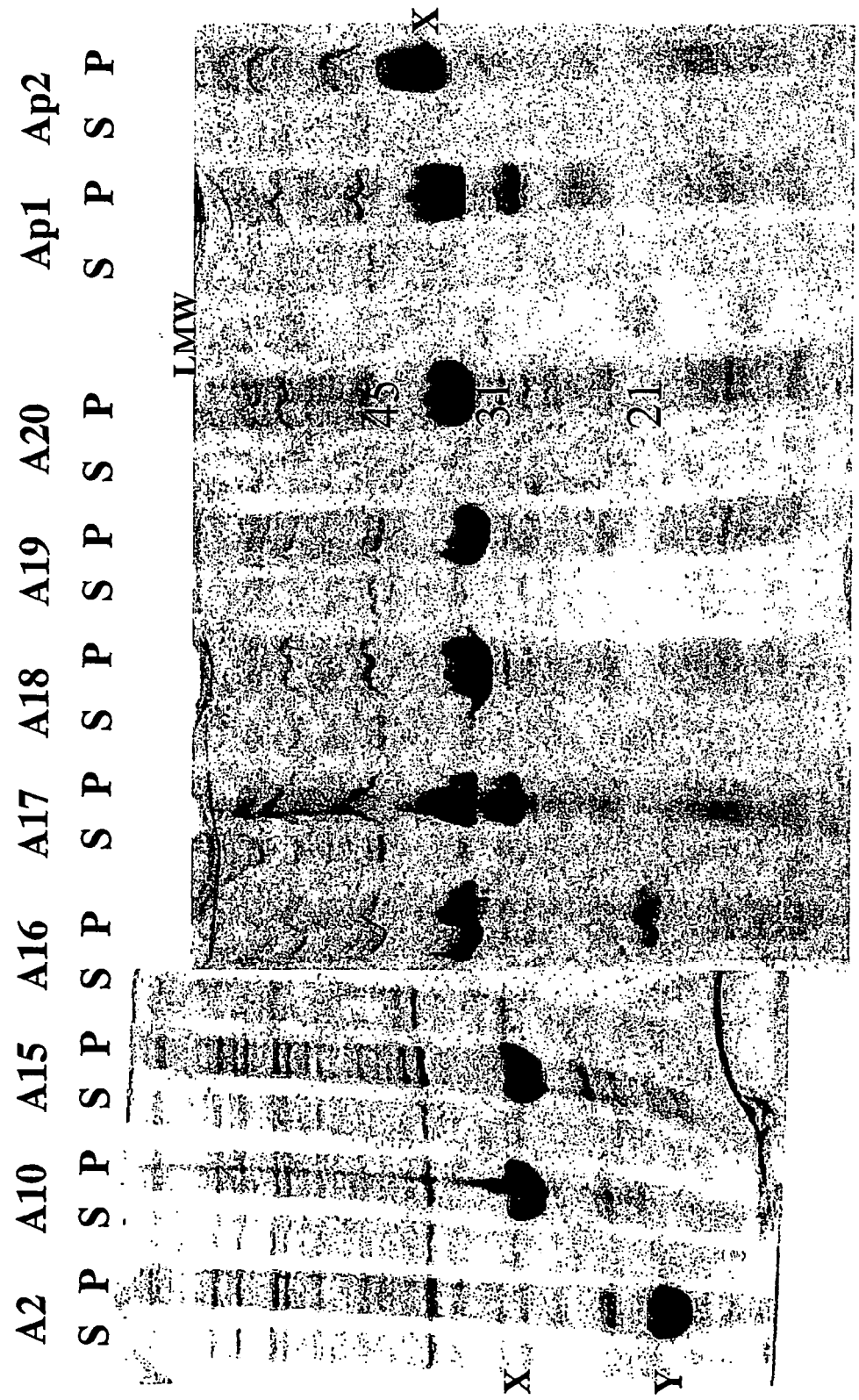

FIG. 11a. High-level expression of randomly chosen members of the pD_N2C library (A2, A10, . . . ). XL1-Blue cells containing one of the library expression plasmid pQE-pD_N2C were grown at 37° C. to an $OD_{600}$ =1 and induced for 1 h with 1 mM IPTG. The collected cells were resuspended in $TBS_{500}$, sonicated, and centrifuged. Samples corresponding to the supernatant (S) or pellet (P) of 40 microliters of cell culture were separated on a 15% SDS-PAGE and stained with Coomassie Blue. The clones are designated A2, A10, and so on. Ap1 and Ap2 are pools of 10 individual clones; Y: truncated pD_N2C (26 kDa), X: pD_N2C (33 kDa).

Figure 11B:
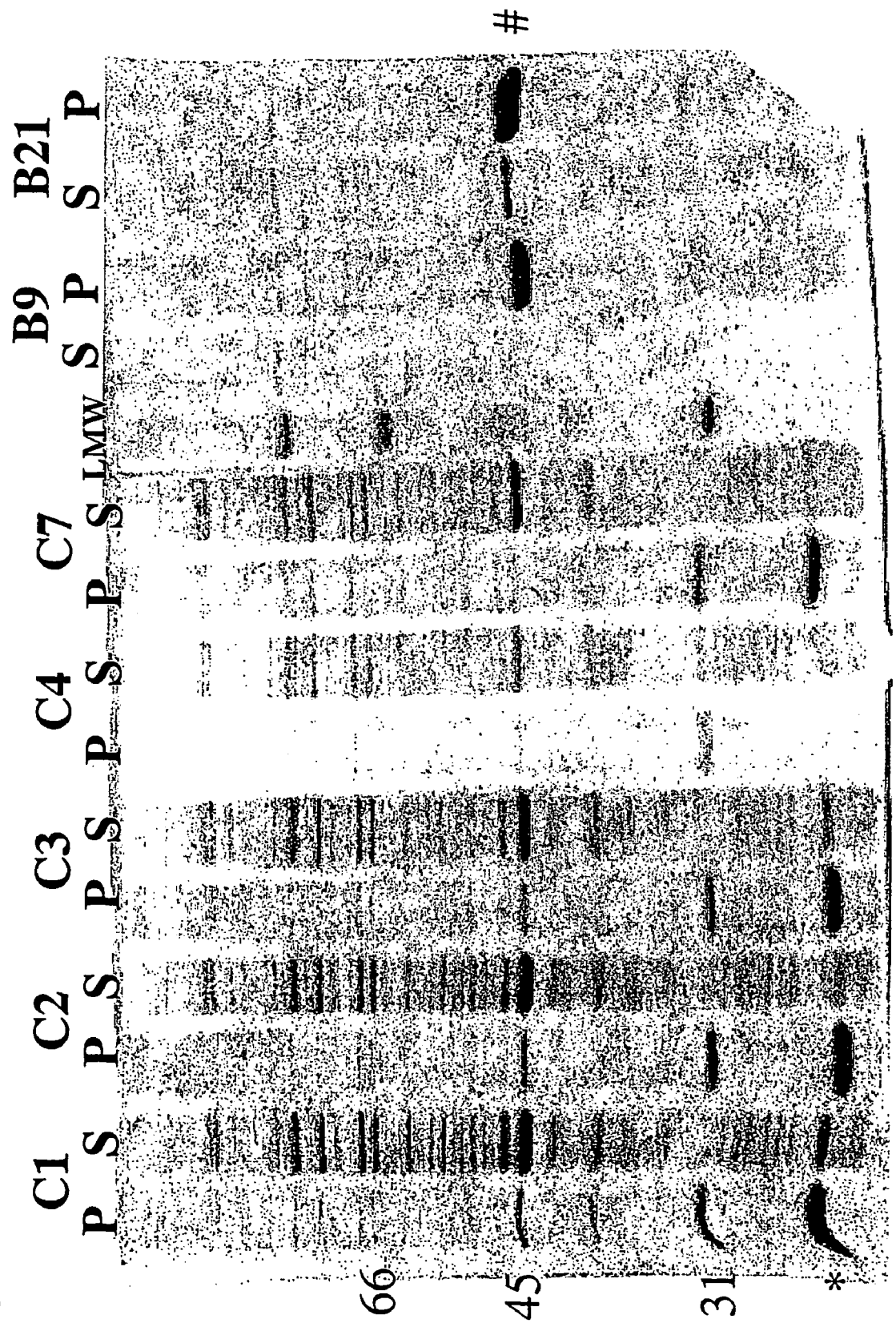

FIG. 11b. High-level expression of randomly chosen members of the N2C (C1, C2, . . . ) and pD_N4C (B9, B21) libraries as described in FIG. 11a; *: N2C (22 kDa), #: pD_N4C (45 kDa).

Figure 11C:
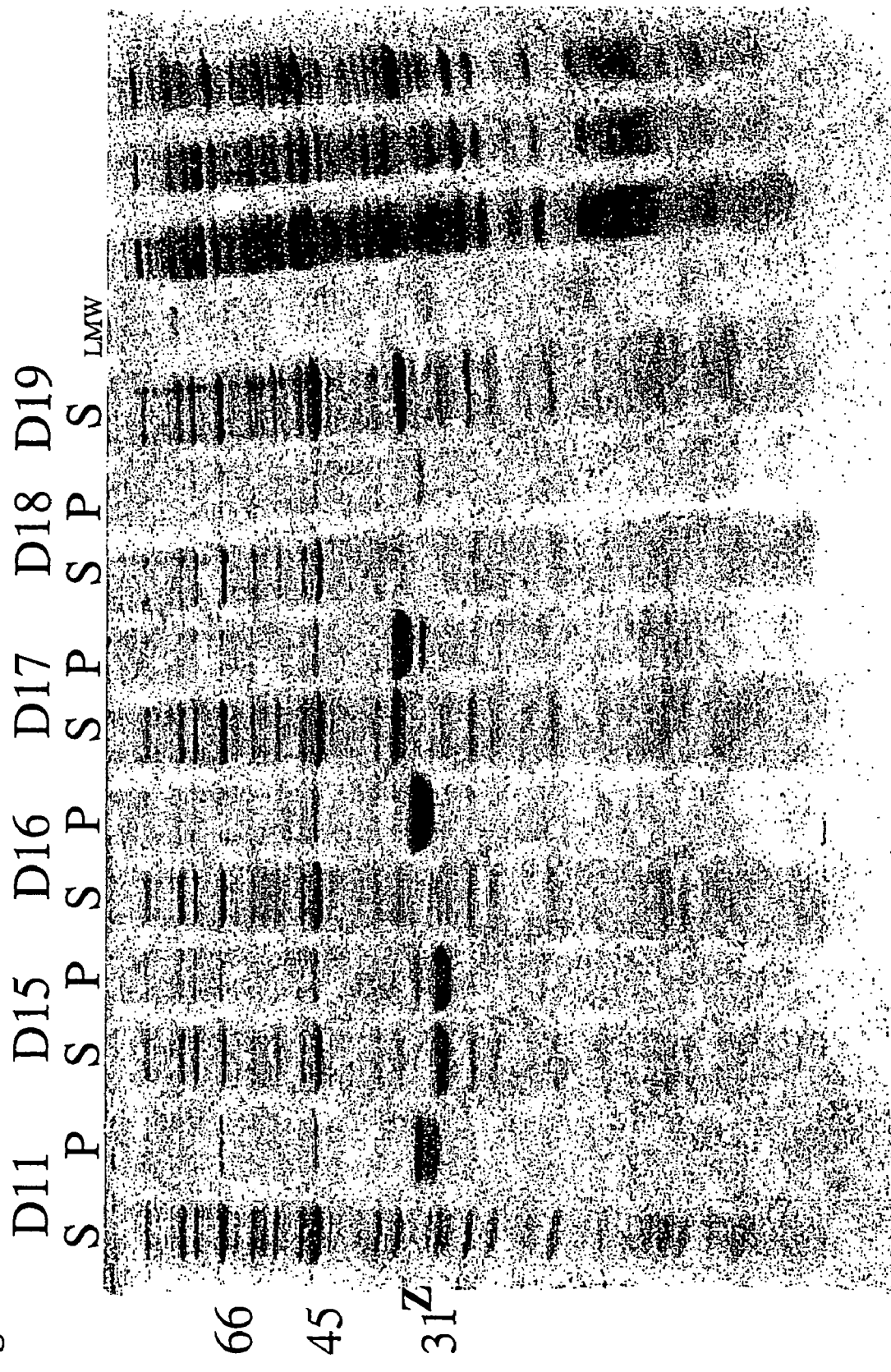

FIG. 11c. High-level expression of randomly chosen members of the N4C (D11, D15, . . . ) library as described in FIG. 11a; Z: N4C (34 kDa).

Figure 11D:
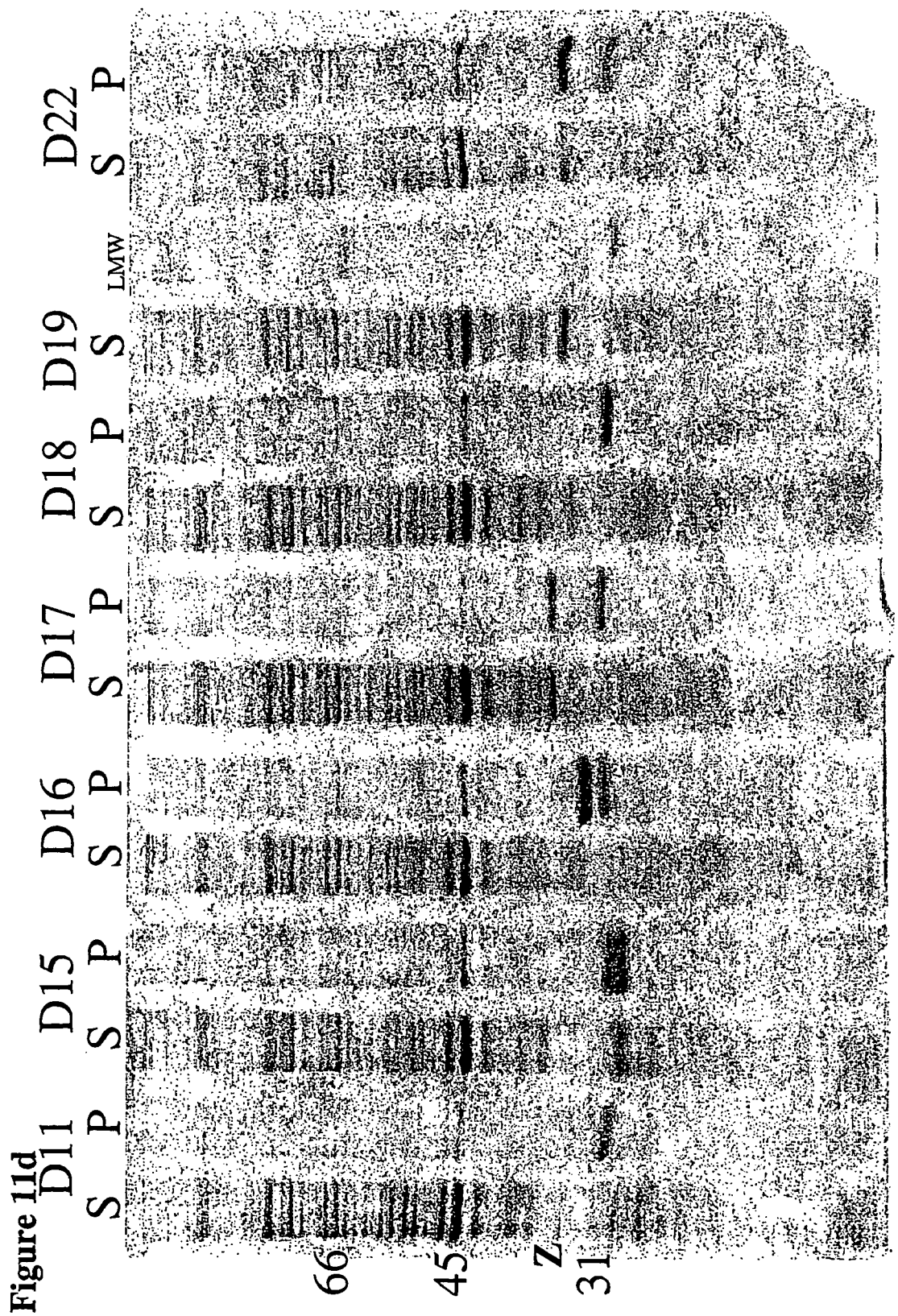

FIG. 11d. High-level expression of randomly chosen members of the N4C (D11, D15, . . . ) library as described in FIG. 11a but growth at 25° C.; Z: N4C (34 kDa).

Figure 12A:
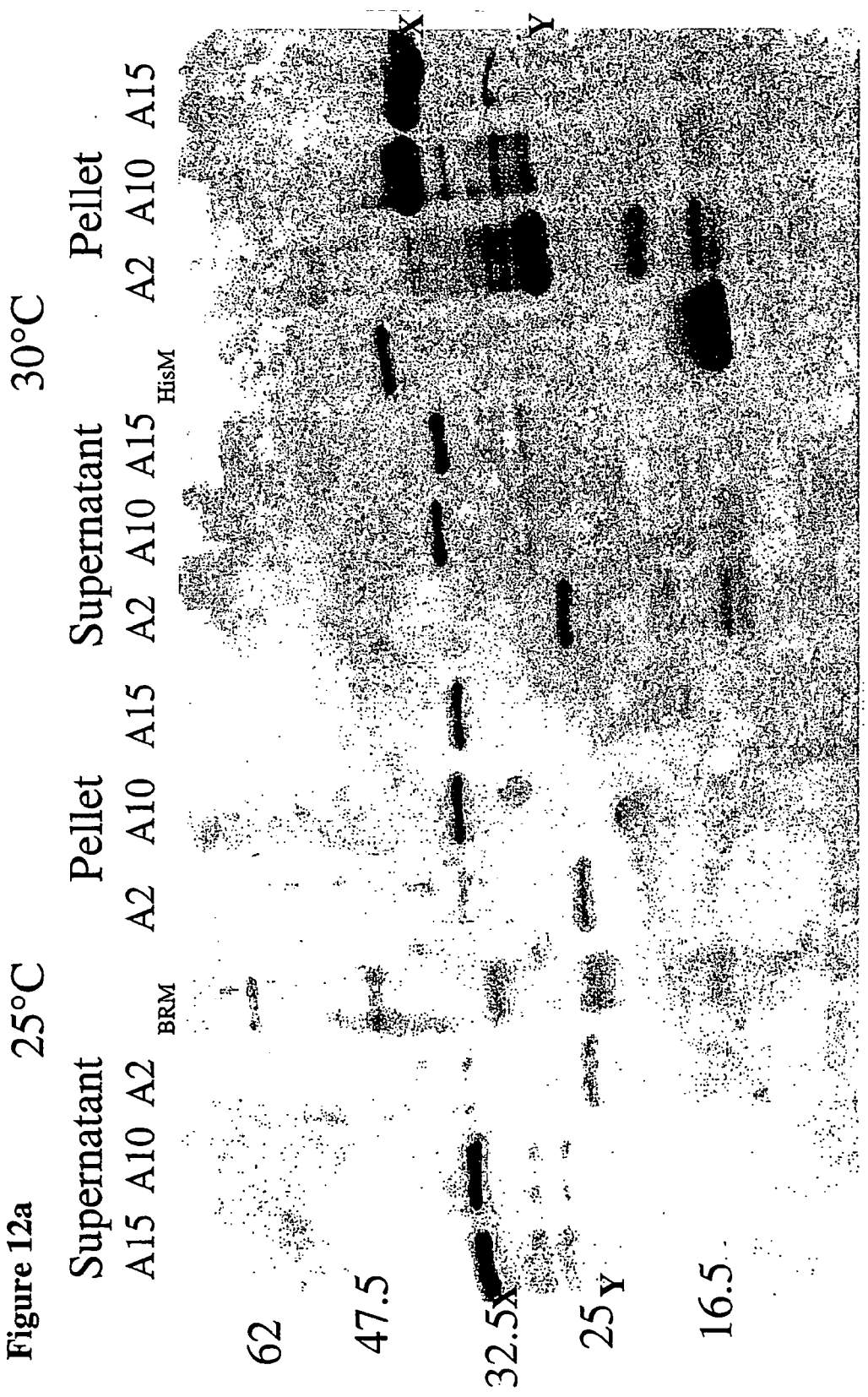

FIG. 12a. Western blot analysis of high-level expression of members of the pD_N2C library (A2, A10, A15) after expression at either 25° C. or 30° C. Protein was prepared as for FIG. 11a, Antibody anti-RGS-His was used in 1:5000 dilution following the manufacturer's protocol (Qiagen); Y: truncated pD_N2C (26 kDa), X: pD_N2C (33 kDa).

Figure 12B:
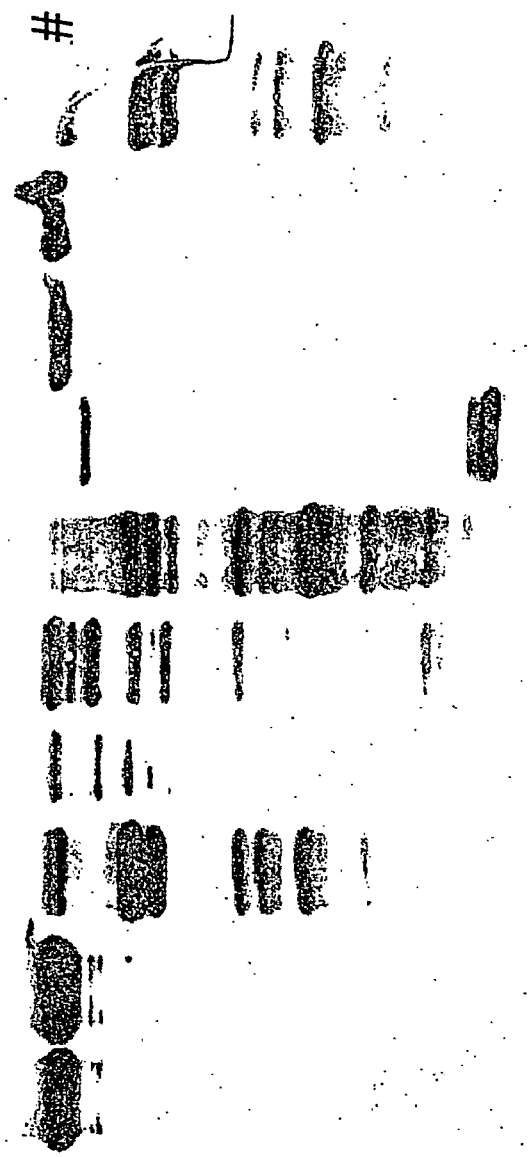

FIG. 12b. Western blot analysis of high-level expression of randomly chosen members of the pD_N4C library (B9, B21, BP which is a pool) after expression at either 37° C. or 25° C.; #: pD_N4C (45 kDa).

Figure 12C:
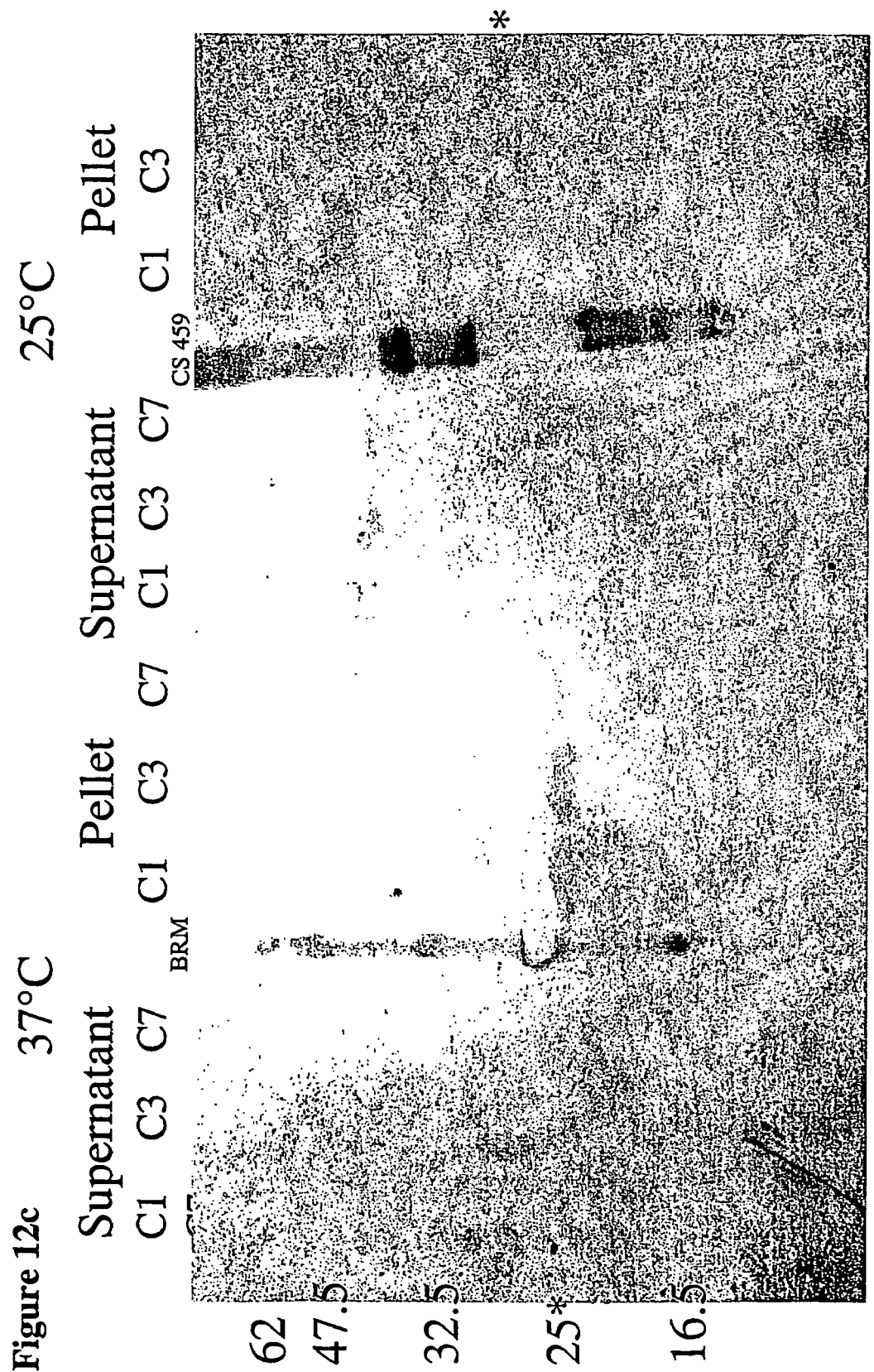

FIG. 12c. Western blot analysis of high-level expression of some members of the N2C library (C1, C3, C7) after expression at either 37° C. or 25° C. Protein was prepared as for FIG. 11a, Antibody anti-Flag M2 was used in 1:1000 dilution following the manufacturer's protocol (Sigma); *: N2C (22 kDa).

Figure 12D:
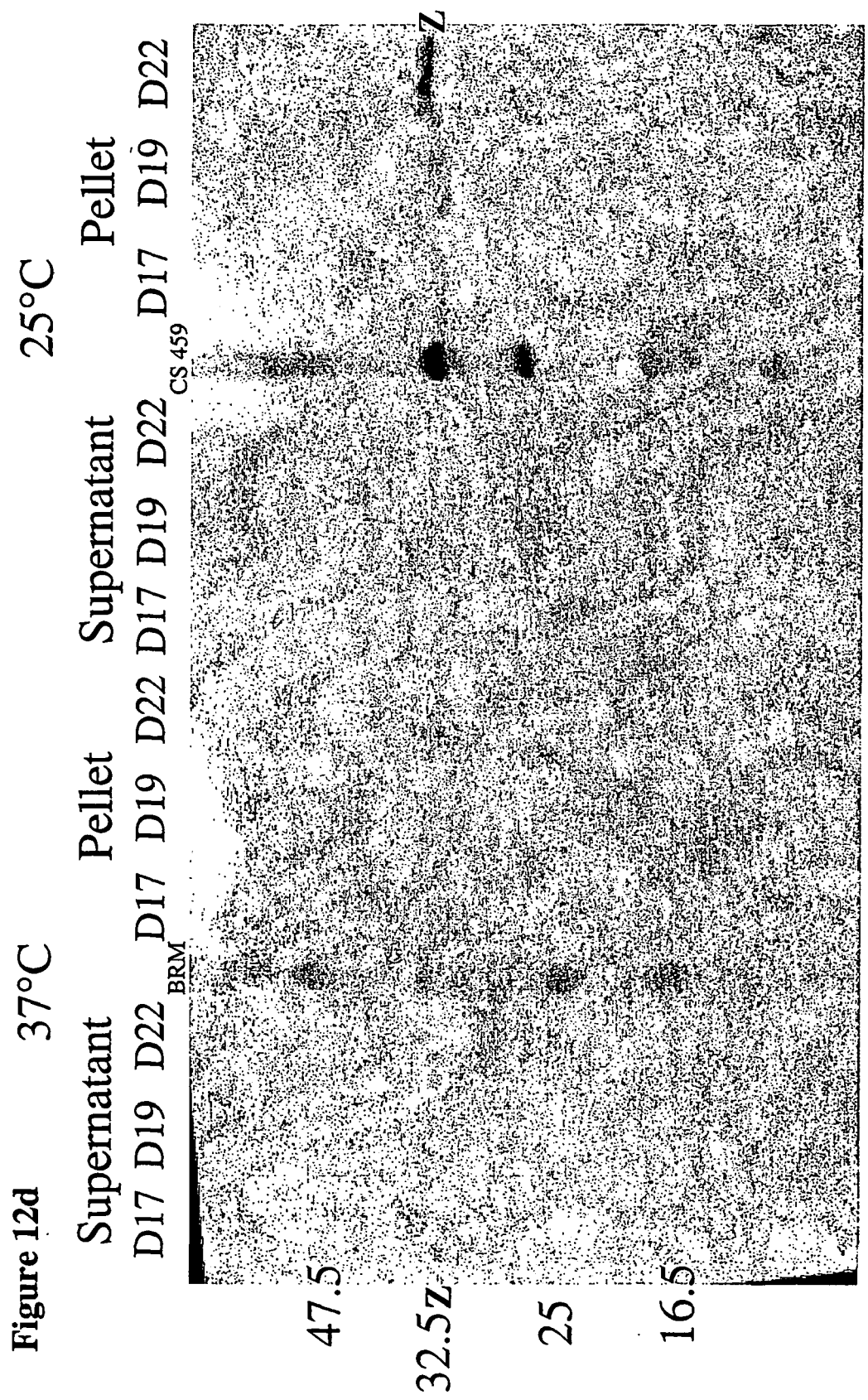

FIG. 12d. Western blot analysis of high-level expression of some members of the N2C library (D17, D19, D22) after expression at either 37 C. or 25 C.; Z: N4C (34 kDa).

Figure 13:
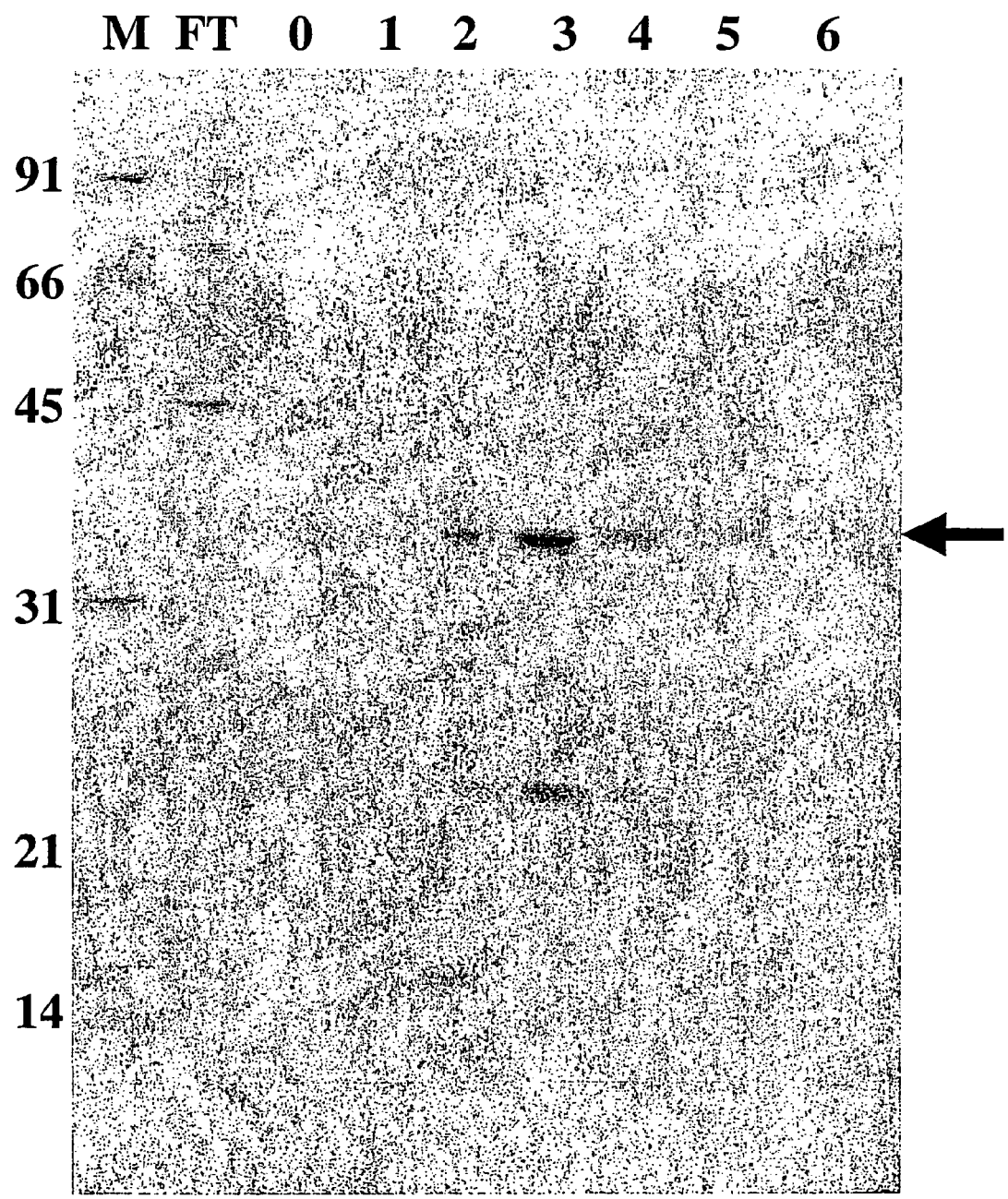

FIG. 13. HIS-tag purification under native conditions of a randomly chosen leucine-rich repeat protein according to the present.

Figure 14:
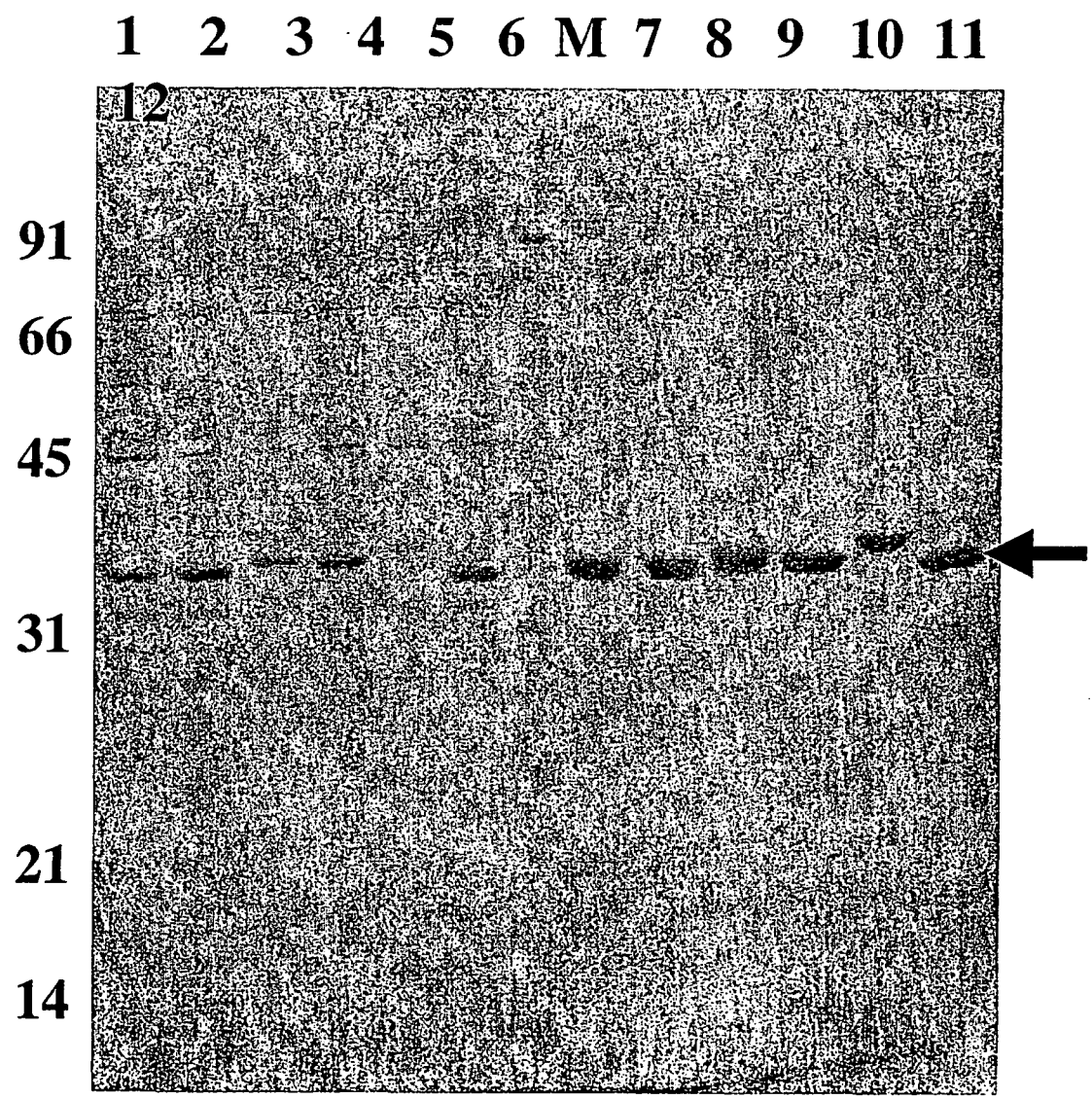

FIG. 14. His-tag purification under denaturing conditions including refolding of the repeat proteins in the purification column. Lanes 1 to 6 show the unbound fractions of six leucine-rich repeat proteins according to the present invention. Lanes 7 to 12 show the peak elution fractions of the same six proteins. The arrow indicates the position of the expected proteins.

Figure 15:
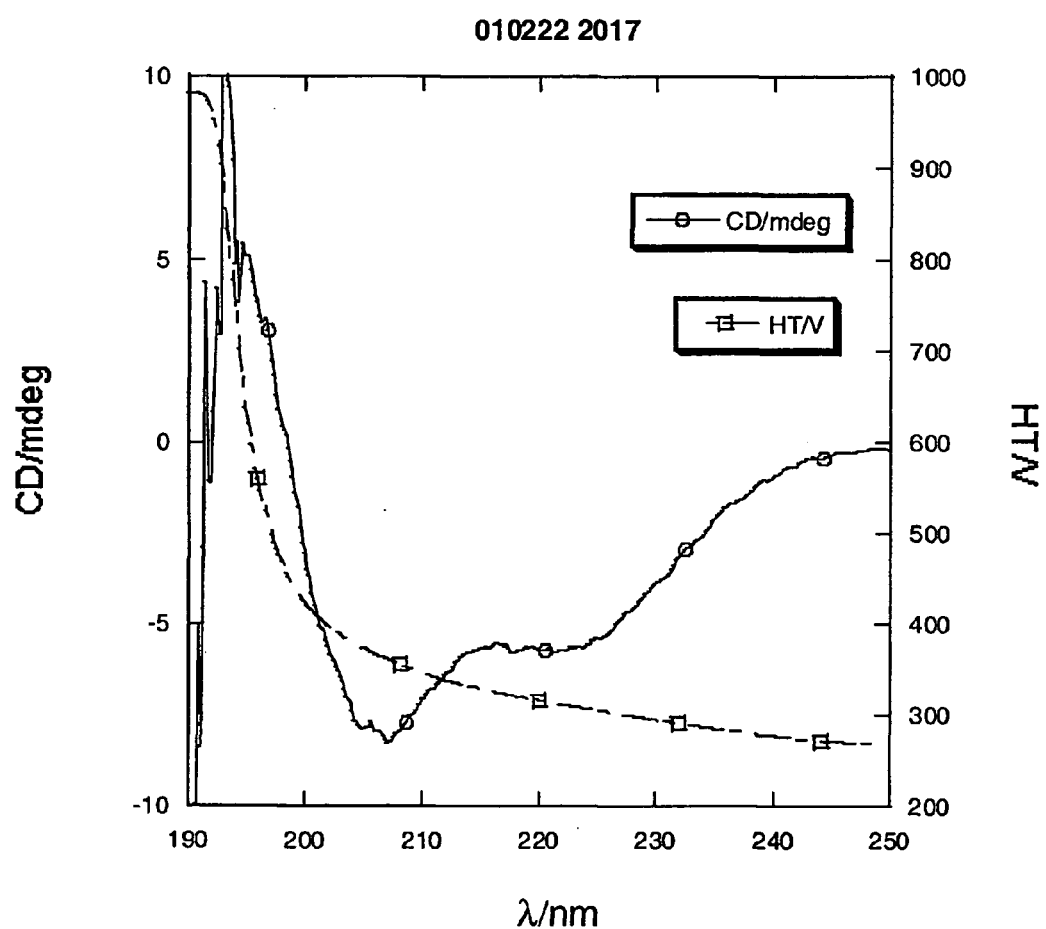

FIG. 15. Circular dichroism spectrometry of a randomly chosen leucine-rich repeat protein according to the present invention.

Figure 16:
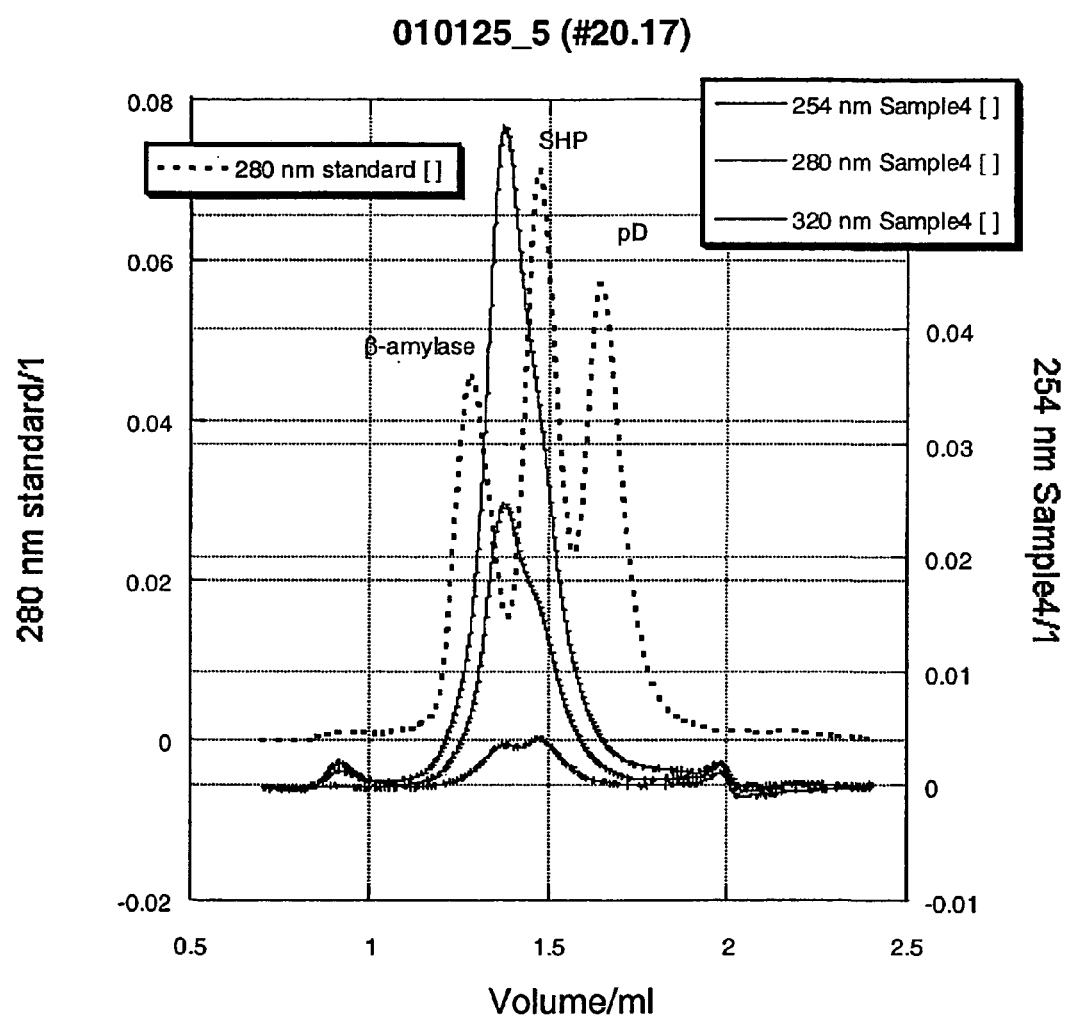

FIG. 16. Size exclusion chromatography of a randomly chosen leucine-rich repeat protein according to the present invention. The sample was analysed on a Superose 12 column.

FIG. 17. DNA recognition sequences of the restriction enzymes used for the cloning of ankyrin repeat proteins according to the present invention. Type II restriction enzymes cleave DNA within a palindromic recognition site, while type IIs restriction enzymes cut outside a non-palindromic recognition site. Two type IIs restriction enzymes (BpiI (SEQ ID NO: 66) and BsaI (SEQ ID NO: 67)) were used to ligate ankyrin repeat modules with each other in a directed manner by virtue of their compatible overhangs (see FIG. 18, Table 2 and Table 3), generating seamless connections of a ankyrin repeat module to the next one. These type IIs restriction enzymes were also used to link the N- and the C-terminal ankyrin capping modules with the ankyrin repeat modules separating them. BamHI and HindIII were used for the cloning of the ankyrin repeat proteins constructed according to the present invention (containing a N-terminal ankyrin capping module, two or more ankyrin repeat modules and a C-terminal ankyrin capping module) into plasmid pQE30(QIAgen, Germany). The pattern of restriction is indicated for each enzyme by solid lines.

Figure 18:
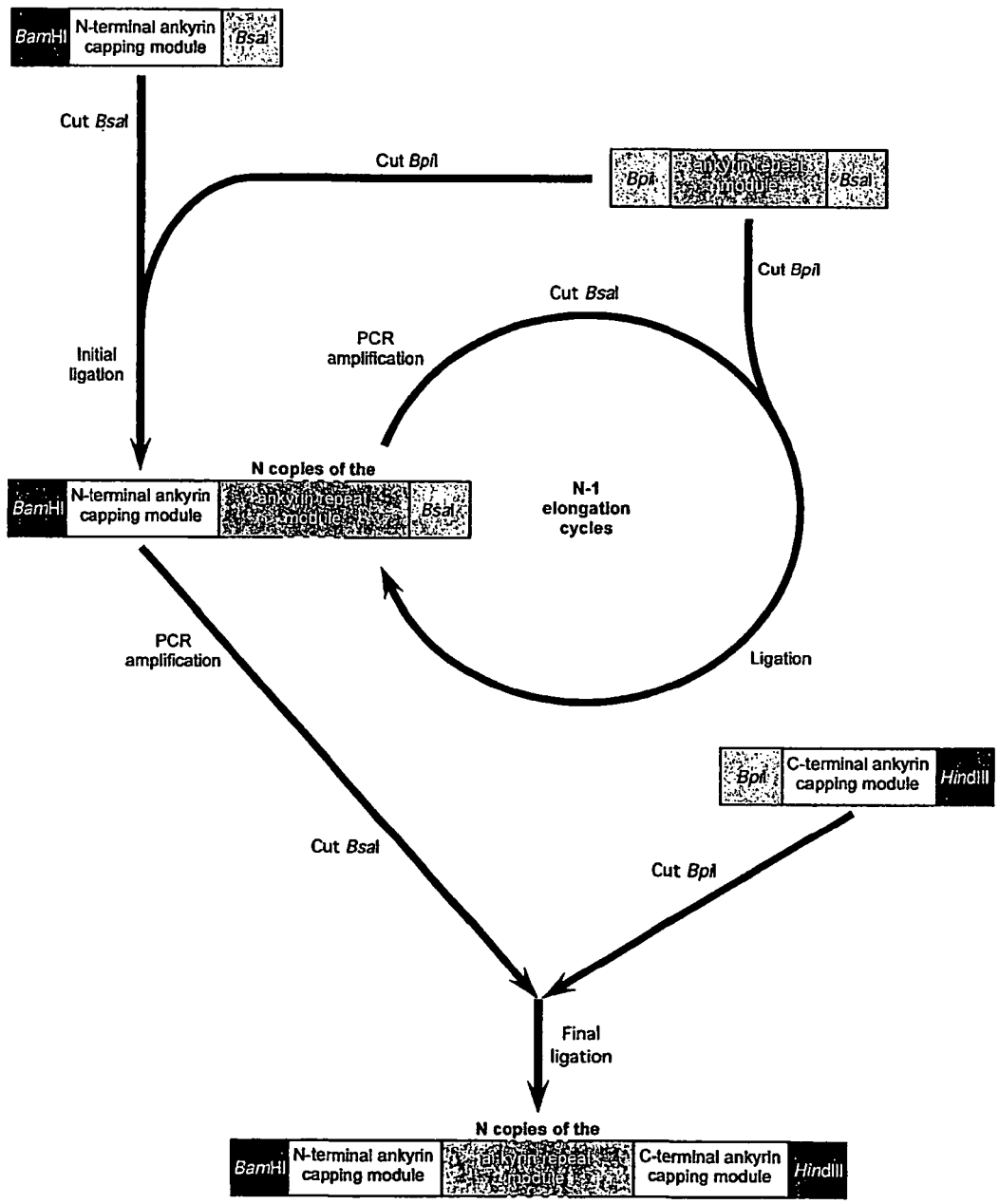

FIG. 18. Schematic view of the stepwise elongation of the N-terminal ankyrin capping module with ankyrin repeat modules on DNA level. The N-terminal ankyrin capping module is elongated by ankyrin repeat modules to the required length, followed and ended by the addition of the C-terminal ankyrin capping module.

Figure 19:
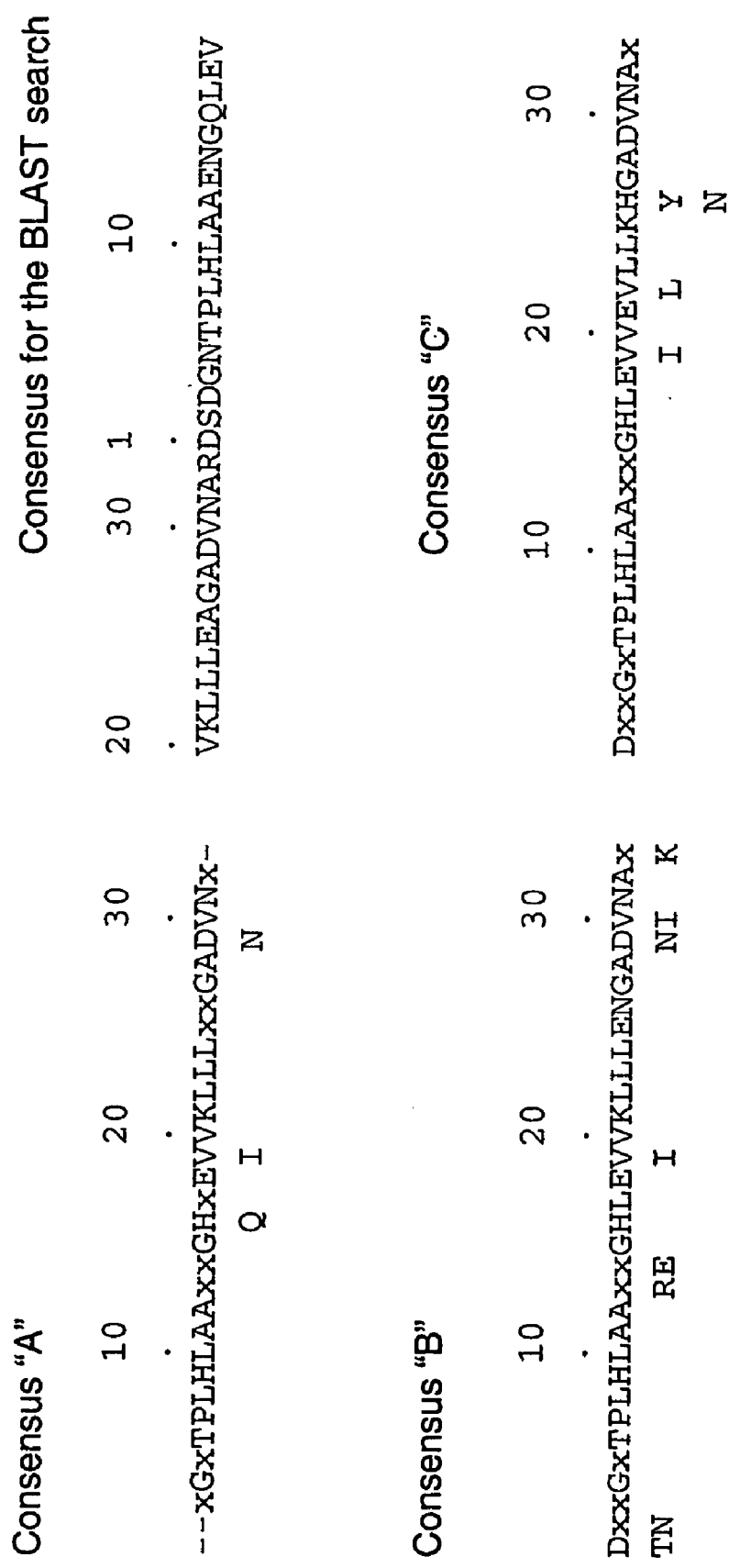

FIG. 19. Consensus "A" (SEQ ID NO: 68) (obtained after SMART analysis), the consensus used for the BLAST search (SEQ ID NO: 70) (circularly permutated consensus "A" where missing residues have been taken from a consensus of ankyrin repeat units of ankyrin repeat proteins with known three dimensional structure), consensus "B" (SEQ ID NO: 69) (derived after BLAST search) as well as consensus "C" (SEQ ID NO: 71) (finally obtained considering various parameters mentioned in EXAMPLE 2) are listed to illustrate the stepwise definition of the ankyrin repeat unit consensus. For consensus "A" and "B", residues reaching 20% frequency at a given position are displayed. In consensus "C", several amino acids are displayed at positions to which the latter amino acids fitted equally well.

Figure 20:
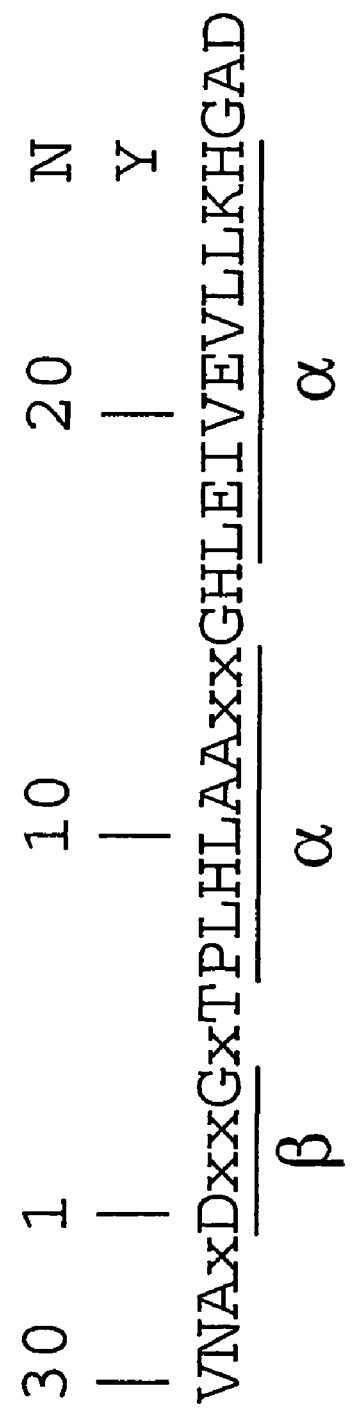

FIG. 20. The sequence of the ankyrin repeat motif (SEQ ID NO: 72) (i.e. the basis of all ankyrin repeat modules of EXAMPLE 2) and the respective position numbers of the amino acids are displayed. In addition, the expected secondary structures (□meaning □-helix, □ meaning □-sheet) are indicated. The six positions denoted "x" were defined as target interaction residues which were allowed to be any of the amino acids A, D, E, F, H, I, K, L, M, N, Q, R, S, T, V, W and Y. The remaining positions were defined to be framework residues defined by consensus "C" (cf. FIG. 19). At position 26, any out of the three amino acids histidine, tyrosine or asparagine were allowed. For cloning reasons the ankyrin repeat motif is based on a circularly permutated consensus "C" (cf. FIG. 19). To match the consensus numbering scheme used in FIG. 19 and used by Sedgwick and Smerdon (1999), the numbers were circularly permutated in parallel with the consensus sequence.

FIG. 21. Alignment of the randomly chosen clone "E3-5" (SEQ ID NO: 73 constructed according to the present invention. The amino acid sequence of E3-5, a protein having 3 ankyrin repeat modules (FIG. 20) between the N- and the C-terminal ankynn capping modules, is aligned to mouse GA-binding protein beta 1 (SEQ ID NO: 74. The latter is the protein showing highest homology to E3-5 among known ankyrin repeat proteins. The sequences were aligned using the command "gap" of GCG (Womble, D.D., 2000) with default values and the sequence comparison matrix BIosum62. Over all, the two molecules showed 67% residue identity and 71% residue homology. Positions corresponding to randomised positions in the repeat motif (cf. FIG. 20) are marked with an asterisk above. The N-terminal and C-terminal ankyrin capping modules are overlined, the three ankyrin repeat modules underlined.

Figure 22:
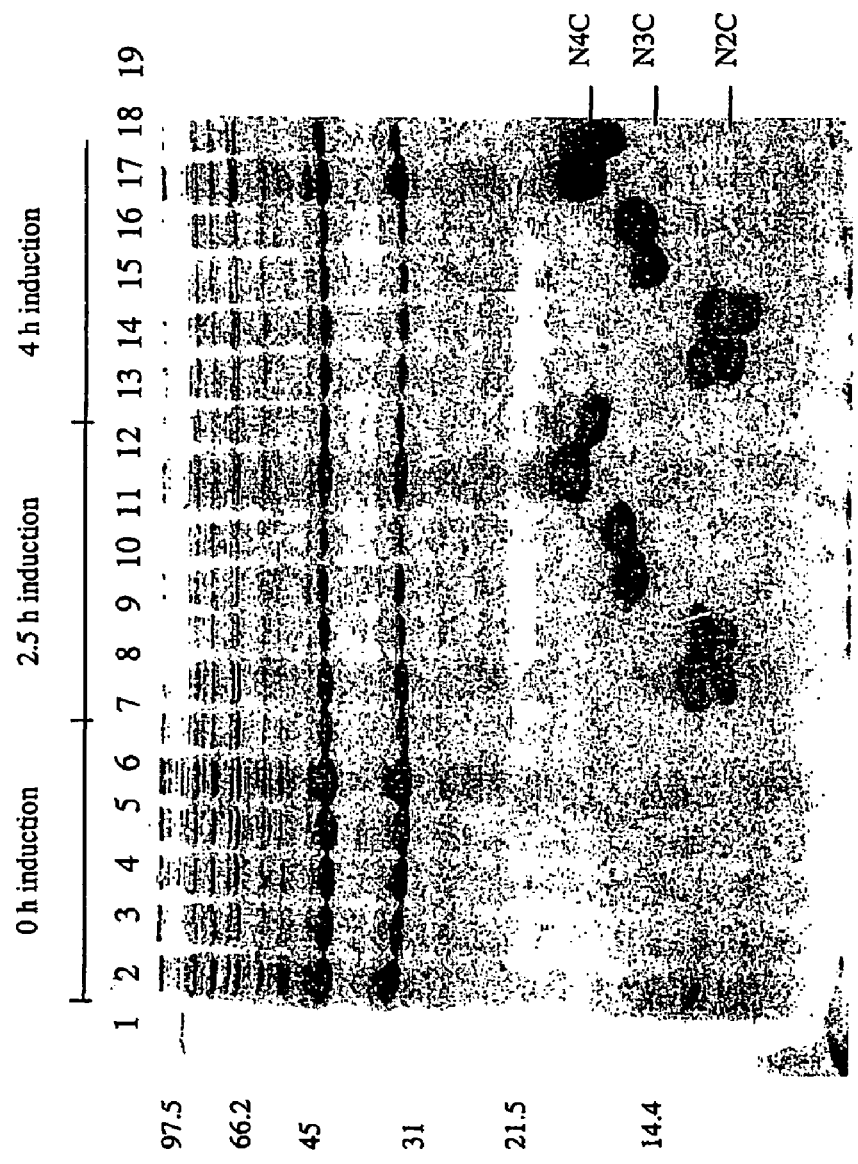

FIG. 22. High-level expression of differently sized ankyrin repeat proteins generated according to the present invention [BamHI/HindIII cloned into plasmid pQE30 (QIAgen); expressed in E. coli XL1-Blue (Stratagene)]. Of each library of N2C, N3C and N4C, two randomly chosen clones were tested. The abbreviation N2C refers to an N-terminal ankyrin capping module, two ankyrin repeat modules and a C-terminal ankyrin capping module being connected using the cloning strategy stated in FIG. 17 and FIG. 18. N3C and N4C are named accordingly to their content of three or four ankyrin repeat modules between their N- and C-terminal ankyrin capping modules. Expression was performed as described in EXAMPLE 2.

Samples corresponding to 30 µl of culture were taken at various timepoints and separated on 15% SDS-PAGE (Coomassie stained). Lane 1: Molecular marker (size indicated in kDa); Lane 2-7: two N2C, two N3C and two N4C clones just before induction; Lane 8-13: same as lane 2-7 but after 2.5 hours induction; Lane 14-19: same as lane 2-7 but after 4 hours induction.

Figure 23:
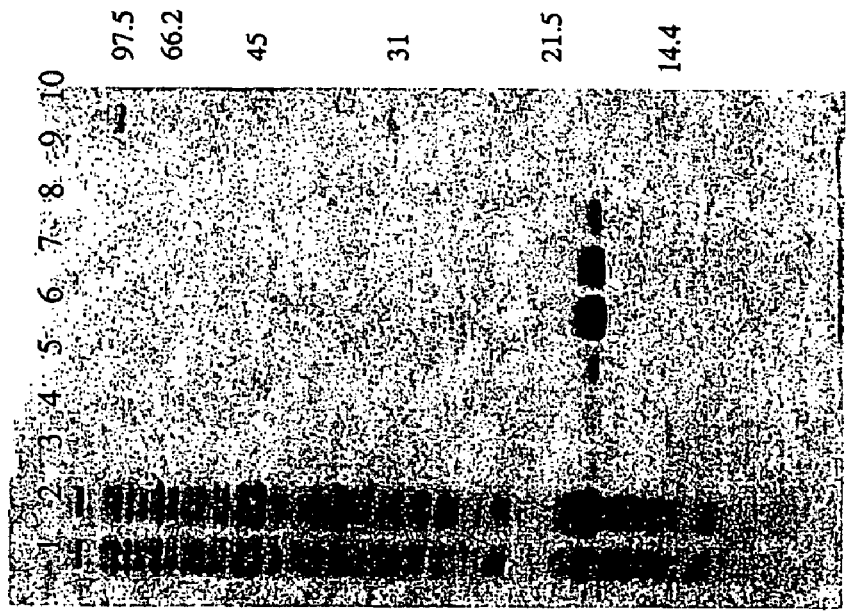

FIG. 23. His-tag purification of a randomly chosen ankyrin repeat protein generated according to the present invention. A 15% SDS-PAGE showing different fractions of the purification procedure is depicted. E3-5, an N3C clone, was expressed and purified as described in EXAMPLE 2. Lane 1 represents 0.6 µl of the collected cell lysate flow through which was not bound by the Ni-NTA columns. Lane 2 represents 0.6 µl of first 800 µl column washing fraction. Lane 3 represent 0.6 µl of the last 800 □l washing fraction. Lanes 4,5, 6, 7, 8 and 9 represent 0.6 µl of the subsequent elution steps (800 µl each) of the ankyrin repeat protein. Lane 10 shows the molecular marker (sizes in kDa).

Figure 24:
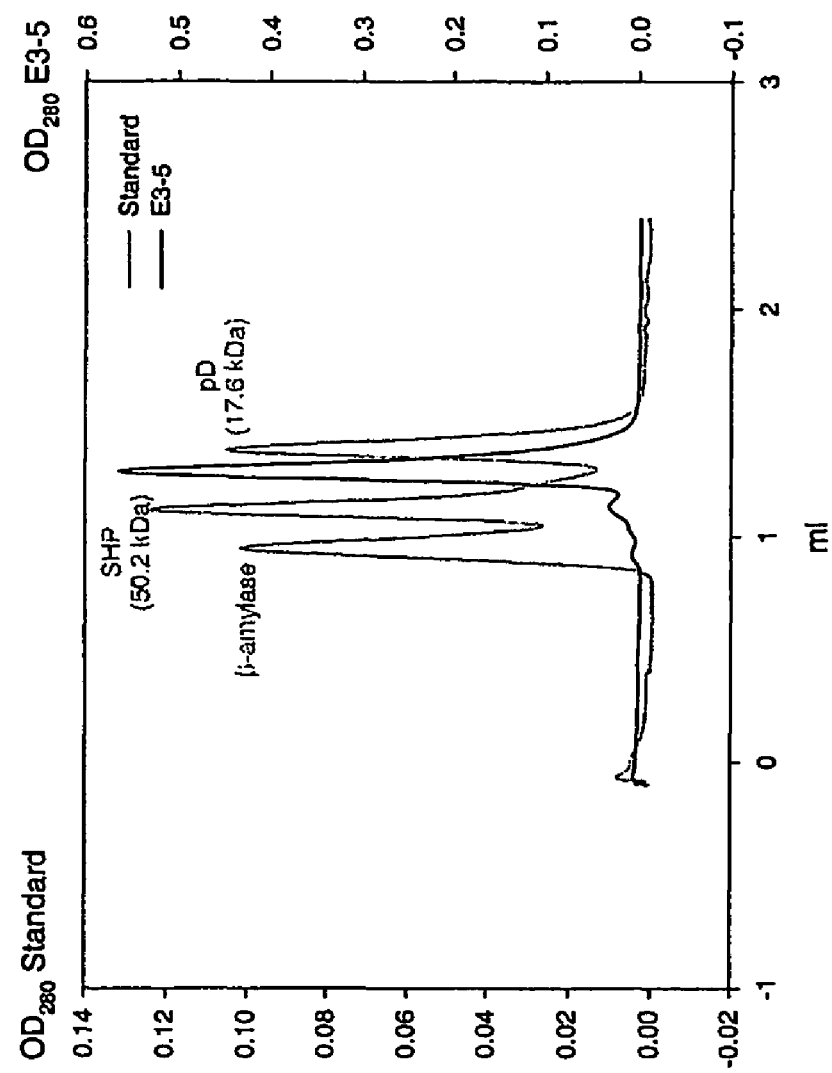

FIG. 24. Size exclusion chromatography of a randomly chosen ankyrin repeat protein generated according to the present invention (E3-5, a N3C molecule; cf. FIG. 22). The sample was analysed on a Superdex 75 column (Amersham Pharmacia Biotech, USA) using a Pharmacia SMART system at a flow rate of 60 µl/min and TBS 150 (50 mM Tris-HCl, pH 7.5; 150 mM NaCl) as running buffer. Standards were □-amylase and the phage proteins SHP of phage 21 and pD of □. The apparent masses of the standards are indicated in the figure. The apparent mass of 200 kDa for □-amylase is not indicated, as the protein eluted in the void volume.

Figure 25:
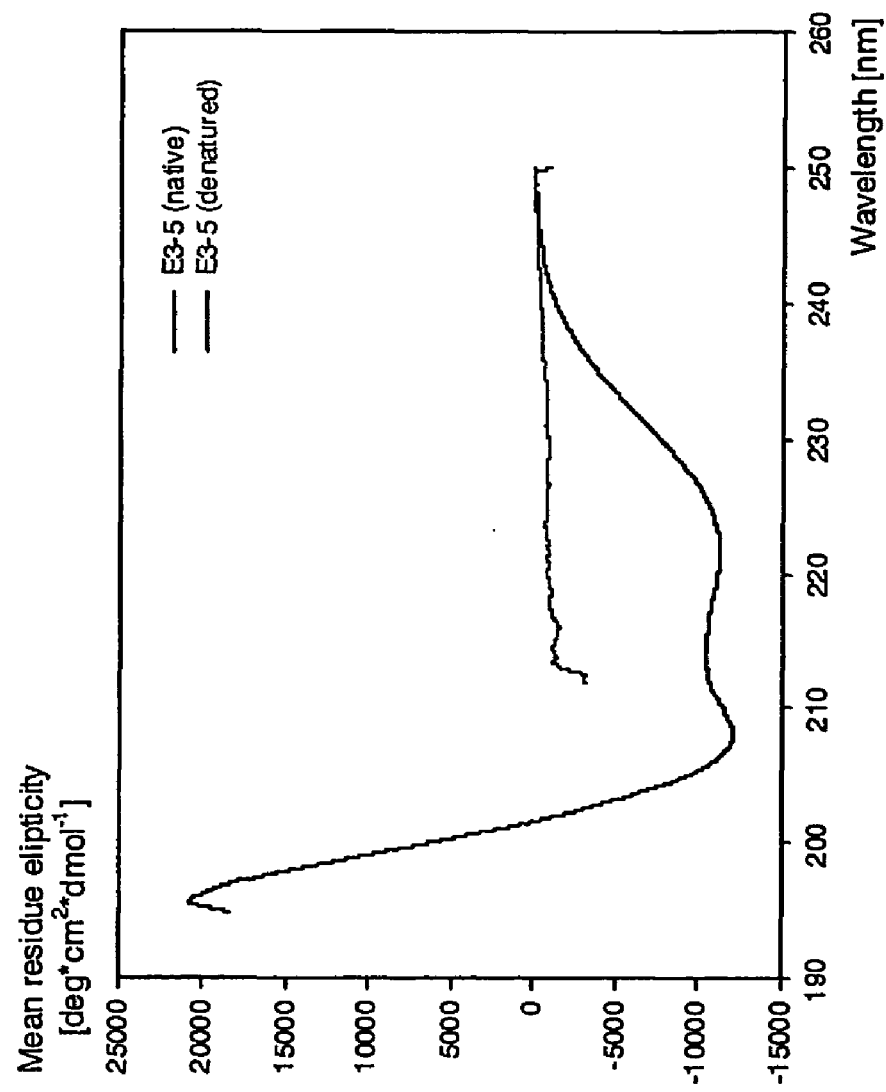

FIG. 25. Circular dichroism spectra of a randomly chosen ankyrin repeat protein generated according to the present invention (E3-5, a N3C molecule). The spectra were recorded either in 10 mM sodium phosphate buffer pH 6.5 (native) or 20 mM sodium phosphate buffer pH 6.5 and 6 M Guanidinium hydrochloride (denatured) using a Jasco J-715 instrument [Jasco, Japan; 10 nm/s, 8 sec response, 0.2 nm data pitch, 2 nm band width, 195-250 nm (native) or 212-250 nm (denatured), three accumulations, measurements in triplicates, 1 mm cuvette]. The CD signal was converted to mean residue elipticity using the concentration of the sample determined spectrophotometrically at 280 nm under denaturing conditions. E3-5 shows an alpha-helical spectrum under native conditions with minima at 208 nm and 222 nm. The secondary structure is lost in 6 M Guanidinium hydrochloride.

Figure 26:
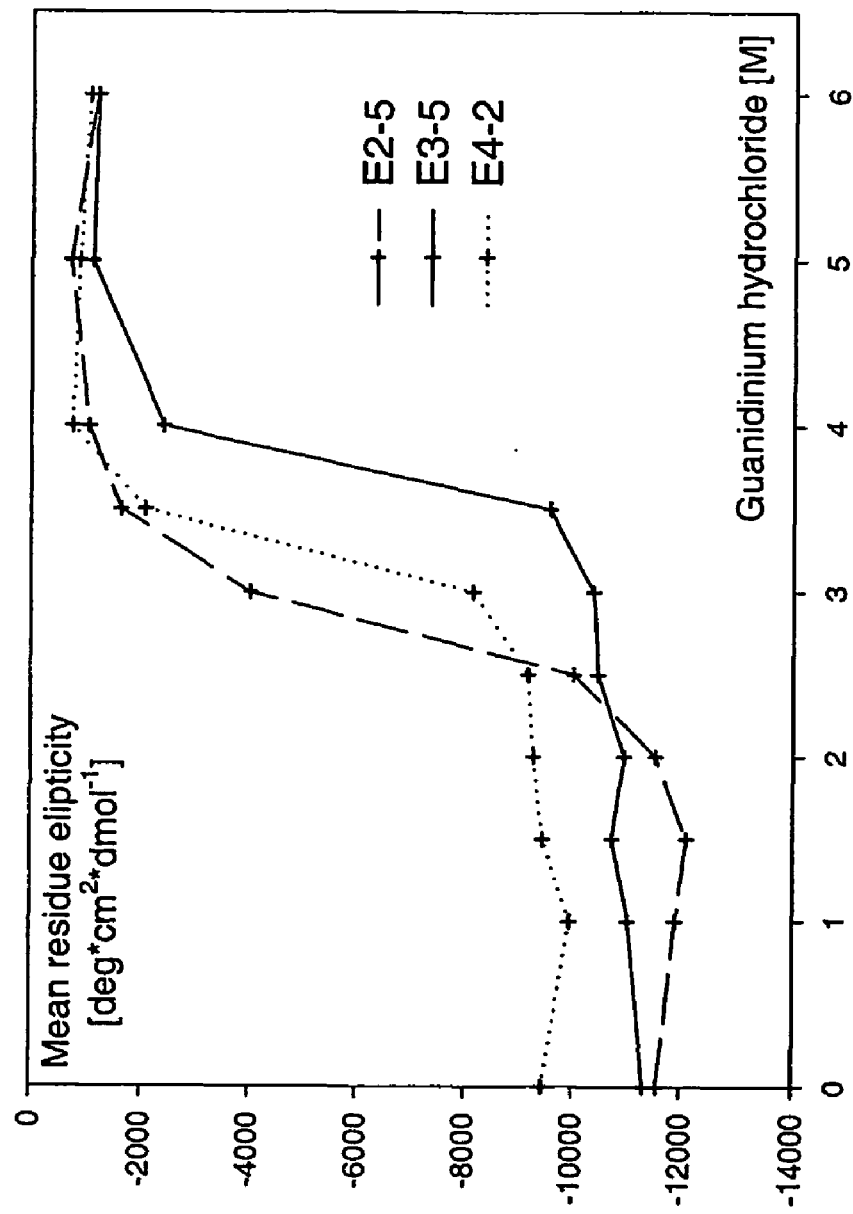

FIG. 26. Denaturation behaviour of randomly chosen ankyrin repeat proteins generated according to the present invention (cf. FIG. 22). The CD values at 220 nm are shown over guanidinium hydrochloride concentration for the different proteins. The different proteins were incubated with different concentrations of guanidinium hydrochloride in 20 mM NaPO4 pH6.5, 100 mM NaCl, overnight at room temperature. The circular dichroism signal at 220 nm was measured for each sample in triplicates (conditions as indicated in EXAMPLE 2). The secondary structure is lost only at high concentrations of denaturing agent indicating a high stability of the tested proteins.

Figure 27:
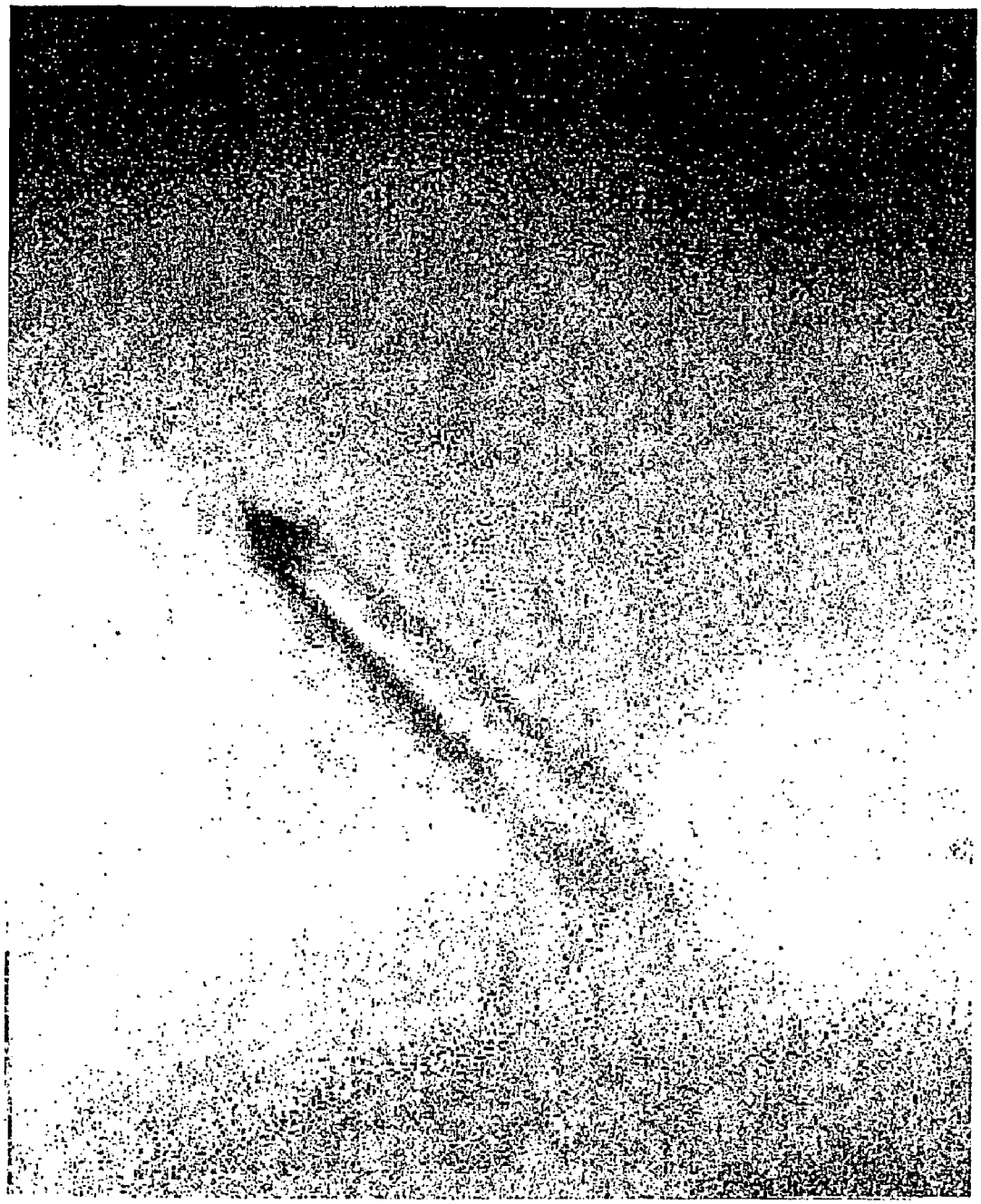

FIG. 27. Crystals of a randomly chosen ankyrin repeat protein generated according to the present invention (E3-5, a N3C library member of FIG. 22). The crystal was grown in five days at 20° C. in 20% PEG 6000, 100 mM MES/NaOH pH 6.0, hanging droplet (2 µl protein and 2 µl buffer mixed; 500 µl buffer reservoir) from a solution of 9 mg Protein per ml in TBS 50 (50 mM TrisHCl, pH 8.0, 50 mM NaCl).

The examples illustrate the invention.

EXAMPLES

Unless stated otherwise in the examples, all recombinant DNA techniques are performed according to described protocols (Sambrook et al., 1989 or Ausubel et al., 1994). Databases used were Genbank
    National Center for Biotechnology Information, National Library of Medicine,
    Bethesda, USA Swiss-Prot
    Swiss Institute of Bioinformatics, Geneva, Switzerland Protein Data Base
    Center for Molecular Biophysics and Biophysical Chemistry at Rutgers, New Jersey, USA Simple Modular Architecture Research Tool (SMART)
    EMBL, Heidelberg, Germany 1. Collection of Repeat Proteins Comprising Repeat Modules Derived from Repeat Units of Mammalian Ribonuclease Inhibitors This example describes the construction of a collection of leucine-rich repeat proteins derived from mammalian ribonuclease inhibitors (RI). This scaffold was chosen, since extraordinarily tight interactions in the femtomolar range have been reported for the binding of angiogenin by RI (Lee et al., 1989) and RNase A by RI (Kobe and Deisenhofer, 1996).

Figure 4F:
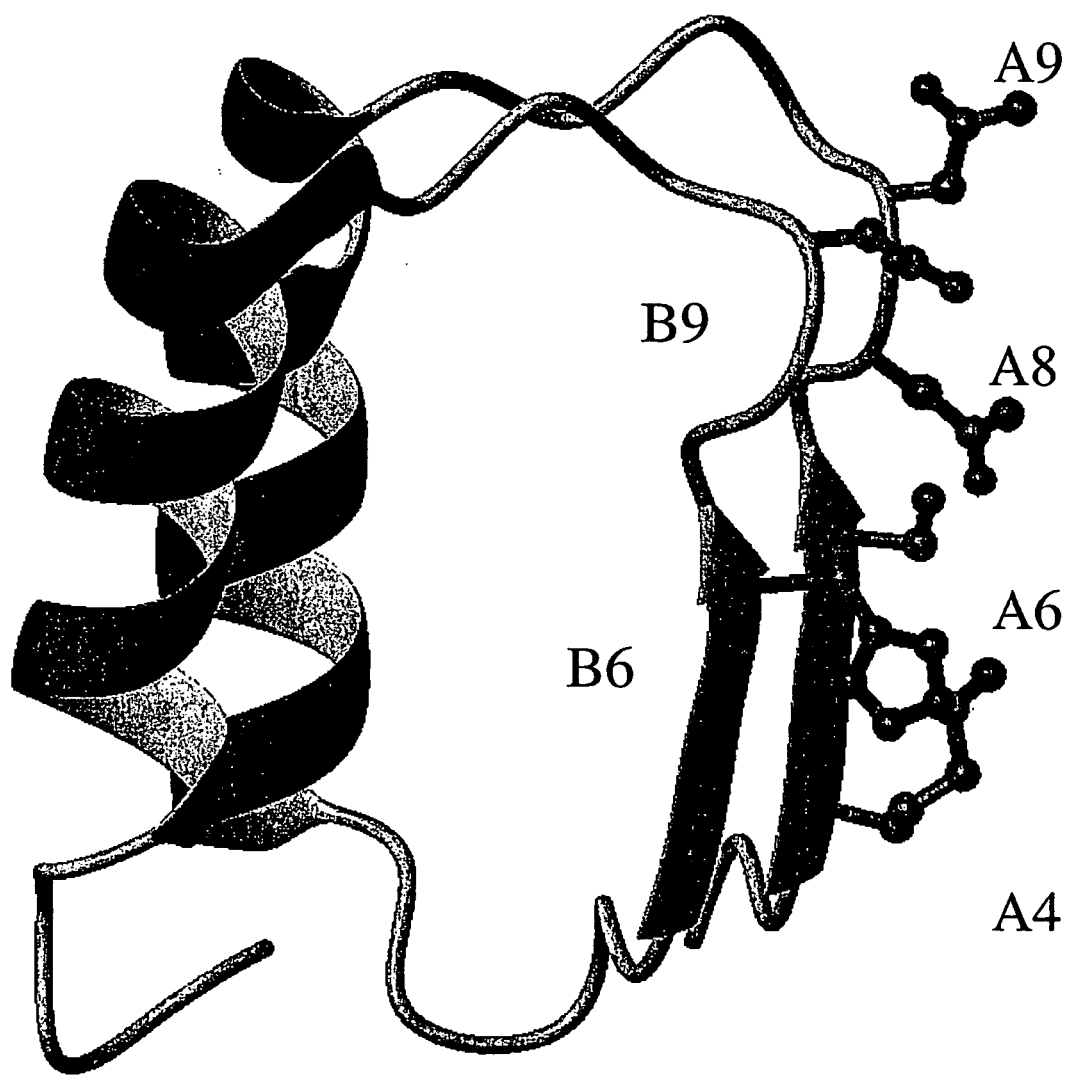

As the RI amino acid sequence showed a characteristic pattern of two alternating, different but homologous repeat units, termed A- and B-type LRR repeat unit (Kobe and Deisenhofer, 1994), two according repeat motifs were derived and used to build a repeat domain. The assembly of a LRR repeat motif of type A with a LRR repeat motif of type B is henceforth referred to as RI repeat motif pair. A model of a repeat module pair comprising a RI repeat motif pair is shown (FIG. 4f). This example demonstrates the use of more than one repeat motif to build a repeat domain, which is in contrast to example 2 where only one repeat motif is used.

1) Deriving Preliminary Repeat Sequence Motifs of Mammalian RI

The protein sequences of human RI (accession number P13489, Lee et al., 1988) and pig RI (P10775, Hofsteenge et al., 1988) were used to search for homologous sequences. The complete protein sequence of the rat RI (P29315, Kawanomoto et al., 1992) and mouse RI protein were found (AAK68859, unpublished).

The repeat units of the obtained RI protein sequences were aligned using "FastA" implemented in the GCG® Wisconsin Package™ (Accelrys, USA). The protein sequence of human RI is shown (FIG. 5a) and the LRR pattern characterised by leucines or other aliphatic residues at positions 2, 5, 7, 12, 20, and 24 (Kobe and Deisenhofer, 1994) is highlighted.

The most abundant amino acid for each position was calculated for the human, mouse, pig, and rat RI sequences (FIGS. 5c and 5d). A first RI repeat motif pair was defined by amino acids occurring in 50% (cf. FIGS. 5c and 5d) or more of the cases at a given position

```
A-type LRR consensus 1 3 5 7 9 11 13 15 17 19 21 23 25 27
-LE-L-L--C-LT-A-C--L-SVL----
(SEQ ID NO: 11)

B-type LRR consensus 1 3 5 7 9 11 13 15 17 19 21 23 25 27 29
SL-EL-LS-N-LGD-G---LC-GL--P-C
(SEQ ID NO: 12)
```

For a threshold of 40% or more identical amino acids at a given position the RI repeat motif pair was defined by the following amino acid sequence

```
A-type LRR consensus 1 3 5 7 9 11 13 15 17 19 21 23 25 27
+LE-L-L--C-LTAA-C-DL-SVLRAN-
(SEQ ID NO: 13)
where + is R or K B-type LRR consensus 1..3 5 7 9 11 13 15 17 19 21 23 25 27 29
SL-EL-LS-N-LGDAG---LC-GL--P-C
(SEQ ID NO: 14)
```

Similarly, for a threshold of 30% or more identical amino acids at a given position the RI repeat motif pair was defined by the following amino acid sequence

```
A-type LRR consensus 1 3 5 7 9 11 13 15 17 19 21 23 25 27
+LE-LWL-DCGLTAAGCKDLCSVLRAN-
(SEQ ID NO: 15)
where + is R or K B-type LRR consensus 1 3 5 7 9 11 13 15 17 19 21 23 25 27 29
SLREL-LS*N-LGDAGV-LLCEGLL-P-C
(SEQ ID NO: 16)
where * is N or S
```

Finally, for a threshold of 25% or more identical amino acids at a given position the RI repeat motif pair was almost completely defined by only one amino acid per position.

```
A-type LRR consensus 1 3 5 7 9 11 13 15 17 19 21 23 25 27
+LEKLWLEDCGLTAAGCKDLCSVLRANP
(SEQ ID NO: 17)
where + is R or K B-type LRR consensus 1 3 5 7 9 11 13 15 17 19 21 23 25 27 29
SLRELDLS*NELGDAGVRLLCEGLL#PGC
(SEQ ID NO: 18)
where * is N or S
and # is D or Q
```

This is to illustrate how a sequence motif can be derived only from sequence information and alignment. However, preferably structural information should be taken into account 2) Defining Framework and Target Interaction Residue Positions The analysis of both A- and B-type LRR units revealed that the side chains of the amino acids at positions 2, 5, 7, 10, 12, 17, 20, and 24 are always oriented towards the hydrophobic core (Kobe and Deisenhofer, 1994 and FIGS. 4b and 4d) and these amino acids constitute a subset of the framework residues. Other framework residues are the glycine at position 16 and the prolines at position 28 in the A-type LRR unit (abbreviated A28) and position 27 in the B-type LRR unit (abbreviated B27), since they initiate and terminate the α-helix of each LRR unit. Furthermore, positions A1, A3, A13, A18, A19, A22, A25, A27 and B1, B3, B11, B14, B18, B22, and B26 most often harbour hydrophilic amino acid residues oriented towards the surrounding solvent and were treated as framework positions. Similarly, positions A14, A15, A21, A23, A26, and B15, B19, B21, B25, and B29 are usually occupied by hydrophobic amino acid residues stabilising the interface of the repeat modules and are thus also treated as framework positions. Further, positions A11, B13, B23 and B28 feature glycine with allow more flexibility than other amino acids and are therefore also important for the framework. In contrast, the positions 4, 6, 8, and 9 were defined to be the target interaction positions in the RI repeat motif pair.

3) Replacing Unfavorable Amino Acids

The RI consensus is also characterised by extremely well conserved cysteines at positions A10 and A17 and positions B21 and B29. However, as free cysteines may be oxidised and cause complications, it is desirable to design cysteine free modules. Therefore, appropriate replacements were sought. Inspection of the three-dimensional structure (MTS#1) revealed that the cysteine at position A10 made a H-bond.

Further, alignments to more distant LRR molecules revealed the presence of either asparagine, serine, or threonine in most cases. Thus, the position A10 in the LRR module was designed to be occupied by these three amino acids. Similarly, position A17 was found to be part of the hydrophobic core, which is why in the LRR module methionine, leucine, or valine were used. At the same time, these two positions A10 and A17 constitute cases where framework positions are randomised. At position B21, the cysteine of the first and last repeats in all analysed RI sequences was constantly occupied by leucine (with one exception of valine) and thus defined to be leucine in the final LRR module. In case of position B29, the choice was accordingly between serine and threonine, where the threonine was chosen to allow an assembly with the restriction endonuclease sites of BssHll and MluI (for a detailed description see FIG. 6).

The last remaining cysteine, which occurred in 36% of the analysed position A21 (FIG. 5c), was set to be alanine because this was the second most frequent amino acid at the given position and also seemed to match the hydrophobic environment. The decision was facilitated since it was noted that in most cases where leucine was found at position B21, position A21 was occupied by alanine. In other words, the leucine at position B21 seems to prefer alanine at position A21. Thus, stacking was believed to be supported best with this choice in the LRR module.

Another decision was required for position A1. From the two possible positively charge amino acids lysine and arginine, the latter was chosen to match the above mentioned restriction endonuclease sites.

The refined repeat sequence motif can thus be described by the following sequence

```
A-type LRR consensus 1 3 5 7 9 11 13 15 17 19 21 23 25 27
RLEKLWLED2GLTAAG4KDLASVLRANP
(SEQ ID NO: 19)
where 2 is N or S or T
and 4 is L or M or V B-type LRR consensus 1 3 5 7 9 11 13 15 17 19 21 23 25 27 29
SLRELDLS*NELGDAGVRLLLEGLL#PGT
(SEQ ID NO: 20)
where * is N or S
and # is D or Q
```

4) Defining the Target Interaction Residues

For the definition of the target interaction positions, both the human RI-angiogenin (Papageorgiou et al., 1997) and the pig RI-RNase A (Kobe and Deisenhofer, 1995) complexes were analysed. Apart from extensive interactions at both the N- and the C-terminal capping units, the interactions of repeat units involved most frequently positions 6, 8, and 9 of the A-type LRR unit, whereas in the B-type LRR unit, positions 4, 6 and 9 were used most often. All these positions are characterised by side chains emanating from the β-strand of the LRR unit (FIG. 4e) and are therefore suited for target interactions. As however, the glutamate at position 4 of the B-type LRR unit was present without exception and an additional structural importance could not be dismissed, we refrained from randomising this position. Thus, this position constitutes a case where a target interaction position is not randomised. In contrast, the position A4 was also defined to be randomised since it showed less than 30% conservation. Therefore positions A4, A6, A8, and A9 and positions B6 and B9 were randomised in the LRR module. The chosen subset of the amino acids at the randomised positions largely reflected the physicochemical properties of naturally occurring ones and therefore all charged and some H-bond forming and aromatic amino acids known to support binding in many instances were chosen. At the same time, the decision was taken to allow larger amino acids only in the A-type LRR unit positions and only smaller ones at the B-type LRR unit positions minimising steric hindrance in an alternating context. Thus, the obtained repeat sequence motif at this stage can be described as follows

```
A-type LRR consensus 1 3 5 7 9 11 13 15 17 19 21 23 25 27
RLE1L1L112GLTAAG4KDLASVLRANP
(SEQ ID NO: 21)
where 1 is D, E, N, Q, S, R, K, W, Y
and 2 is N or S or T
and 4 is L or M or V B-type LRR consensus 1..3 5 7 9 11 13 15 17 19 21 23 25 27 29
SLREL3LS3NELGDAGVRLLLEGLL#PGT
(SEQ ID NO: 22)
where 3 is G, S, D, N, H or T
and # is D or Q
```

Thus, randomisation at eight positions resulted in $2.8\times10^5$ independent RI repeat module pairs. In other words, the synthesis of molecules satisfying the above described repeat sequence motif will create about 300000 independent but highly homologous members. Another position analysed in detail is in the loop region on top of both LRR repeat units, namely position 11. Since the consensus in both A-type and B-type LRR unit was 36% and 25% respectively, the occurrence of pairs of amino acids was checked. In the B-type LRR unit, charged amino acids were slightly preferred at position 11 and a lysine often occurred with an aspartate in the A-type LRR unit. This putative salt bridge was believed to increase stability and solubility of the designed LRR module and was therefore chosen. Another possibility (glycine at A11 and glutamate at B11) was dismissed for fear of too high flexibility. The choice at position A14 was between alanine and glutamate, where the latter was again chosen to enhance the solubility and the correct orientation the hydrophilic outer shell. Similarly, the position B22 suggested either glutamate or glutamine, where the latter was chosen since it seemed to better match the serine at A22 defined previously.

Finally, position 26 was subject to scrutiny, where the choice was between alanine at A26 together with glutamine at B26 on the one hand, and serine at A26 together with aspartate at B26. The latter variant was adopted to again enhance the solubility of the LRR module.

Thus, the RI repeat motif pair looks as follows (alterations are printed bold)

```
A-type LRR consensus 1 3 5 7 9 11 13 15 17 19 21 23 25 27
RLE1L1L112DLTEAG4KDLASVLRSNP
(SEQ ID NO: 23)
where 1 is D, E, N, Q, S, R, K, W, Y
and 2 is N or S or T
and 4 is L or M or V B-type LRR consensus 1 3 5 7 9 11 13 15 17 19 21 23 25 27 29
SLREL3LS3NKLGDAGVRLLLQGLLDPGT
(SEQ ID NO: 24)
where 3 is G, S, D, N, H or T
```

5) Designing a Repeat Domain Derived from the LRR of Mammalian RI

Assembling multiple repeat modules into a domain is straightforward. Here, we undertook an approach involving two different restriction enzymes creating compatible overhangs (cf. FIG. 6). Thus, the direction of the ligation can simply be controlled by redigesting the ligation products, where only correctly ligated molecules are not cut.

Additionally, we chose to complement the assembled LRR modules by N- and C-terminal capping modules designed to shield the putative joint hydrophobic core of the repeat domain from the surrounding solvent. The analysis of the mammalian RI proteins revealed that the first and the last LRR units differed significantly from the consensus described above (FIGS. 5c and 5d). For simplicity, the corresponding capping units of the human RI were cloned with slight modifications and are henceforth referred to as capping modules. Thus, amino acids 1 to 28 for the N-terminal capping module and amino acids 427 to 460 of human RI for the C-terminal module were used, and a short linker encoding the amino acid residues PYAR (SEQ ID NO: 75 was introduced between the N-terminal capping module and the RI repeat module pairs to match the length requirements.

When the devised amino acid consensus was reverse translated into a DNA sequence the following parameters were taken into account: No undesired restriction enzyme recognition sequences were allowed within the repeat module pair and the codon usage was optimized for expression in *E. coli*.

6) Preparation of the Expression Plasmids

To obtain the N-terminal module flanked by appropriate restriction digestion sites, the DNA of pTRP-PRI (Lee and Vallee, 1989) was amplified with oligonucleotides MTS2 and MTS4 (Table 1) giving PCR-fragment N. Thus, at the 5'-end, an NcoI and a BamHI were introduced, whereas the 3'-end featured a BssHII and a HindIII site. The resulting DNA fragment is shown with translated amino acids in the correct frame (above the boxed part in FIG. 8).

The PCR-fragment N was ligated into the NcoI and HindIII sites of pTFT74 (Ge et al., 1995) yielding plasmid pTFT_N (FIG. 9a). At the same time, an N-terminal Flag-tag and a 6xHis-tag (SEQ ID NO: 76 were introduced. Several vectors were derived from pTFT_N for the insertion of the above described repeat modules. The NcoI-HindIII insert of pTFT_N was cloned into pQE60 (QIAgen, Hilden, Germany) prepared with the same restriction digestion enzymes (giving plasmid pQE_N). The BamHI-HindIII insert of pTFT_N (that is without N-terminal Flag-tag and the 6xHis-tag) (SEQ ID NO: 76 was cloned into a pQE60 derivative downstream of the lambda phage protein D gene insert in frame to yield a C-terminally fused repeat domain (giving plasmid pQE-pD_N).

The pTFT derivatives feature a T7 polymerase promotor under a lac operator, whereas the pQE derivatives offer a T5 polymerase promotor under the same control system. Lambda phage protein D as N-terminal fusion partner was chosen to increase the solubility and expression (Forrer and Jaussi, 1998).

7) Synthesis of the Repeat Module Libraries

Oligonucleotides MTS7 and MTS9 were partly assembled from trinucleotides (Virnekäs et al., 1994) all other oligonucleotides were synthesised with standard techniques.

The strategy presented below describes a way to obtain polymers of DNA fragments in a defined direction using palindromic restriction enzymes and ligation. One such possibility is to use the restriction enzymes BssHII and MluI (FIG. 6) which create compatible overhangs. If DNA fragments with the same overhang but different original recognition sites are religated a new combined site (named * in FIG. 6 and FIG. 7a to 7c) will be formed which cannot be digested by either of the original enzymes (FIG. 6). However, the ligation of identical ends leads to the original recognition site and these molecules can therefore be distinguished by restriction digestion. Other pairs of restriction enzymes with compatible overhangs are well known to those skilled in the art.

The following step numbering refers to the one used in FIG. 7a to c.

(Step I) To obtain the first library of repeat modules the partly randomised oligonucleotides MTS7, MTS8, MTS9, and MTS10 were assembled by PCR and were amplified with a 10-fold molar excess of MTS11b and MTS14b in one step (95 degrees for 2 min; then 20 cycles of 95 degrees for 15 sec; 55 degrees for 15 sec, and 72 degrees for 20 sec followed by 72 degrees, 1 min). In case of the LRR library described here, the initial PCR assembles the above described A/B pair into one module. The resulting DNA fragment is shown with translated amino acids in the correct frame (boxed part in FIG. 8, the oligonucleotides are shown as arrows).

(Step II) Separate extensive restriction digestion with either BamHI and MluI or BssHII was followed by ligation with T4 ligase (1 hour at room temperature and heat inactivation of the enzyme). The resulting ligation product was purified by low melting point agarose gel electrophoresis. The band corresponding to the dimer repeat module was isolated and the DNA was recovered after β-agarase digestion by ethanol precipitation.

(Step II) To amplify the dimer of repeat modules a second PCR reaction with primers T7pro and srpTFT1 (95 degrees for 2 min; then 15 cycles of 95 degrees for 15 sec; 50 degrees for 15 sec, 72 degrees for 40 sec followed by 72 degrees for 1 min) was performed. In case of the LRR library this step yielded two A/B pairs, that is four leucine-rich repeats. As 1 microgram template corresponding to about $10^{12}$ molecules was used for the LRR library the total theoretical diversity was still covered at this stage.

(Step IV) For the tetramer, the obtained DNA was again digested with either BamHI and MluI or BssHII. For longer polymers mixtures of single and doubly digested DNA fragments were prepared.

(Step V) The ligation, restriction digestion, and purification can be repeated until the desired number of repeat modules is obtained.

(Step VI) To obtain a DNA fragment with two different non-compatible restriction digestion sites at both ends for the directed and efficient cloning into a plasmid, the following "capping" strategy was devised. The C-terminal repeat unit of human RI was also amplified from plasmid pTRP-PRI by PCR thereby introducing a BssHII restriction site on the 5'-end and a HindIII restriction site at the 3'-end. The resulting DNA fragment is shown with translated amino acids in the correct frame (below the boxed part in FIG. 8).

The primers MTS5a and MTS3 were used in this PCR reaction (95 degrees for 2 min, then 20 cycles of 95 degrees for 15 sec, 45 degrees for 15 sec, and 72 degrees for 10 sec followed by 72 degrees for 1 min) and the product was OIAquick purified and restriction digested with BssHII.

(Step VII) The BssHII digested C-terminal repeat module was ligated to a MluI digested polymers by T4 ligase (1 hour at room temperature and heat inactivation of the enzyme). The subsequent extensive restriction digestion with BssHII, MluI, and HindIII ascertained the correct orientation of the modules. The mixture was separated by low melting point agarose gel electrophoresis and the desired bands were recovered as above. Finally, the recovered fragments were ligated into any of the BssHII-HindIII digested plasmids pTFT_N, pTFT-pD_N, pQE_N or pQE-pD_N. The resulting ligation mix was QIAquick purified and used for electroporation of XL10Gold cells prepared according to Sidhu et al. (2000).

The above described protocol results in different libraries of plasmids and two representative diagrams of such plasmids are shown (FIGS. 9b and 9c).

8) Characterization of the Repeat Module Protein Libraries

Standard DNA sequencing techniques were used to determine the DNA sequence of the expression plasmids. As an example the DNA sequence of clone D17 (compare expression in FIGS. 11c, 11d, and 12d) is given (FIGS. 10a and 10b). The N-terminal module and the four repeat modules as well as the C-terminal module are indicated. Expression was essentially performed as described (QIAgen "QIAexpressionist") and the soluble and insoluble proteins of single clones and/or pools of clones after sonification were separated by SDS-PAGE analysis and Coomassie stained (FIGS. 11a-d). Western blot analysis was performed according to the protocol supplied by the manufacturer. Antibody anti-Flag M2 (Sigma) was used for the constructs without N-terminal protein D, whereas anti-RGS-His (Qiagen) was used for constructs with N-terminal protein D (FIGS. 12a-d).

Purifications (FIGS. 13 and 14), CD spectrometry (FIG. 15) and size exclusion chromatography (FIG. 16) were carried out as described in example 2.

9) Selection of (Poly)Peptide/Proteins which Inhibit Bacterial Toxins

Various bacterial toxins are known to occur together with the corresponding antitoxin because even a moderate level of toxin alone cannot be tolerated in bacteria. Therefore, the gene of CcdB (Jensen et al., 1995) was cloned into a low copy plasmid of the pZ series with a tightly repressed tetracyclin promotor in a tetracyclin repressor strain like DH5☐Z1 (Lutz and Bujard, 1997), XL10Gold or XL1Blue. In parallel, wild-type barnase (Hartley, 1988) and the barnaseH102K mutant with 0.1% activity (Jucovic and Hartley, 1996) were cloned. Chemically competent cells with one of these toxin plasmids were prepared as described (Inoue et al., 1990) and electroporation competent cells harbouring one of these toxin plasmids were prepared as described (Sidhu et al., 2000). For the selection of plasmids encoding a toxin inhibitor cells were transformed with the LRR-based library, plated on selective plates (LB medium supplied with 50 mg/L ampicilin, 20 mg/L kanamycin, 40 micromolar IPTG, and 30 microgram/L anhydrotetracyclin), and grown at either 25 or 37° C. To confirm that inhibitory properties are plasmid-linked, the pQE derivatives were reisolated and retransformed.

Screening for Efficiently Folding Constructs

GFP has been successfully used as a folding reporter when fused to the C-terminus of the target protein (Waldo et al., 1999). Rapidly aggregating targets do not allow folding of C-terminally fused GFP and colonies can be screened in UV light. The fluorescence of GFP correlated with the amount of correctly folded protein. In our strategy, GFP was cloned into the NheI and EcoRI sites designed at the C-terminus obtained by PCR amplification using MTS5a and MTS6 and again pTRP-PRI as template. Hereby, a 12 amino acid linker GSAGSAAGSGEF (SEQ ID NO: 25) was introduced. The resulting DNA fragment is shown with translated amino acids in the correct frame (at the bottom in FIG. 8).

Selection for Constructs Without Stop-codons

To reduce the number of frameshifts and stop-codons after the construction of the library, the constructs were cloned upstream of a linker connecting to the chloramphenicol resistance gene and viable clones were selected on plates.

Selection for Binding Targets Using Display Techniques

To identify binding partners in vitro, both ribosome display (Hanes et al., 1998) and phage display (Dunn, 1996) was used. Binding partners were RNase A and Onconase (Wu et al., 1993b) from the RNase superfamily and protein D (Forrer and Jaussi, 1998), an unrelated small polypeptide.

Selection for Binding Targets Using the Protein Complementation Assay

To identify binding partners, an *E. coli* genomic library was fused to the DHFR1 fragment (Pelletier et al., 1998), whereas the LRR-based library was fused next to DHFR2. Selection on M9 plates containing trimethoprim lead to interacting molecules.

DNA Module Shuffling for the Improvement of the Obtained Constructs

For further evolutionary improvements, the obtained constructs were subjected to DNA shuffling (Stemmer, 1994) and back-crossing. Thus, improvements could be enriched and mutations without effect were lost.

Example 2

Collection of (Poly)Peptide/Proteins Comprising Repeat Modules Derived from Ankyrin Repeat Units A method for the generation of designed ankyrin repeat proteins according to the present invention is described. The method allows the construction of ankyrin repeat proteins of various length by using an N-terminal ankyrin capping module, two or several ankyrin repeat modules and a C-terminal ankyrin capping module.

The definition of the ankyrin repeat motif which was the basis for the generation of a collection of ankyrin repeat modules in EXAMPLE 1 is described below. The analysis leading to the ankyrin repeat motif included search of public databases for naturally existing ankyrin repeat proteins as well as structural analysis of ankyrin repeat proteins with known three-dimensional structure. By way of this analysis, a sequence, motif for the ankyrin repeat modules was derived and ankyrin capping modules were derived. Furthermore, the positions of framework and target interaction residues were determined for the ankyrin repeat motif. To generate a library of ankyrin repeat modules, 17 out of 20 natural amino acids were allowed at the positions of target interaction residues in the ankyrin repeat motif. The positions of the framework residues were specified to certain amino acids each. The resulting peptide sequences were reverse translated such that the codon usage was optimal in *Escherichia coli* but did not create unwanted restriction sites. Oligonucleotides were designed to allow assembly PCR of the ankyrin repeat modules. Trinucleotide oligonucleotides (Virnekäs et al., 1994) as well as conventional oligonucleotides were used (Tables 2 and 3). Similarly, the N- and C-terminal ankyrin capping modules were generated by assembly PCR using conventional oligonucleotides (Table 2). The resulting PCR products all contained type IIs restriction enzyme recognition sites (FIG. 17) at those ends that subsequently would be connected to the DNA of the next/previous repeat- (or capping) module (FIG. 18). When cut by the respective restriction enzymes, the generated compatible ends of the modules could be ligated in frame in a unidirectional way. Hence, the N-terminal capping module could be ligated to one or several ankyrin repeat modules and the ligation products could be ligated to the C-terminal ankyrin capping module. As the DNA differed in defined positions, the method allowed the simultaneous assembly of a diverse set of DNA molecules encoding a collection of ankyrin repeat proteins. Members of the resulting collections of ankyrin repeat proteins were characterised by expression, purification, circular dichroism spectroscopy, denaturation experiments, size exclusion chromatography as well as crystallisation. The experiments demonstrated that unselected members of this ankyrin repeat protein library can be expressed in the reductive environment of the cytoplasm at high levels in a soluble and folded conformation.

Definition of the Ankyrin Repeat Motif Sequence

PROCEDURE and RESULT: The ankyrin repeat motif used as an example for the present invention was derived from ankyrin repeat protein sequence analysis as well as from structural analysis of ankyrin repeat proteins with known three-dimensional structure (date: August 2000).

The SMART database (Schultz et al., 2000) was first searched for amino acid sequences of ankyrin repeat units. A Clustal-W (Thompson et al., 1994) alignment of 229 ankyrin repeat units served as template for the determination of an ankyrin repeat unit consensus "A" (FIG. 19). Consensus "A" was determined by calculation of the residue-frequency occurrence for each position of the alignment of ankyrin repeat units. The 229 ankyrin repeat units considered did not contain inserts or deletions compared to a previously stated general ankyrin repeat unit consensus sequence (Sedgwick and Smerdon, 1999). Consensus "A", however, included only residues 3 to 32 (FIG. 19) of the 33 amino acids long consensus sequence of Sedgwick and Smerdon (1999). To further refine the consensus and define the lacking positions, a BLAST (Altschul et al., 1990) search against GenBank (Benson et al., 2000) was performed using default parameters. For this search, consensus "A" was submitted in a circularly permutated form with position 20 as first amino acid (FIG. 19). The missing or ambiguous positions were filled with residues that had highest frequency in a consensus of ankyrin repeat units of ankyrin repeat proteins with known three-dimensional structure (manually aligned, statistics as described above). The first 200 of the resulting BLAST hits were manually aligned and the ankyrin repeat unit consensus "A" was refined by residue frequency analysis as stated above yielding consensus "B" (FIG. 19). Consensus "B" was confirmed by an identical analysis of the pfam database (Bateman et al., 1999; data not shown).

The final ankyrin repeat unit consensus "C" (FIG. 19) was obtained by integration of the methods mentioned in this paragraph. Published three-dimensional structures of ankyrin repeat proteins were visually inspected to further decide which amino acids were optimal at a certain position. The three-dimensional structure showing highest homology to ankyrin repeat unit consensus "B", the mouse GA-binding protein beta 1 subunit (AC: 2981726, pdb: 1AWC; Batchelor et al., 1998), was the guideline in most instances, but other structures such as human p18 (AC: 4139830, pdb: 1IHB; Venkatamarani et al., 1998) were also considered. The mutual dependence of pairs, triplets and quatruplets of amino acids in naturally occurring ankyrin repeat unit sequences was also used to further develop or assure consensus "B". Furthermore, modeling approaches (insightII package; Informax Inc., USA) including homology modeling and energy minimisations have been performed and the consensus sequence was developed towards optimal cavity avoidance and packing optimisation. It was further ensured that the secondary structure propensity (O'Neil and DeGrado, 1990; Chou and Fasman, 1978) of each residue of the consensus matched the secondary structure at the corresponding position in natural ankyrin repeat units. In addition, the secondary structure was analysed and verified using PhD-prediction (Rost, B., 1996). Protein stability and protease resistance of the consensus was then analysed using PEST (Rogers et al., 1986; Swiss Institute of Bioinformatics, Switzerland) and peptidesort of GCG (Accelrys, USA; Womble, D. D., 2000) and the consensus was predicted to be sufficiently stable.

Critical residues during the definition of ankyrin repeat unit consensus "B" (FIG. 19) to consensus "C" (FIG. 19) were positions 16, 17, 18,19, 21, 22, 25 and 26. Position 16 was finally determined to be a histidine, since it makes buried H-bonds from its position to the previous repeat. The leucine at position 17 was finally preferred to other amino acids since it stabilises the interface of two repeat modules. The glutamate of position 18 was chosen as repeated glutamates and aspartates occur in human p18 at this position. Similarly, the glutamate at position 21 occurs in multiple successive copies in mouse GA-binding protein. Lysine 25 was preferred to other amino acids as the basic residues arginine and lysine occur repeatedly in mouse GA-binding protein as well. For position 26, the compromise of taking any of the three amino acids histidine, tyrosine or asparagine was chosen, as these amino acids all fulfil the requirements for this position. Accordingly, the positions 19 and 22 were occupied by isoleucine or valine and valine or leucine, respectively, as these residues fitted equally well.

The finally determined ankyrin repeat unit consensus "C" (FIG. 19) served as basis for the ankyrin repeat modules. The sequence of the ankyrin repeat motif is shown in FIG. 20. For cloning reasons the motif is based on a circularly permutated consensus "C". In order to match the consensus numbering scheme used in FIG. 19 and used by Sedgwick and Smerdon (1999), the numbers of the positions in the ankyrin repeat motif were circularly permutated in parallel to the amino acid sequence. The ankyrin repeat motif has a length of 33 amino acids, whereof 27 positions were defined to be framework residues and 6 positions were defined as target interaction residues. The positions of framework residues were defined using ankyrin repeat unit consensus "C". Analyses of three-dimensional structures showed that positions 2, 3, 5, 13, 14 and 33 of the ankyrin repeat units are often involved in protein-protein interactions and hence constitute the target interaction residues. This was also suggested by the high variability these positions showed during ankyrin repeat unit consensus definition. For the ankyrin repeat modules, these residues were defined to be any of the 17 amino acids A, D, E, F, H, I, K, L, M, N, Q, R, S, T, V, W and Y.

Thus, the number of independent members of the collection of ankyrin repeat modules can be calculated to be $3 \cdot 17^6 = 72'412'707$.

Definition of the Ankyrin Capping Modules

PROCEDURE and RESULT: As the derived ankyrin repeat motif showed high homology to the beta 1 subunit of the mouse GA-binding protein (GABP beta 1; AC: 2981726; Batchelor et al., 1998), the N- and C-terminal ankyrin repeat capping units (repeats 1 and 5 according to Batchelor et al., 1998) of the latter protein were chosen as a basis for the N- and C-terminal capping modules. Both the N- and C-terminal ankyrin capping module had to be changed compared to the mouse GA-binding protein beta 1 capping units. The N-terminal GA-binding protein beta 1 capping unit was modified in its loop to sterically fit the design of the ankyrin repeat motif. The C-terminal GA-binding protein beta 1 capping unit was modified at several positions. Parts of the loop of repeat 4 and the beta hairpin connecting repeat 4 and 5 of GA-binding protein beta 1 (Batchelor et al., 1998) had to be included into the C-terminal capping module for cloning reasons. Thereby, the loop and the beta hairpin were modified to sterically fit the design of the ankyrin repeat motif. The modifications can be seen in FIG. 21, where GABP beta 1 is aligned to E3-5, a member of a protein library according to the present invention (see below).

Experimental Procedures

For all following sections of EXAMPLE A, techniques were performed according to protocols as described in Sambrook, J., Fritsch, E. F. and Maniatis, T. (1989; Molecular cloning: a laboratory manual. Cold spring laboratory press, N.Y.) or in volumes 1 to 4 of Ausubel, F. M., Brent, R., Kingston, R. E., Moore, D. D., Seidman, J. G., Smith, J. A. and Struhl, K. (1994; Current protocols in molecular biology. John Wiley and Sons, Inc., N.Y.) or in volumes 1 and 2 of Coligan, J. E., Dunn, B. M., Ploegh, H. L, Speicher, D. W. and Wingfield, P. T. (1995; Current protocols in protein science. John Wiley and Sons, Inc., N.Y.).

Synthesis of DNA Encoding Ankyrin Repeat Proteins According to the Present Invention PROCEDURE and RESULT: Oligonucleotides INT1 and INT2 were partly assembled from trinucleotides (Virnekäs et al., 1994) and were obtained from MorphoSys (Germany). All other oligonucleotides were synthesised with standard techniques and were from Microsynth (Switzerland, cf. Tables 2 and 3). Oligonucleotides for amplification of DNA were used at 100 μM stock concentration, while the ones used as templates were used as 10 μM stock. Enzymes and buffers were from New England Biolabs (USA) or Fermentas (Lithuania). Cloning strain was *E. Coli* XL1-Blue (Stratagene).

The ankyrin repeat modules were generated by assembly PCR using oligonucleotides (1 μl each) INT1, INT2, INT3, INT4, INT5 and INT6a [5 min 95° C., 20·(30 sec 95° C., 1 min 50° C., 30 sec 72° C.), 5 min 72° C.] and Vent DNA polymerase in its standard buffer supplemented with additional 3.5 mM $MgSO_4$ in a final volume of 50 μl.

The N-terminal ankyrin capping module was prepared by assembly PCR using oligonucleotides (1 μl each) EWT1, EWT2, TEN3 and INT6 [5 min 95° C., 30·(30 sec 95° C., 1 min 40° C., 30 sec 72° C.), 5 min 72° C.] and Vent DNA polymeras in its standard buffer in 50 μl reaction volume. The resulting DNA was cloned via BamHI/HindIII into pQE30 (QIAgen, Germany). The DNA sequence was verified using standard techniques. The C-terminal ankyrin capping module was prepared accordingly, but by using oligonucleotides WTC1, WTC2, WTC3 and INT5.

The ligation of the DNA encoding an ankyrin repeat protein from single ankyrin repeat modules and ankyrin repeat capping modules is represented schematically in FIG. 18. To assemble ankyrin repeat proteins, the cloned N-terminal ankyrin capping module was PCR-amplified using oligonucleotides TEN3 and INT6a (conditions as above for the N-terminal ankyrin capping module). The DNA was purified using the OIAquick DNA purification kit (QIAgen, Germany), cut with BsaI and repurified using the same kit. The N-terminal ankyrin capping module was then ligated onto BpiI cut and purified ankyrin repeat module. This directional cloning was possible since the cutting sequences of BpiI and BsaI, two type IIs restriction enzymes which recognise a DNA sequence different from the cutting sequence (FIG. 17), was chosen to be asymmetric but compatible with each other. The ligation product, termed N1, was gel-purified (LMP-agarose, β-agarase, sodiumacetate/ethanol precipitation) and PCR-amplified using oligonucleotides (1 μl each) EWT3 and INT6b [5 min 95° C., 20·(30 sec 95° C., 30 sec 50° C., 30 sec 72° C.), 5 min 72° C.] and Vent DNA polmerase in its standard buffer in 50 μl reaction volume. The amplified product was purified using QIAquick, cleaved with BsaI and purified again. The subsequent ligation to BpiI cut ankyrin repeat modules started a new cycle of elongation which was repeated until the desired number of ankyrin repeat modules was added to the N-terminal ankyrin capping module (termed N2, N3, N4 etc.). DNA pieces corresponding to PCR-amplified N2, N3 and N4 were then cut with BsaI and ligated to a previously BpiI-cut PCR product of the cloned C-terminal ankyrin capping module. This yielded DNA molecules encoding N2C, N3C and N4C ankyrin repeat protein libraries. The final products were PCR amplified using 1 μl of each EWT3 and WTC3 each [5 min 95° C., 25·(30 sec 95° C., 30 sec 50° C., 1 min 72° C.), 5 min 72° C.] and cloned via BamHI/HindIII into pQE30 (QIAgen).

Protein Expression and Purification

PROCEDURE: *E. coli* XL1-Blue (Stratagene) was used as strain for the expression of ankyrin repeat proteins of different lengths. Two clones corresponding to N2C (named E2-5 and E2-17), two clones corresponding to N3C (E3-5 and E3-19) and two clones corresponding to N4C (E4-2 and E4-8) were randomly chosen and analysed further. 25 ml of stationary overnight cultures (LB, 1% glucose, 100 mg/l ampicillin; 37° C.) of these clones were used to inoculate 1 l cultures (same media as preculture). At $OD_{600}=0.7$, the cultures were induced with 300 μM IPTG and incubated for four hours. Samples were taken at various timepoints and analysed via SDS-PAGE (see FIG. 22). The cultures were centrifuged and the resulting pellets were taken up in 40 ml $TBS_{500}$ (50 mM TrisHCl, pH 8.0, 500 mM NaCl) and sonified. Then the lysates were supplemented with 10% glycerole and 20 mM imidazole and recentrifuged. The resulting supernatant was used for purification over a His-tag column (2.5 cl column volume) according to the manufacturer (QIAgen, Germany).

RESULTS: Cell fractionation experiments showed that all ankyrin repeat proteins were soluble expressed with yields of 200 mg/l culture (FIG. 22). His-tag purification led to pure protein in a single purification step (FIG. 23). The proteins integrity was further confirmed by mass spectroscopy (not shown). The soluble expression indicates proper folding of the designed repeat proteins.

Size Exclusion Chromatography

PROCEDURE: The six purified samples described above were analysed on a Superdex 75 column (Amersham Pharmacia Biotech, USA) using a Pharmacia SMART system at a flow rate of 60 μl/min and TBS 150 (50 mM TrisHCl, pH 7.5; 150 mM NaCl) as running buffer. Standards were □-amylase (Sigma) and the phage proteins pD and SHP (Yang et al., 2000). As an example the elution profile of a N3C-library member, E3-5, is shown in FIG. 24.

RESULTS: The elution profile showed that the proteins investigated were in most cases exclusively monomeric, while a minor number of protein samples (E2-17 and E4-8) showed multimerised, but soluble species in addition to the monomers. The retention measured by gel filtration indicated that the investigated proteins are folded and not random coils.

CD Spectroscopy

PROCEDURE: The circular dichroism spectra of a randomly chosen ankyrin repeat protein generated according to the present invention (E3-5, a N3C molecule) were recorded either in 10 mM sodium phosphate buffer pH 6.5 (native) or 20 mM sodium phosphate buffer pH 6.5 and 6 M Guanidinium hydrochloride (denatured) using a Jasco J-715 instrument [Jasco, Japan; 10 nm/s, 8 sec response, 0.2 nm data pitch, 2 nm band width, 195-250 nm (native) or 212-250 nm (denatured), three accumulations, measurements in triplicates, 1 mm cuvette]. The CD signal was converted to mean residue elipticity using the concentration of the sample determined spectrophotometrically at 280 nm under denaturing conditions.

RESULTS: E3-5 shows an alpha-helical spectrum under native conditions with minima at 208 nm and 222 nm. The secondary structure is lost in 6 M Guanidinium hydrochloride (FIG. 25). This indicates the proper formation of secondary structure elements in E3-5.

Denaturation Behaviour

PROCEDURE: The denaturation behaviour of randomly chosen ankyrin repeat proteins generated according to the present invention (E2-5, E3-5 and E4-8, FIG. 22) was measured via circular dichroism spectroscopy basically as indicated in FIG. 25 but using different buffers. Guanidiniumhydrochloride denaturation curves were measured by CD spectroscopy at 220 nm using the different proteins incubated in different concentrations of guanidinium hydrochloride in 20 mM NaPO$_4$ pH6.5, 100 mM NaCl, overnight at room temperature. The circular dichroism signal at 220 nm was measured for each sample in triplicates.

RESULTS: The denaturation curves of E2-5, E3-5 and E4-8 against different concentrations of guanidinium hydrochloride are shown in FIG. 26. The midpoint of denaturation is in a range of 2.5 to 3.8 M guanidiniumhydrochloride. Hence, the secondary structure is lost only at high concentrations of denaturing agent indicating a relatively high stability of the investigated molecules.

Crystallisation

PROCEDURE and RESULT: The ankyrin repeat protein E3-5, a N3C library member according to the present invention, was crystallised in 20% PEG 6000, 100 mM MES/NaOH pH 6.0 in five days at 20° C., hanging droplet (2 µl protein and 2 µl buffer mixed; 500 µl buffer reservoir) from a solution of 9 mg Protein per ml in TBS 50 (50 mM TrisHCl, pH 8.0, 50 mM NaCl; cf. FIG. 27). The crystal refracted to 3 Å in preliminary X-ray experiments (not shown).

Tables

Table 1: Oligonucleotides used for the cloning of the library derived from human RI;

Table 2: Oligonucleotides used for the generation of ankyrin repeat modules according to example 2;

Table 3: Oligonucleotides used for the generation of the N- and C-terminal ankyrin capping modules as well as for the cloning of ankyrin repeat proteins containing more than one ankyrin repeat module according to the present invention.

TABLE 1

Oligonucleotides used for the cloning of the library derived from human RI (SEQ ID NOS 26-37), respectively in order of appearance, peptide (SEQ ID NO: 77 and 6X-His tag SEQ ID NO:76)

| name | sequence in 5'-3' direction (restrictionsites)[1] | description |
| --- | --- | --- |
| MTS2 | CATGCCATGGACTACAAGGATCATCACCATCACCATCACGGATCCctgga catccag (NcoI, BamHI) | fwd[2] PCR primer to obtain human RI with initial Flag-tag MDYKD and 6xHis-tag |
| MTS4 | GCATAAGCTTATCACTCGAGGCGCGCGTAGGGctgctggagcagagg (HindIII, XhoI, BssHII) | rev[2] PCR primer to obtain N-term. RI unit |
| MTS3 | GCATAAGCTTATCAggagatgaccc (HindIII) | rev[2] PCR primer to obtain human RI |
| MTS5a | CATGCCATGGGcgcgCctcgagcagctggtcc (NcoI, BssHII, XhoI) | fwd[2] PCR primer for new C-term. unit |
| MTS7 | TTGGCGCGCCTGGAGNNNCTGNNNCTGNNNNNNNNNgacctcacc gaggccggc (BssHII)[3] | fwd[2] assembly left, 4 library elements, 1 codon for S, N, T |
| MTS8 | ccgcaggctcgggttggaGCGGAGCACGCTGGCCAGGTCCTTCANgccgg cctcggtgaggtc | rev[2] assembly left, 1 codon for L, M, V |
| MTS9 | tccaacccgagcctgcggGAGCTGNNNCTGAGCNNNaacaagctcggcgatgca | fwd[2] assembly right, 2 library elements |
| MTS10 | CCGCTCGAGACGCGTGCCGGGGTCCAGCAGCCCCTGCAAGAG CAGCCGCACGCCtgcatcgccgagcttgtt (XhoI) | rev[2] assembly right |
| MTS11b | TAATACGACTCACTATAGGGtbggcgcgcctggag (BssHII) | fwd[2] PCR primer to amplify the assembly |
| MTS14b | GGCTTTGTTAGCAGCCGGATCCtcgagacgcgtgccggggtc (BamHI, XhoI, MluI) | rev[2] PCR primer to amplify the assembly |
| T7pro | AAATtaatacgactcactataggg | fwd[2] PCR primer to amplify library dimer |
| srpTFT1 | CGggctttgttagcagccgg | rev[2] PCR primer to amplify library dimer |

[1]small letters indicate regions designed for annealing
[2]abbreviations: fwd - forward; rev - reverse.
[3]NNN stands for a mixture of trinucleotides.

TABLE 2

Oligonucleotides used for the generation of ankyrin repeat modules according to example 2
(SEQ ID NOS 38-43, respectively in order of appearance)

| Name | Sequence in 5'-3' direction (restriction sites) | Description |
| --- | --- | --- |
| INT1 | CTGACGTTAACGCTNNNGACNNNNNNGGTNNNACTCCGCTGCACCTGGC[1] | Forward primer (1) for the assembly of ankyrin repeat modules |
| INT2 | ACTCCGCTGCACCTGGCTGCTNNNNNNGGTCACCTGGAAATCG[1] | Forward primer (2) for the assembly of ankyrin repeat modules |
| INT3 | AACGTCAGCACCGTDCTTCAGCAGAACTTCAACGATTTCCAGGTGACC[2] | Reverse primer (1) for the assembly of ankyrin repeat modules |
| INT4 | AGCAGCCAGGTGCAGCGGAGT | Reverse primer (2) for the assembly of ankyrin repeat modules |
| INT5 | TTCCGCGGATCCTAGGAAGACCTGACGTTAACGCT (BamHI, BpiI) | Forward primer for ankyrin repeat module and C-terminal ankyrin capping module amplification (BpiI) |
| INT6a | TTTGGGAAGCTTCTAAGGTCTCACGTCAGCACCGT (HindIII, BsaI) | Reverse primer for ankyrin repeat module and N-terminal ankyrin capping module amplification (BsaI) |

[1] NNN stands for a mixture of trinucleotides encoding the amino acids A, D, E, F, H, I, K, L, M, N, Q, R, S, T, V, W and Y (Virnekäs et al., 1994).
[2] D represents A, T or G.

TABLE 3

Oligonucleotides used for the generation of the N- and C-terminal ankyrin capping modules as well as for the cloning of ankyrin repeat proteins containing more than one ankyrin repeat module
(SEQ ID NOS 44-52, respectively in order of appearance)

| Name | Sequence in 5'-3' direction (restriction sites) | Description |
| --- | --- | --- |
| INT6b | TTTGGGAAGCTTCTAAGGTCTC (HindIII, BsaI) | Reverse primer for the amplification of ankyrin repeat modules having a INT6a sequence at the 3' end |
| INT6 | TTTGGGAAGCTTCTAGAAGACAACGTCAGCACCGT (HindIII, BpiI) | Reverse primer for amplification of the N-terminal ankyrin capping module (BpiI) |
| EWT1 | TTCCGCGGATCCGACCTGGGTAAGAAACTGCTGGAAGCTGCTCGTGCTGGTCAGGACGACGAAG | Forward primer for the assembly of the N-terminal ankyrin capping module |
| EWT2 | AACGTCAGCACCGTTAGCCATCAGGATACGAACTTCGTCGTCCTGACC | Reverse primer for the assembly of the N-terminal ankyrin capping module |
| EWT3 | TTCCGCGGATCCGACCTGGG (BamHI) | Forward primer (1) for the amplification of sequences containing the N-terminal ankyrin capping module |
| TEN3 | TTCCGCGGATCCG (BamHI) | Forward primer (2) for the amplification of sequences containing the N-terminal ankyrin capping module |
| WTC1 | CTGACGTTAACGCTCAGGACAAATTCGGTAAGACCGCTTTCGACATCTCCATCGACAACGGTAACGAGG | Forward primer for the assembly of the C-terminal ankyrin capping module |
| WTC2 | TTGCAGGATTTCAGCCAGGTCCTCGTTACCGTTGTC | Reverse primer for the assembly of the C-terminal ankyrin capping module |
| WTC3 | TTTGGGAAGCTTCTATTGCAGGATTTCAGC (HindIII) | Reverse primer (1) for the amplification of sequences containing the C-terminal ankyrin capping module |

REFERENCES

Altschul, S. F., Gish, W., Miller, W., Myers, E. W., and Lipman, D. J. (1990). Basic local alignment search tool. J Mol Biol 215, 403-410.

Ausubel, F. M., Brent, R., Kingston, R. E., Moore, D. D., Sedman, J. G., Smith, J. A. and Struhl, K. eds. (1999). Current Protocols in Molecular Biology. N.Y.: John Wiley and Sons.

Batchelor, A. H., Piper, D. E., de la Brousse, F. C., McKnight, S. L., and Wolberger, C. (1998). The structure of GABPalpha/beta: an ETS domain-ankyrin repeat heterodimer bound to DNA. Science 279, 1037-1041.

Bateman, A., Birney, E., Durbin, R., Eddy, S. R., Finn, R. D., and Sonnhammer, E. L. (1999). Pfam 3.1: 1313 multiple alignments and profile HMMs match the majority of proteins. Nucleic Acids Res 27, 260-262.

Benson, D. A., Karsch-Mizrachi, I., Lipman, D. J., Ostell, J., Rapp, B. A., and Wheeler, D. L. (2000). GenBank. Nucleic Acids Res 28,15-18.

Berks, A. H. (1994). Patent information in biotechnology. Trends Biotechnol. 12, 352-64.

Blázquez, M., Fominaya, J. M., and Hofsteenge, J. (1996). Oxidation of sulfhydryl groups of ribonuclease inhibitor in epithelial cells is sufficient for its intracellular degradation. *J Biol Chem* 271, 18638-18642.

Bork, P. (1993). Hundreds of ankyrin-like repeats in functionally diverse proteins: mobile modules that cross phyla horizontally? *Proteins* 17, 363-374.

Breeden, L., and Nasmyth, K. (1987). Similarity between cell-cycle genes of budding yeast and fission yeast and the Notch gene of Drosophila. Nature 329, 651-654.

Chen, C. Z., and Shapiro, R. (1997). Site-specific mutagenesis reveals differences in the structural bases for tight binding of RNase inhibitor to angiogenin and RNase A. *Proc Natl Acad Sci USA* 94,1761-1766.

Chou, P. Y., and Fasman, G. D. (1978). Prediction of the secondary structure of proteins from their amino acid sequence. Adv Enzymol Relat Areas Mol Biol 47,45-148.

Dunn, I. S. (1996). Phage display of proteins. *Curr Opin Biotechnol* 7, 547-553.

Forrer, P., and Jaussi, R. (1998). High-level expression of soluble heterologous proteins in the cytoplasm of *Escherichia coli* by fusion to the bacteriophage lambda head protein D. Gene 224, 45-52.

Ge, L., Knappik, A., Pack, P., Freund, C. and Plückthun, A. (1995). Expressing antibodies in *Escherichia coli*. Antibody Engineering. A Practical Approach (Ed. C. A. K. Borrebaeck). IRL Press, Oxford, pp. 229-266.

Gorina, S., and Pavletich, N. P. (1996). Structure of the p53 tumor suppressor bound to the ankyrin and SH3 domains of 53BP2. Science 274, 1001-1005.

Groves, M. R. and Barford, D. (1999). Topological characteristics of helical repeat proteins. Curr Opin Struct Biol 9, 383-389.

Hanes, J., Jermutus, L., Weber-Bornhauser, S., Bosshard, H. R., and Plückthun, A. (1998). Ribosome display efficiently selects and evolves high-affinity antibodies in vitro from immune libraries. *Proc Natl Acad Sci USA* 95, 14130-14135.

Hartley, R. W. (1988). Barnase and Barstar. Expression of its cloned inhibitor permits expression of a cloned ribonuclease. *J Mol Biol* 202, 913-915.

Hiatt, A. and Ma, J. K. (1993). Characterization and applications of antibodies produced in plants. *Int Rev Immunol* 10, 139-152.

Hiatt, A. (1990). Antibodies produced in plants. *Nature* 344, 469-470.

Hillig, R. C., Renault, L., Vetter, I. R., Drell, T. t., Wittinghofer, A., and Becker, J. (1999). The crystal structure of rna1p: a new fold for a GTPase-activating protein. *Mol Cell* 3, 781-791.

Hochuli, E., Bannwarth, W., Döbeli, H., Gentz, R. and Stüber, D. (1988). Genetic approach to facilitate purification of recombinant proteins with a novel metal chelate adsorbent. *Bio/Technology* 6, 1321-1325.

Hofsteenge, J., Kieffer, B., Matthies, R., Hemmings, B. A., and Stone, S. R. (1988). Amino acid sequence of the ribonuclease inhibitor from porcine liver reveals the presence of leucine-rich repeats. *Biochemistry* 27, 8537-8544.

Hopp, T. P., Prickett, K. S., Price, V. L., Libby, R. T., March, C. J., Cerretti, D. P., Urdal, D. L. and Conlon, P. J. (1988). A short polypeptide marker sequence useful for recombinant protein identification and purification. *Bio/Technology* 6, 1204-1210.

Horwitz, A. H., Chang, C. P., Better, M., Hellstrom, K. E. and Robinson, R. R. (1988). Secretion of functional antibody and Fab fragment from yeast cells. *Proc Natl Acad Sci USA* 85, 8678-8682.

Huxford, T., Huang, D. B., Malek, S., and Ghosh, G. (1998). The crystal structure of the IκBα/NF-κB complex reveals mechanisms of NF-κB inactivation. *Cell* 95, 759-770.

Inoue, H., Nojima, H., and Okayama, H. (1990). High efficiency transformation of *Escherichia coli* with plasmids. *Gene* 96, 23-28.

Jacobs, M. D. and Harrison, S. C. (1998). Structure of an IκBα/NF-κB complex. *Cell* 95, 749-758.

Jeffrey, P. D., Tong, L., and Pavletich, N. P. (2000). Structural basis of inhibition of CDK-cyclin complexes by INK4 inhibitors. Genes Dev 14, 3115-3125.

Jensen, R. B., Grohmann, E., Schwab, H., Diaz-Orejas, R., and Gerdes, K. (1995). Comparison of ccd of F, parDE of RP4, and parD of R1 using a novel conditional replication control system. Mol Microbiol 17, 211-220.

Jucovic, M. and Hartley, R. W. (1996). Protein-protein interaction: a genetic selection for compensating mutations at the barnase-barstar interface. *Proc Natl Acad Sci USA* 93, 2343-2347.

Kajava, A. V. (1998). Structural diversity of leucine-rich repeat proteins. *J Mol Biol* 277, 519-527.

Kay, B. K., Winter, J. and McCafferty, J., eds. (1996). Phage display of peptides and proteins: a laboratory manual. Academic Press, Inc., San Diego.

Kawanomoto, M., Motojima, K., Sasaki, M., Hattori, H., and Goto, S. (1992). cDNA cloning and sequence of rat ribonuclease inhibitor, and tissue distribution of the mRNA. *Biochim Biophys Acta* 1129, 335-338.

Kirkham, P. M., Neri, D., and Winter, G. (1999). Towards the design of an antibody that recognises a given protein epitope. *J Mol Biol* 285, 909-915.

Knappik, A. and Plückthun, A. (1994). An improved affinity tag based on the FLAG peptide for detection and purification of recombinant antibody fragments. *Bio Techniques* 17, 754-761.

Kobe, B., and Deisenhofer, J. (1993). Crystal structure of porcine ribonuclease inhibitor, a protein with leucine-rich repeats. *Nature* 366, 751-756.

Kobe, B. and Deisenhofer, J. (1994). The leucine-rich repeat: a versatile binding motif. Trends Biochem.Sci. 19, 415-421.

Kobe, B., and Deisenhofer, J. (1995). A structural basis of the interactions between leucine-rich repeats and protein ligands. *Nature* 374, 183-186.

Kobe, B. (1996). Leucines on a roll. Nat Struct Biol 3, 977-980.

Kobe, B., and Deisenhofer, J. (1996). Mechanism of ribonuclease inhibition by ribonuclease inhibitor protein based on the crystal structure of its complex with ribonuclease A. *J Mol Biol* 264, 1028-1043.

Kobe, B. and Kajava, A. V. (2000). When protein folding is simplified to protein coiling: the continuum of solenoid protein structures. *Trends Biochem. Sci.* 25, 509-515.

Koradi, R., Billeter, M., and Wüthrich, K. (1996). MOLMOL: a program for display and analysis of macromolecular structures. *J Mol Graph* 14, 51-55, 29-32.

Ku, J., and Schultz, P. G. (1995). Alternate protein frameworks for molecular recognition. *Proc Natl Acad Sci USA* 92, 6552-6556.

Lee, F. S., and Vallee, B. L. (1989). Expression of human placental ribonuclease inhibitor in *Escherichia coli*. *Biochem Biophys Res Commun* 160,115-120.

Lee, F. S., Auld, D. S., and Vallee, B. L. (1989). Tryptophan fluorescence as a probe of placental ribonuclease inhibitor binding to angiogenin. *Biochemistry* 28, 219-224.

Lee, F. S., Fox, E. A., Zhou H. M., Strydorn, D. J., and Vallee, B. L. (1988). Primary structure of human placental ribonuclease inhibitor [published erratum appears in Biochemistry 1989 Aug. 22;28(17):7138]. *Biochemistry* 27, 8545-8553.

Lindner, P., Guth, B., Wülfing, C., Krebber, C., Steipe, B., Müller, F. and Plückthun, A. (1992). Purification of native proteins from the cytoplasm and periplasm of *Escherichia coli* using IMAC and histidine tails: a comparison of proteins and protocols. Methods: A Companion to Methods Enzymol. 4, 41-56.

Lutz, R. and Bujard, H. (1997). Independent and tight regulation of transcriptional units in *Escherichia coli* via the LacR/O, the TetR/O, and AraC/$I_1$-$I_2$ regulatory elements. *Nucleic Acids Res* 25, 1203-1210.

Lux, S. E., John, K. M., and Bennett, V. (1990). Analysis of cDNA for human erythrocyte ankyrin indicates a repeated structure with homology to tissue-differentiation and cell-cycle control proteins. Nature 344, 3642.

Malek, S., Huxford, T., and Ghosh, G. (1998). Ikappa Balpha functions through direct contacts with the nuclear localization signals and the DNA binding sequences of NF-kappaB. J Biol Chem 273, 25427-25435.

Marino, M., Braun, L., Cossart, P., and Ghosh, P. (1999). Structure of the InlB leucine-rich repeats, a domain that triggers host cell invasion by the bacterial pathogen L. monocytogenes. *Mol Cell* 4, 1063-1072.

Nygren, P. A., and Uhlen, M. (1997). Scaffolds for engineering novel binding sites in proteins. *Curr Opin Struct Biol* 7, 463-469.

Marino, M., Braun, L., Cossart, P., and Ghosh, P. (2000). A framework for interpreting the leucine-rich repeats of the Listeria internalins. Proc Nati Acad Sci USA 97, 8784-8788.

Nyyssönen, E., Penttila, M., Harkki, A., Saloheimo, A., Knowles, J. K. and Keranen, S. (1993). Efficient production of antibody fragments by the filamentous fungus *Trichoderma reesei*. Bio/Technology 11, 591-595.

O'Neil, K. T., and DeGrado, W. F. (1990). A thermodynamic scale for the helix-forming tendencies of the commonly occurring amino acids. Science 250, 646-651.

Papageorgiou, A. C., Shapiro, R., and Acharya, K. R. (1997). Molecular recognition of human angiogenin by placental ribonuclease inhibitor—an X-ray crystallographic study at 2.0 A resolution. *EMBO J* 16, 5162-5177.

Pelletier, J. N., Campbell-Valois, F. X., and Michnick, S. W. (1998). Oligomerization domain-directed reassembly of active dihydrofolate reductase from rationally designed fragments. Proc Natl Acad Sci USA 95, 12141-12146.

Potter, K. N., Li, Y. and Capra, J. D. (1993). Antibody production in the baculovirus expression system. *Int Rev Immunol* 10, 103-112.

Price, S. R., Evans, P. R., and Nagai, K. (1998). Crystal structure of the spliceosomal U2B"-U2A' protein complex bound to a fragment of U2 small nuclear RNA. *Nature* 394, 645-650.

Proba, K., Honegger, A., and Plückthun, A. (1997). A natural antibody missing a cysteine in VH: consequences for thermodynamic stability and folding. *J Mol Biol* 265, 161-172.

Ridder, R., Schmitz, R., Legay, F. and Gram, H. (1995). Generation of rabbit monoclonal antibody fragments from a combinatorial phage display library and their production in the yeast *Pichia pastoris*. *Bio/Technology* 13, 255-260.

Rogers, S., Wells, R., and Rechsteiner, M. (1986). Amino acid sequences common to rapidly degraded proteins: the PEST hypothesis. Science 234, 364-368.

Rost, B. (1996). PHD: predicting one-dimensional protein structure by profile-based neural networks. Methods Enzymol 266, 525-39.

Sambrook, J., Fritsch, E. F. and Maniatis, T. (1989). Molecular Cloning: A laboratory manual, Cold Spring Harbor Laboratory Press, Cold Spring Harbor, USA.

Schmidt, T. G. and Skerra, A. (1993). The random peptide library-assisted engineering of a C-terminal affinity peptide, useful for the detection and purification of a functional Ig Fv fragment. *Protein Eng* 6, 109-122.

Schmidt, T. G. and Skerra, A. (1994). One-step affinity purification of bacterially produced proteins by means of the "Strep tag" and immobilised recombinant core streptavidin. *J Chromatogr A* 676, 337-345.

Schmidt, T. G., Koepke, J., Frank, R., and Skerra, A. (1996). Molecular interaction between the Strep-tag affinity peptide and its cognate target, streptavidin. *J Mol Biol* 255, 753-766.

Schultz, J., Copley, R. R., Doerks, T., Ponting, C. P., and Bork, P. (2000). SMART: a web-based tool for the study of genetically mobile domains. Nucleic Acids Res 28, 231-234.

Sedgwick, S. G. and Smerdon, S. J. (1999). The ankyrin repeat: a diversity of interactions on a common structural framework. *Trends Biochem Sci* 24, 311-316.

Sequeira, E., McEntyre, J., and Lipman, D. (2001). PubMed Central decentralized. Nature 410, 740.

Sidhu, S. S., Lowman, H. B., and Wells, J. A. (2000). Phage display for selection of novel binding peptides. *Methods Enzymol*, in the press.

Smith G. P. (1985). Filamentous fusion phage: novel expression vectors that display cloned antigens on the virion surface. *Science* 228, 1315-1317.

Stemmer, W. P. (1994). DNA shuffling by random fragmentation and reassembly: in vitro recombination for molecular evolution. *Proc Natl Acad Sci USA* 91, 10747-10751.

Suzuki, F., Goto, M., Sawa, C., Ito, S., Watanabe, H., Sawada, J., and Handa, H. (1998). Functional interactions of transcription factor human GA-binding protein subunits. J Biol Chem 273, 29302-29308.

Thompson, J. D., Higgins, D. G., and Gibson, T. J. (1994). CLUSTAL W: improving the sensitivity of progressive multiple sequence alignment through sequence weighting, position-specific gap penalties and weight matrix choice. Nucleic Acids Res 22, 4673-4680.

Trill, J. J., Shatzman, A. R. and Ganguly, S. (1995). Production of monoclonal antibodies in COS and CHO cells. *Curr Opin Biotechnol* 6, 553-560.

Venkataramani, R., Swaminathan, K., and Marmorstein, R. (1998). Crystal structure of the CDK4/6 inhibitory protein p18INK4c provides insights into ankyrin-like repeat structure/function and tumor-derived p16INK4 mutations. Nat Struct Biol 5, 74-81.

Virnekäs, B., Ge, L., Plückthun, A., Schneider, K. C., Welinhofer, G., and Moroney, S. E. (1994). Trinucleotide phosphoramidites: ideal reagents for the synthesis of mixed oligonucleotides for random mutagenesis. *Nucleic Acids Res* 22, 5600-5607.

Volkov, A. A. and Arnold, F. H. (2000). Methods for in vitro DNA recombination and random chimeragenesis. Methods Enzymol 328, 447-456.

Waldo, G. S., Standish B. M., Berendzen, J., and Terwilliger, T. C. (1999). Rapid protein-folding assay using green fluorescent protein. *Nat Biotechnol* 17, 691-695.

Ward, V. K., Kreissig, S. B., Hammock, B. D. and Choudary, P. V. (1995). Generation of an expression library in the baculovirus expression vector system. *J Virol Methods* 53, 263-272.

Whitelam, G. C., Cockburn, W. and Owen, M. R. (1994). Antibody production in transgenic plants. *Biochem Soc Trans* 22, 940-944.

Wilson, D. S. and Keefe, A. D. (2000). Random Mutagenesis by PCR. In Current Protocols in Molecular Biology. F. M. Ausubel, R. Brent, R. E. Kingston, D. D. Moore, J. G. Seidman, J. A. Smith, and K. Strubel, eds. (N.Y.: Wiley).

Womble, D. D. (2000). GCG: The Wisconsin Package of sequence analysis programs. Methods Mol Biol 132, 3-22.

Wu, X. C., Ng, S. C., Near, R. I. and Wong, S. L. (1993a). Efficient production of a functional single-chain anti-digoxin antibody via an engineered *Bacillus subtilis* expression-secretion system. *Bio/Technology* 11, 71-76.

Wu, Y., Mikulski, S. M., Ardelt, W., Rybak, S. M., and Youle, R. J. (1993b). A cytotoxic ribonuclease. Study of the mechanism of onconase cytotoxicity. *J Biol Chem* 268, 10686-10693.

Yang, F., Forrer, P., Dauter, Z., Conway, J. F., Cheng, N., Cerritelli, M. E., Steven, A. C., Plückthun, A., and Wlodawer, A. (2000). Novel fold and capsid-binding properties of the lambda-phage display platform protein gpD. Nat Struct Biol 7, 230-237.

Yang, W. P., Green, K., Pinz-Sweeney, S., Briones, A. T., Burton, D. R., and Barbas, C. F., 3rd (1995). CDR walking mutagenesis for the affinity maturation of a potent human anti-HIV-I antibody into the picomolar range. *J Mol Biol* 254, 392-403.

Zhang, B., and Peng, Z. (2000). A minimum folding unit in the ankyrin repeat protein p16(INK4). J Mol Biol 299, 1121-1132.

The invention claimed is:

1. A collection of nucleic acid molecules encoding a collection of repeat proteins, each repeat protein comprising a repeat domain, which comprises a set of consecutive repeat modules,
wherein each of said repeat modules is derived from one or more repeat units, wherein said repeat units are ankyrin repeats and wherein said repeat units comprise framework residues, which contribute to the folding topology of said repeat unit or contribute to an interaction with a neighboring repeat unit, and target interaction residues, which contribute to an interaction with a target substance,
- wherein said repeat proteins differ from other repeat proteins in said collection in at least one amino acid position of the repeat modules, and
- wherein said derivation of each of said repeat modules is carried out by an analysis comprising the steps of
  - (a) identifying said repeat units;
  - (b) determining a repeat sequence motif by structural and sequence analysis of said repeat units,
- wherein said structural and sequence analysis includes the identification of said framework residues and said target interaction residues of said repeat units; and
  - (c) constructing the repeat module so that it comprises the repeat sequence motif of (b).

2. The collection of claim 1, wherein each of said repeat modules has an amino acid sequence, wherein at least 70% of the amino acid residues are either
   (i) consensus amino acid residues deduced from the amino acid residues found at the corresponding positions on alignment of at least two repeat units; or
   (ii) the amino acid residues found at the corresponding positions in a repeat unit.

3. The collection of claim 1, wherein said set consists of between two and about 30 repeat modules.

4. The collection of claim 1 or 3, wherein said repeat modules are directly connected without an intervening amino acid sequence.

5. The collection of claim 1 or 3, wherein said repeat modules are connected by a peptide or polypeptide linker.

6. The collection of claim 1 or 3, wherein said repeat domain further comprises an N- and/or a C-terminal capping module having an amino acid sequence different from any one of said repeat modules.

7. The collection of claim 1, wherein said set consists of one type of repeat modules of the same length of said module and consisting of the same number and composition of the fixed amino acid positions.

8. The collection of claim 1, wherein said set consists of two different types of repeat modules, wherein each said type of repeat module is of the same length and consists of the same number and composition of the fixed amino acid positions, and wherein said two different types differ in at least the length or the number or the composition of the fixed amino acid positions.

9. The collection of claim 1, wherein said set comprises in said repeat domain a pair of two different types of consecutive repeat modules wherein each said type of repeat module is of the same length and consists of the same number and composition of the fixed amino acid positions, wherein said two different types differ in at least the length or the number or the composition of the fixed amino acid positions.

10. The collection of claim 1, wherein each of said repeat modules comprises the ankyrin repeat sequence motif

D11G1TPLHLAA11GHLEIVEVLLK2GADVNA1,
    (SEQ ID NO: 4)

wherein 1 represents an amino acid residue selected from the group:

A, D, E, F, H, I, K, L, M, N, Q, R, S, T, V, W and Y;

wherein 2 represents an amino acid residue selected from the group:

H, N and Y.

11. The collection of claim 10, wherein the collection comprises nucleic acids generated by exchange of nucleotides such that one or more of the amino acid residues in said consensus sequences are replaced by an amino acid residue found at the corresponding position on alignment of a repeat unit.

12. The collection of claim 1, 3 or 10, wherein said nucleic acid molecules comprise identical nucleic acid sequences of at least 9 nucleotides between said repeat modules.

13. The collection of claim 12, wherein said identical nucleic acid sequences allow assembly of said nucleic acid molecules by PCR technology.

14. The collection of claim 1, 3 or 10, wherein there are nucleic acid sequences between said modules, and each of said nucleic acid sequences between said modules comprises a restriction enzyme recognition sequence.

15. The collection of claim 1, 3 or 10, wherein there are nucleic acid sequences between said repeat modules and each of said nucleic acid sequences between said repeat modules comprises a nucleic acid sequence formed from cohesive ends created by two restriction enzymes.

16. A collection of recombinant nucleic acid molecules comprising a collection of nucleic acid molecules according to claim 1, 3 or 10.

* * * * *

SEQUENCE LISTING

```
<160> NUMBER OF SEQ ID NOS: 77

<210> SEQ ID NO 1
<211> LENGTH: 48
<212> TYPE: PRT
<213> ORGANISM: Artificial Sequence
<220> FEATURE:
<223> OTHER INFORMATION: Description of Artificial Sequence: Synthetic
                        ankyrin repeat consensus sequence
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (12)
<223> OTHER INFORMATION: Variable amino acid with an apolar sidechain
<220> FEATURE:
<221> NAME/KEY: MOD_RES
<222> LOCATION: (13)..(14)
<223> OTHER INFORMATION: Variable amino acid
<220> FEATURE:
<221> NAME/KEY: MOD_RES
<222> LOCATION: (15)..(24)
<223> OTHER INFORMATION: Variable amino acid or a deletion
<220> FEATURE:
<221> NAME/KEY: MOD_RES
<222> LOCATION: (26)
<223> OTHER INFORMATION: Variable amino acid with a polar sidechain
<220> FEATURE:
<221> NAME/KEY: MOD_RES
<222> LOCATION: (27)
<223> OTHER INFORMATION: Variable amino acid
<220> FEATURE:
<221> NAME/KEY: MOD_RES
<222> LOCATION: (28)
<223> OTHER INFORMATION: Variable amino acid with a polar sidechain
<220> FEATURE:
<221> NAME/KEY: MOD_RES
<222> LOCATION: (29)
<223> OTHER INFORMATION: Variable amino acid with an apolar sidechain
<220> FEATURE:
<221> NAME/KEY: MOD_RES
<222> LOCATION: (31)
<223> OTHER INFORMATION: Variable amino acid with a polar sidechain
<220> FEATURE:
<221> NAME/KEY: MOD_RES
<222> LOCATION: (32)
<223> OTHER INFORMATION: Variable amino acid
<220> FEATURE:
```

```
<221> NAME/KEY: MOD_RES
<222> LOCATION: (35)
<223> OTHER INFORMATION: Variable amino acid with a polar sidechain
<220> FEATURE:
<221> NAME/KEY: MOD_RES
<222> LOCATION: (36)
<223> OTHER INFORMATION: Variable amino acid
<220> FEATURE:
<221> NAME/KEY: MOD_RES
<222> LOCATION: (39)..(43)
<223> OTHER INFORMATION: Variable amino acid or a deletion
<220> FEATURE:
<221> NAME/KEY: MOD_RES
<222> LOCATION: (48)
<223> OTHER INFORMATION: Variable amino acid

<400> SEQUENCE: 1

Asp Xaa Xaa Gly Xaa Thr Pro Leu His Leu Ala Xaa Xaa Xaa Xaa
 1               5                  10                  15

Xaa Xaa Xaa Xaa Xaa Xaa Xaa Xaa Gly Xaa Xaa Xaa Xaa Val Xaa Xaa
            20                  25                  30

Leu Leu Xaa Xaa Gly Ala Xaa Xaa Xaa Xaa Xaa Asp Val Asn Ala Xaa
        35                  40                  45

<210> SEQ ID NO 2
<211> LENGTH: 33
<212> TYPE: PRT
<213> ORGANISM: Artificial Sequence
<220> FEATURE:
<223> OTHER INFORMATION: Description of Artificial Sequence: Synthetic
      ankyrin repeat consensus sequence
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (12)..(14)
<223> OTHER INFORMATION: Variable amino acid
<220> FEATURE:
<221> NAME/KEY: MOD_RES
<222> LOCATION: (16)..(18)
<223> OTHER INFORMATION: Variable amino acid
<220> FEATURE:
<221> NAME/KEY: MOD_RES
<222> LOCATION: (21)
<223> OTHER INFORMATION: Variable amino acid
<220> FEATURE:
<221> NAME/KEY: MOD_RES
<222> LOCATION: (25)..(26)
<223> OTHER INFORMATION: Variable amino acid
<220> FEATURE:
<221> NAME/KEY: MOD_RES
<222> LOCATION: (33)
<223> OTHER INFORMATION: Variable amino acid

<400> SEQUENCE: 2

Asp Xaa Xaa Gly Xaa Thr Pro Leu His Leu Ala Xaa Xaa Xaa Gly Xaa
 1               5                  10                  15

Xaa Xaa Val Val Xaa Leu Leu Leu Xaa Xaa Gly Ala Asp Val Asn Ala
            20                  25                  30

Xaa

<210> SEQ ID NO 3
<211> LENGTH: 33
<212> TYPE: PRT
<213> ORGANISM: Artificial Sequence
```

```
<220> FEATURE:
<223> OTHER INFORMATION: Description of Artificial Sequence: Synthetic
      ankyrin repeat sequence motif
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (12)..(14)
<223> OTHER INFORMATION: Variable amino acid
<220> FEATURE:
<221> NAME/KEY: MOD_RES
<222> LOCATION: (16)..(18)
<223> OTHER INFORMATION: Variable amino acid
<220> FEATURE:
<221> NAME/KEY: MOD_RES
<222> LOCATION: (21)
<223> OTHER INFORMATION: Variable amino acid
<220> FEATURE:
<221> NAME/KEY: MOD_RES
<222> LOCATION: (25)..(26)
<223> OTHER INFORMATION: Variable amino acid
<220> FEATURE:
<221> NAME/KEY: MOD_RES
<222> LOCATION: (33)
<223> OTHER INFORMATION: Variable amino acid

<400> SEQUENCE: 3

Asp Xaa Xaa Gly Xaa Thr Pro Leu His Leu Ala Xaa Xaa Xaa Gly Xaa
 1               5                  10                  15

Xaa Xaa Ile Val Xaa Val Leu Leu Xaa Xaa Gly Ala Asp Val Asn Ala
                 20                  25                  30

Xaa

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      ankyrin repeat sequence motif
<220> FEATURE:
<221> NAME/KEY: MOD_RES
<222> LOCATION: (2)..(3)
<223> OTHER INFORMATION: An amino acid residue selected from the
      group: Ala, Asp, Glu, Phe, His, Ile, Lys, Leu,
      Met, Asn, Gln, Arg, Ser, Thr, Val, Trp and Tyr
<220> FEATURE:
<221> NAME/KEY: MOD_RES
<222> LOCATION: (5)
<223> OTHER INFORMATION: An amino acid residue selected from the
      group: Ala, Asp, Glu, Phe, His, Ile, Lys, Leu,
      Met, Asn, Gln, Arg, Ser, Thr, Val, Trp and Tyr
<220> FEATURE:
<221> NAME/KEY: MOD_RES
<222> LOCATION: (13)..(14)
<223> OTHER INFORMATION: An amino acid residue selected from the
      group: Ala, Asp, Glu, Phe, His, Ile, Lys, Leu,
      Met, Asn, Gln, Arg, Ser, Thr, Val, Trp and Tyr
<220> FEATURE:
<221> NAME/KEY: MOD_RES
<222> LOCATION: (26)
<223> OTHER INFORMATION: An amino acid residue selected from the
      group: His, Asn and Tyr
<220> FEATURE:
<221> NAME/KEY: MOD_RES
<222> LOCATION: (33)
<223> OTHER INFORMATION: An amino acid residue selected from the
      group: Ala, Asp, Glu, Phe, His, Ile, Lys, Leu,
      Met, Asn, Gln, Arg, Ser, Thr, Val, Trp and Tyr
```

<400> SEQUENCE: 4

Asp Xaa Xaa Gly Xaa Thr Pro Leu His Leu Ala Ala Xaa Xaa Gly His
1               5                   10                  15

Leu Glu Ile Val Glu Val Leu Leu Lys Xaa Gly Ala Asp Val Asn Ala
            20                  25                  30

Xaa

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      LRR consensus sequence
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)
<223> OTHER INFORMATION: Variable amino acid or a deletion
<220> FEATURE:
<221> NAME/KEY: MOD_RES
<222> LOCATION: (12)
<223> OTHER INFORMATION: Variable amino acid
<220> FEATURE:
<221> NAME/KEY: MOD_RES
<222> LOCATION: (13)
<223> OTHER INFORMATION: An aliphatic amino acid
<220> FEATURE:
<221> NAME/KEY: MOD_RES
<222> LOCATION: (14)..(15)
<223> OTHER INFORMATION: Variable amino acid
<220> FEATURE:
<221> NAME/KEY: MOD_RES
<222> LOCATION: (16)
<223> OTHER INFORMATION: Variable amino acid or a deletion
<220> FEATURE:
<221> NAME/KEY: MOD_RES
<222> LOCATION: (17)
<223> OTHER INFORMATION: An aliphatic amino acid
<220> FEATURE:
<221> NAME/KEY: MOD_RES
<222> LOCATION: (18)..(21)
<223> OTHER INFORMATION: Variable amino acid or a deletion
<220> FEATURE:
<221> NAME/KEY: MOD_RES
<222> LOCATION: (22)
<223> OTHER INFORMATION: An aliphatic amino acid
<220> FEATURE:
<221> NAME/KEY: MOD_RES
<222> LOCATION: (23)..(24)
<223> OTHER INFORMATION: Variable amino acid or a deletion
<220> FEATURE:
<221> NAME/KEY: MOD_RES
<222> LOCATION: (25)
<223> OTHER INFORMATION: An aliphatic amino acid
<220> FEATURE:
<221> NAME/KEY: MOD_RES
<222> LOCATION: (26)..(27)
<223> OTHER INFORMATION: Variable amino acid or a deletion

```
<220> FEATURE:
<221> NAME/KEY: MOD_RES
<222> LOCATION: (28)
<223> OTHER INFORMATION: Variable amino acid
<220> FEATURE:
<221> NAME/KEY: MOD_RES
<222> LOCATION: (29)..(30)
<223> OTHER INFORMATION: Variable amino acid or a deletion

<400> SEQUENCE: 5

Xaa Leu Xaa Xaa Leu Xaa Leu Xaa Xaa Asn Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa
            20                  25                  30

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      LRR consensus sequence
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<221> NAME/KEY: MOD_RES
<222> LOCATION: (18)..(19)
<223> OTHER INFORMATION: Variable amino acid
<220> FEATURE:
<221> NAME/KEY: MOD_RES
<222> LOCATION: (21)..(22)
<223> OTHER INFORMATION: Variable amino acid
<220> FEATURE:
<221> NAME/KEY: MOD_RES
<222> LOCATION: (23)
<223> OTHER INFORMATION: An aliphatic amino acid
<220> FEATURE:
<221> NAME/KEY: MOD_RES
<222> LOCATION: (25)..(28)
<223> OTHER INFORMATION: Variable amino acid

<400> SEQUENCE: 6

Xaa Leu Glu Xaa Leu Xaa Leu Xaa Xaa Cys Xaa Leu Thr Xaa Xaa Xaa
 1               5                  10                  15

Cys Xaa Xaa Leu Xaa Xaa Xaa Leu Xaa Xaa Xaa Xaa
            20                  25

<210> SEQ ID NO 7
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      LRR consensus sequence
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (15)
<223> OTHER INFORMATION: Variable amino acid
<220> FEATURE:
<221> NAME/KEY: MOD_RES
<222> LOCATION: (17)
<223> OTHER INFORMATION: An aliphatic amino acid
<220> FEATURE:
<221> NAME/KEY: MOD_RES
<222> LOCATION: (18)..(19)
<223> OTHER INFORMATION: Variable amino acid
<220> FEATURE:
<221> NAME/KEY: MOD_RES
<222> LOCATION: (21)..(23)
<223> OTHER INFORMATION: Variable amino acid
<220> FEATURE:
<221> NAME/KEY: MOD_RES
<222> LOCATION: (25)..(26)
<223> OTHER INFORMATION: Variable amino acid
<220> FEATURE:
<221> NAME/KEY: MOD_RES
<222> LOCATION: (28)..(29)
<223> OTHER INFORMATION: Variable amino acid

<400> SEQUENCE: 7

Xaa Leu Xaa Glu Leu Xaa Leu Xaa Xaa Asn Xaa Leu Gly Asp Xaa Gly
 1               5                  10                  15

Xaa Xaa Xaa Leu Xaa Xaa Xaa Leu Xaa Xaa Pro Xaa Xaa
             20                  25

<210> SEQ ID NO 8
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (4)
<223> OTHER INFORMATION: An amino acid residue selected from the
      group: Asp, Glu, Asn, Gln, Ser, Arg, Lys, Trp
      and Tyr
<220> FEATURE:
<221> NAME/KEY: MOD_RES
<222> LOCATION: (6)
<223> OTHER INFORMATION: An amino acid residue selected from the group:
      Asp, Glu, Asn, Gln, Ser, Arg, Lys, Trp and Tyr
<220> FEATURE:
<221> NAME/KEY: MOD_RES
<222> LOCATION: (8)..(9)
<223> OTHER INFORMATION: An amino acid residue selected from the group:
```

```
                       Asp, Glu, Asn, Gln, Ser, Arg, Lys, Trp and Tyr
<220> FEATURE:
<221> NAME/KEY: MOD_RES
<222> LOCATION: (10)
<223> OTHER INFORMATION: An amino acid residue selected from the group:
                       Asn, Ser and Thr
<220> FEATURE:
<221> NAME/KEY: MOD_RES
<222> LOCATION: (17)
<223> OTHER INFORMATION: An amino acid residue selected from the group:
                       Leu, Val and Met
<220> FEATURE:
<221> NAME/KEY: MOD_RES
<222> LOCATION: (34)
<223> OTHER INFORMATION: An amino acid residue selected from the group:
                       Gly, Ser, Asp, Asn, His and Thr
<220> FEATURE:
<221> NAME/KEY: MOD_RES
<222> LOCATION: (37)
<223> OTHER INFORMATION: An amino acid residue selected from the group:
                       Gly, Ser, Asp, Asn, His and Thr

<400> SEQUENCE: 8

Arg Leu Glu Xaa Leu Xaa Leu Xaa Xaa Xaa Asp Leu Thr Glu Ala Gly
 1               5                  10                  15

Xaa Lys Asp Leu Ala Ser Val Leu Arg Ser Asn Pro Ser Leu Arg Glu
            20                  25                  30

Leu Xaa Leu Ser Xaa Asn Lys Leu Gly Asp Ala Gly Val Arg Leu Leu
        35                  40                  45

Leu Gln Gly Leu Leu Asp Pro Gly Thr
        50                  55

<210> SEQ ID NO 9
<211> LENGTH: 171
<212> TYPE: DNA
<213> ORGANISM: Artificial Sequence
<220> FEATURE:
<223> OTHER INFORMATION: Description of Artificial Sequence: Synthetic
                       nucleic acid construct
<220> FEATURE:
<221> NAME/KEY: modified_base
<222> LOCATION: (10)..(12)
<223> OTHER INFORMATION: represents a codon encoding an amino acid
                       residue selected from the group: Asp, Glu, Asn,
                       Gln, Ser, Arg, Lys, Trp and Tyr
<220> FEATURE:
<221> NAME/KEY: modified_base
<222> LOCATION: (16)..(18)
<223> OTHER INFORMATION: represents a codon encoding an amino acid
                       residue selected from the group: Asp, Glu, Asn,
                       Gln, Ser, Arg, Lys, Trp and Tyr
<220> FEATURE:
<221> NAME/KEY: modified_base
<222> LOCATION: (22)..(24)
<223> OTHER INFORMATION: represents a codon encoding an amino acid
                       residue selected from the group: Asp, Glu, Asn,
                       Gln, Ser, Arg, Lys, Trp and Tyr
<220> FEATURE:
<221> NAME/KEY: modified_base
<222> LOCATION: (25)..(27)
<223> OTHER INFORMATION: represents a codon encoding an amino acid
                       residue selected from the group: Asp, Glu, Asn,
                       Gln, Ser, Arg, Lys, Trp and Tyr
<220> FEATURE:
<221> NAME/KEY: modified_base
<222> LOCATION: (28)..(30)
<223> OTHER INFORMATION: represents a codon encoding an amino acid
                       residue selected from the group: Asn, Ser and
                       Thr
<220> FEATURE:
<221> NAME/KEY: modified_base
<222> LOCATION: (49)..(51)
<223> OTHER INFORMATION: represents a codon encoding an amino acid
                       residue selected from the group: Leu, Val and
```

```
                                     Met
<220> FEATURE:
<221> NAME/KEY: modified_base
<222> LOCATION: (100)..(102)
<223> OTHER INFORMATION: represents a codon encoding an amino acid
                        residue selected from the group: Gly, Ser, Asp,
                        Asn, His and Thr
<220> FEATURE:
<221> NAME/KEY: modified_base
<222> LOCATION: (109)..(111)
<223> OTHER INFORMATION: represents a codon encoding an amio acid
                        residue selected from the group: Gly, Ser, Asp,
                        Asn, His and Thr

<400> SEQUENCE: 9
cgcctggagn nnctgnnnct gnnnnnnnnn gacctcaccg aggccggcnn naaggacctg      60
gccagcgtgc tccgctccaa cccgagcctg cgggagctgn nnctgagcnn naacaagctc    120
ggcgatgcag gcgtgcggct gctcttgcag gggctgctgg accccggcac g             171

<210> SEQ ID NO 10
<211> LENGTH: 171
<212> TYPE: DNA
<213> ORGANISM: Artificial Sequence
<220> FEATURE:
<223> OTHER INFORMATION: Description of Artificial Sequence: Synthetic
                        nucleic acid construct
<220> FEATURE:
<221> NAME/KEY: modified_base
<222> LOCATION: (10)..(12)
<223> OTHER INFORMATION: represents a codon encoding an amino acid
                        residue selected from the group: Asp, Glu, Asn,
                        Gln, Ser, Arg, Lys, Trp and Tyr
<220> FEATURE:
<221> NAME/KEY: modified_base
<222> LOCATION: (16)..(18)
<223> OTHER INFORMATION: represents a codon encoding an amino acid
                        residue selected from the group: Asp, Glu, Asn,
                        Gln, Ser, Arg, Lys, Trp and Tyr
<220> FEATURE:
<221> NAME/KEY: modified_base
<222> LOCATION: (22)..(24)
<223> OTHER INFORMATION: represents a codon encoding an amino acid
                        residue selected from the group: Asp, Glu, Asn,
                        Gln, Ser, Arg, Lys, Trp and Tyr
<220> FEATURE:
<221> NAME/KEY: modified_base
<222> LOCATION: (25)..(27)
<223> OTHER INFORMATION: represents a codon encoding an amino acid
                        residue selected from the group: Asp, Glu, Asn,
                        Gln, Ser, Arg, Lys, Trp and Tyr
<220> FEATURE:
<221> NAME/KEY: modified_base
<222> LOCATION: (28)..(30)
<223> OTHER INFORMATION: represents a codon encoding an amino acid
                        residue selected from the group: Asn, Ser and
                        Thr
<220> FEATURE:
<221> NAME/KEY: modified_base
<222> LOCATION: (49)..(51)
<223> OTHER INFORMATION: represents a codon encoding an amino acid
                        residue selected from the group: Leu, Val and
                        Met
<220> FEATURE:
<221> NAME/KEY: modified_base
<222> LOCATION: (100)..(102)
<223> OTHER INFORMATION: represents a codon encoding an amino acid
                        residue selected from the group: Gly, Ser, Asp,
                        Asn, His and Thr
<220> FEATURE:
<221> NAME/KEY: modified_base
<222> LOCATION: (109)..(111)
<223> OTHER INFORMATION: represents a codon encoding an amino acid
                        residue selected from the group: Gly, Ser, Asp,
                        Asn, His and Thr
```

```
<400> SEQUENCE: 10
cgcctggagn nnctgnnnct gnnnnnnnnn gacctcaccg aggccggcnn naaggacctg      60
gccagcgtgc tccgctccaa cccgagcctg cgggagctgn nnctgagcnn naacaagctc     120
ggcgatgcag gcgtgcggct gctcttgcag gggctgctgg accccggcac g             171

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (14)
<223> OTHER INFORMATION: Variable amino acid
<220> FEATURE:
<221> NAME/KEY: MOD_RES
<222> LOCATION: (16)
<223> OTHER INFORMATION: Variable amino acid
<220> FEATURE:
<221> NAME/KEY: MOD_RES
<222> LOCATION: (18)..(19)
<223> OTHER INFORMATION: Variable amino acid
<220> FEATURE:
<221> NAME/KEY: MOD_RES
<222> LOCATION: (21)
<223> OTHER INFORMATION: Variable amino acid
<220> FEATURE:
<221> NAME/KEY: MOD_RES
<222> LOCATION: (25)..(28)
<223> OTHER INFORMATION: Variable amino acid

<400> SEQUENCE: 11

Xaa Leu Glu Xaa Leu Xaa Leu Xaa Xaa Cys Xaa Leu Thr Xaa Ala Xaa
 1               5                  10                  15

Cys Xaa Xaa Leu Xaa Ser Val Leu Xaa Xaa Xaa Xaa
            20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (6)
```

```
<223> OTHER INFORMATION: Variable amino acid
<220> FEATURE:
<221> NAME/KEY: MOD_RES
<222> LOCATION: (9)
<223> OTHER INFORMATION: Variable amino acid
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (15)
<223> OTHER INFORMATION: Variable amino acid
<220> FEATURE:
<221> NAME/KEY: MOD_RES
<222> LOCATION: (17)..(19)
<223> OTHER INFORMATION: Variable amino acid
<220> FEATURE:
<221> NAME/KEY: MOD_RES
<222> LOCATION: (22)
<223> OTHER INFORMATION: Variable amino acid
<220> FEATURE:
<221> NAME/KEY: MOD_RES
<222> LOCATION: (25)..(26)
<223> OTHER INFORMATION: Variable amino acid
<220> FEATURE:
<221> NAME/KEY: MOD_RES
<222> LOCATION: (28)
<223> OTHER INFORMATION: Variable amino acid

<400> SEQUENCE: 12

Ser Leu Xaa Glu Leu Xaa Leu Ser Xaa Asn Xaa Leu Gly Asp Xaa Gly
 1               5                  10                  15

Xaa Xaa Xaa Leu Cys Xaa Gly Leu Xaa Xaa Pro Xaa Cys
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Arg or Lys
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (16)
<223> OTHER INFORMATION: Variable amino acid
<220> FEATURE:
<221> NAME/KEY: MOD_RES
<222> LOCATION: (18)
<223> OTHER INFORMATION: Variable amino acid
<220> FEATURE:
<221> NAME/KEY: MOD_RES
<222> LOCATION: (21)
<223> OTHER INFORMATION: Variable amino acid
<220> FEATURE:
```

```
<221> NAME/KEY: MOD_RES
<222> LOCATION: (28)
<223> OTHER INFORMATION: Variable amino acid

<400> SEQUENCE: 13

Xaa Leu Glu Xaa Leu Xaa Leu Xaa Xaa Cys Xaa Leu Thr Ala Ala Xaa
 1               5                  10                  15

Cys Xaa Asp Leu Xaa Ser Val Leu Arg Ala Asn Xaa
            20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
                        peptide construct
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (9)
<223> OTHER INFORMATION: Variable amino acid
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (17)..(19)
<223> OTHER INFORMATION: Variable amino acid
<220> FEATURE:
<221> NAME/KEY: MOD_RES
<222> LOCATION: (22)
<223> OTHER INFORMATION: Variable amino acid
<220> FEATURE:
<221> NAME/KEY: MOD_RES
<222> LOCATION: (25)..(26)
<223> OTHER INFORMATION: Variable amino acid
<220> FEATURE:
<221> NAME/KEY: MOD_RES
<222> LOCATION: (28)
<223> OTHER INFORMATION: Variable amino acid

<400> SEQUENCE: 14

Ser Leu Xaa Glu Leu Xaa Leu Ser Xaa Asn Xaa Leu Gly Asp Ala Gly
 1               5                  10                  15

Xaa Xaa Xaa Leu Cys Xaa Gly Leu Xaa Xaa Pro Xaa Cys
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
                        peptide construct
<220> FEATURE:
<221> NAME/KEY: MOD_RES
<222> LOCATION: (1)
<223> OTHER INFORMATION: Arg or Lys
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
```

<222> LOCATION: (8)
<223> OTHER INFORMATION: Variable amino acid
<220> FEATURE:
<221> NAME/KEY: MOD_RES
<222> LOCATION: (28)
<223> OTHER INFORMATION: Variable amino acid

<400> SEQUENCE: 15

Xaa Leu Glu Xaa Leu Trp Leu Xaa Asp Cys Gly Leu Thr Ala Ala Gly
 1               5                  10                  15

Cys Lys Asp Leu Cys Ser Val Leu Arg Ala Asn Xaa
             20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
       peptide construct
<220> FEATURE:
<221> NAME/KEY: MOD_RES
<222> LOCATION: (6)
<223> OTHER INFORMATION: Variable amino acid
<220> FEATURE:
<221> NAME/KEY: MOD_RES
<222> LOCATION: (9)
<223> OTHER INFORMATION: Asn or Ser
<220> FEATURE:
<221> NAME/KEY: MOD_RES
<222> LOCATION: (11)
<223> OTHER INFORMATION: Variable amino acid
<220> FEATURE:
<221> NAME/KEY: MOD_RES
<222> LOCATION: (18)
<223> OTHER INFORMATION: Variable amino acid
<220> FEATURE:
<221> NAME/KEY: MOD_RES
<222> LOCATION: (26)
<223> OTHER INFORMATION: Variable amino acid
<220> FEATURE:
<221> NAME/KEY: MOD_RES
<222> LOCATION: (28)
<223> OTHER INFORMATION: Variable amino acid

<400> SEQUENCE: 16

Ser Leu Arg Glu Leu Xaa Leu Ser Xaa Asn Xaa Leu Gly Asp Ala Gly
 1               5                  10                  15

Val Xaa Leu Leu Cys Glu Gly Leu Leu Xaa Pro Xaa Cys
             20                  25

<210> SEQ ID NO 17
<211> LENGTH: 28
<212> TYPE: PRT
<213> ORGANISM: Artificial Sequence
<220> FEATURE:
<223> OTHER INFORMATION: Description of Artificial Sequence: Synthetic
       peptide construct
<220> FEATURE:
<221> NAME/KEY: MOD_RES
<222> LOCATION: (1)
<223> OTHER INFORMATION: Arg or Lys

<400> SEQUENCE: 17

Xaa Leu Glu Lys Leu Trp Leu Glu Asp Cys Gly Leu Thr Ala Ala Gly
 1               5                  10                  15

Cys Lys Asp Leu Cys Ser Val Leu Arg Ala Asn Pro
             20                  25

<210> SEQ ID NO 18

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (9)
<223> OTHER INFORMATION: Asn or Ser
<220> FEATURE:
<221> NAME/KEY: MOD_RES
<222> LOCATION: (26)
<223> OTHER INFORMATION: Asp or Gln

<400> SEQUENCE: 18

Ser Leu Arg Glu Leu Asp Leu Ser Xaa Asn Glu Leu Gly Asp Ala Gly
 1               5                  10                  15

Val Arg Leu Leu Cys Glu Gly Leu Leu Xaa Pro Gly Cys
                20                  25

<210> SEQ ID NO 19
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (10)
<223> OTHER INFORMATION: Asn, Ser or Thr
<220> FEATURE:
<221> NAME/KEY: MOD_RES
<222> LOCATION: (17)
<223> OTHER INFORMATION: Leu, Met or Val

<400> SEQUENCE: 19

Arg Leu Glu Lys Leu Trp Leu Glu Asp Xaa Gly Leu Thr Ala Ala Gly
 1               5                  10                  15

Xaa Lys Asp Leu Ala Ser Val Leu Arg Ala Asn Pro
                20                  25

<210> SEQ ID NO 20
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (9)
<223> OTHER INFORMATION: Asn or Ser
<220> FEATURE:
<221> NAME/KEY: MOD_RES
<222> LOCATION: (26)
<223> OTHER INFORMATION: Asp or Gln

<400> SEQUENCE: 20

Ser Leu Arg Glu Leu Asp Leu Ser Xaa Asn Glu Leu Gly Asp Ala Gly
 1               5                  10                  15

Val Arg Leu Leu Leu Glu Gly Leu Leu Xaa Pro Gly Thr
                20                  25

<210> SEQ ID NO 21
<211> LENGTH: 28
<212> TYPE: PRT
<213> ORGANISM: Artificial Sequence
<220> FEATURE:
```

```
<223> OTHER INFORMATION: Description of Artificial Sequence: Synthetic
                       peptide construct
<220> FEATURE:
<221> NAME/KEY: MOD_RES
<222> LOCATION: (4)
<223> OTHER INFORMATION: Asp, Glu, Asn, Gln, Ser, Arg, Lys, Trp or Tyr
<220> FEATURE:
<221> NAME/KEY: MOD_RES
<222> LOCATION: (6)
<223> OTHER INFORMATION: Asp, Glu, Asn, Gln, Ser, Arg, Lys, Trp or Tyr
<220> FEATURE:
<221> NAME/KEY: MOD_RES
<222> LOCATION: (8)..(9)
<223> OTHER INFORMATION: Asp, Glu, Asn, Gln, Ser, Arg, Lys, Trp or Tyr
<220> FEATURE:
<221> NAME/KEY: MOD_RES
<222> LOCATION: (10)
<223> OTHER INFORMATION: Asn, Ser or Thr
<220> FEATURE:
<221> NAME/KEY: MOD_RES
<222> LOCATION: (17)
<223> OTHER INFORMATION: Leu, Val or Met

<400> SEQUENCE: 21

Arg Leu Glu Xaa Leu Xaa Leu Xaa Xaa Xaa Gly Leu Thr Ala Ala Gly
 1               5                  10                  15

Xaa Lys Asp Leu Ala Ser Val Leu Arg Ala Asn Pro
            20                  25

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
                       peptide construct
<220> FEATURE:
<221> NAME/KEY: MOD_RES
<222> LOCATION: (6)
<223> OTHER INFORMATION: Gly, Ser, Asp, Asn, His or Thr
<220> FEATURE:
<221> NAME/KEY: MOD_RES
<222> LOCATION: (9)
<223> OTHER INFORMATION: Gly, Ser, Asp, Asn, His or Thr
<220> FEATURE:
<221> NAME/KEY: MOD_RES
<222> LOCATION: (26)
<223> OTHER INFORMATION: Asp or Gln

<400> SEQUENCE: 22

Ser Leu Arg Glu Leu Xaa Leu Ser Xaa Asn Glu Leu Gly Asp Ala Gly
 1               5                  10                  15

Val Arg Leu Leu Leu Glu Gly Leu Leu Xaa Pro Gly Thr
            20                  25

<210> SEQ ID NO 23
<211> LENGTH: 28
<212> TYPE: PRT
<213> ORGANISM: Artificial Sequence
<220> FEATURE:
<223> OTHER INFORMATION: Description of Artificial Sequence: Synthetic
                       peptide construct
<220> FEATURE:
<221> NAME/KEY: MOD_RES
<222> LOCATION: (4)
<223> OTHER INFORMATION: Asp, Glu, Asn, Gln, Ser, Arg, Lys, Trp or Tyr
<220> FEATURE:
<221> NAME/KEY: MOD_RES
<222> LOCATION: (6)
<223> OTHER INFORMATION: Asp, Glu, Asn, Gln, Ser, Arg, Lys, Trp or Tyr
<220> FEATURE:
<221> NAME/KEY: MOD_RES
<222> LOCATION: (8)..(9)
```

```
<223> OTHER INFORMATION: Asp, Glu, Asn, Gln, Ser, Arg, Lys, Trp or Tyr
<220> FEATURE:
<221> NAME/KEY: MOD_RES
<222> LOCATION: (10)
<223> OTHER INFORMATION: Asn, Ser or Thr
<220> FEATURE:
<221> NAME/KEY: MOD_RES
<222> LOCATION: (17)
<223> OTHER INFORMATION: Leu, Met or Val

<400> SEQUENCE: 23

Arg Leu Glu Xaa Leu Xaa Leu Xaa Xaa Xaa Asp Leu Thr Glu Ala Gly
 1               5                  10                  15

Xaa Lys Asp Leu Ala Ser Val Leu Arg Ser Asn Pro
            20                  25

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (6)
<223> OTHER INFORMATION: Gly, Ser, Asp, Asn, His or Thr
<220> FEATURE:
<221> NAME/KEY: MOD_RES
<222> LOCATION: (9)
<223> OTHER INFORMATION: Gly, Ser, Asp, Asn, His or Thr

<400> SEQUENCE: 24

Ser Leu Arg Glu Leu Xaa Leu Ser Xaa Asn Lys Leu Gly Asp Ala Gly
 1               5                  10                  15

Val Arg Leu Leu Leu Gln Gly Leu Leu Asp Pro Gly Thr
            20                  25

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      amino acid linker

<400> SEQUENCE: 25

Gly Ser Ala Gly Ser Ala Ala Gly Ser Gly Glu Phe
 1               5                  10

<210> SEQ ID NO 26
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
catgccatgg actacaagga tcatcaccat caccatcacg gatccctgga catccag         57

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 27
gcataagctt atcactcgag gcgcgcgtag ggctgctgga gcagagg            47

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcataagctt atcaggagat gaccc            25

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
catgccatgg gcgcgcctcg agcagctggt cc            32

<210> SEQ ID NO 30
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(18)
<223> OTHER INFORMATION: A mixture of trinucleotides encoding Ser, Asn
      or Thr
<220> FEATURE:
<221> NAME/KEY: modified_base
<222> LOCATION: (22)..(24)
<223> OTHER INFORMATION: A mixture of trinucleotides encoding Ser, Asn
      or Thr
<220> FEATURE:
<221> NAME/KEY: modified_base
<222> LOCATION: (28)..(30)
<223> OTHER INFORMATION: A mixture of trinucleotides encoding Ser, Asn
      or Thr
<220> FEATURE:
<221> NAME/KEY: modified_base
<222> LOCATION: (31)..(33)
<223> OTHER INFORMATION: A mixture of trinucleotides encoding Ser, Asn
      or Thr
<220> FEATURE:
<221> NAME/KEY: modified_base
<222> LOCATION: (34)..(36)
<223> OTHER INFORMATION: A mixture of trinucleotides encoding Ser, Asn
      or Thr

<400> SEQUENCE: 30
ttggcgcgcc tggagnnnct gnnnctgnnn nnnnnngacc tcaccgaggc cggc            54

<210> SEQ ID NO 31
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)

<223> OTHER INFORMATION: represents a codon encoding Leu, Met or Val

<400> SEQUENCE: 31
ccgcaggctc gggttggagc ggagcacgct ggccaggtcc ttcangccgg cctcggtgag    60
gtc                                                                 63

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: A mixture of trinucleotides
<220> FEATURE:
<221> NAME/KEY: modified_base
<222> LOCATION: (34)..(36)
<223> OTHER INFORMATION: A mixture of trinucleotides

<400> SEQUENCE: 32
tccaacccga gcctgcggga gctgnnnctg agcnnnaaca agctcggcga tgca         54

<210> SEQ ID NO 33
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccgctcgaga cgcgtgccgg ggtccagcag cccctgcaag agcagccgca cgcctgcatc    60
gccgagcttg tt                                                       72

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
taatacgact cactataggg ttggcgcgcc tggag                              35

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggctttgtta gcagccggat cctcgagacg cgtgccgggg tc                      42

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 36
aaattaatac gactcactat aggg                                           24

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
                        oligonucleotide

<400> SEQUENCE: 37
cgggctttgt tagcagccgg                                                20

<210> SEQ ID NO 38
<211> LENGTH: 49
<212> TYPE: DNA
<213> ORGANISM: Artificial Sequence
<220> FEATURE:
<223> OTHER INFORMATION: Description of Artificial Sequence: Synthetic
                        oligonucleotide
<220> FEATURE:
<221> NAME/KEY: modified_base
<222> LOCATION: (15)..(18)
<223> OTHER INFORMATION: A mixture of trinucleotides encoding the amino
                        acids Ala, Asp, Glu, Phe, His, Ile, Lys, Leu,
                        Met, Asn, Gln, Arg, Ser, Thr, Val, Trp and Tyr
<220> FEATURE:
<221> NAME/KEY: modified_base
<222> LOCATION: (21)..(23)
<223> OTHER INFORMATION: A mixture of trinucleotides encoding the amino
                        acids Ala, Asp, Glu, Phe, His, Ile, Lys, Leu,
                        Met, Asn, Gln, Arg, Ser, Thr, Val, Trp and Tyr
<220> FEATURE:
<221> NAME/KEY: modified_base
<222> LOCATION: (24)..(26)
<223> OTHER INFORMATION: A mixture of trinucleotides encoding the amino
                        acids Ala, Asp, Glu, Phe, His, Ile, Lys, Leu,
                        Met, Asn, Gln, Arg, Ser, Thr, Val, Trp and Tyr
<220> FEATURE:
<221> NAME/KEY: modified_base
<222> LOCATION: (30)..(32)
<223> OTHER INFORMATION: A mixture of trinucleotides encoding the amino
                        acids Ala, Asp, Glu, Phe, His, Ile, Lys, Leu,
                        Met, Asn, Gln, Arg, Ser, Thr, Val, Trp and Tyr

<400> SEQUENCE: 38
ctgacgttaa cgctnnngac nnnnnnggtn nnactccgct gcacctggc                49

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
                        oligonucleotide
<220> FEATURE:
<221> NAME/KEY: modified_base
<222> LOCATION: (22)..(24)
<223> OTHER INFORMATION: A mixture of trinucleotides encoding the amino
                        acids Ala, Asp, Glu, Phe, His, Ile, Lys, Leu,
                        Met, Asn, Gln, Arg, Ser, Thr, Val, Trp and Tyr
<220> FEATURE:
<221> NAME/KEY: modified_base
<222> LOCATION: (25)..(27)
<223> OTHER INFORMATION: A mixture of trinucleotides encoding the amino
                        acids Ala, Asp, Glu, Phe, His, Ile, Lys, Leu,
                        Met, Asn, Gln, Arg, Ser, Thr, Val, Trp and Tyr

<400> SEQUENCE: 39
actccgctgc acctggctgc tnnnnnnggt cacctggaaa tcg                      43
```

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (15)
<223> OTHER INFORMATION: a, t or g

<400> SEQUENCE: 40
aacgtcagca ccgtncttca gcagaacttc aacgatttcc aggtgacc                48

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
agcagccagg tgcagcggag t                                             21

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
ttccgcggat cctaggaaga cctgacgtta acgct                              35

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
tttgggaagc ttctaaggtc tcacgtcagc accgt                              35

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
tttgggaagc ttctaaggtc tc                                            22

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
tttgggaagc ttctagaaga caacgtcagc accgt                35

<210> SEQ ID NO 46
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttccgcggat ccgacctggg taagaaactg ctggaagctg ctcgtgctgg tcaggacgac    60
gaag                                                                64

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aacgtcagca ccgttagcca tcaggatacg aacttcgtcg tcctgacc                 48

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttccgcggat ccgacctggg                                                20

<210> SEQ ID NO 49
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttccgcggat ccg                                                       13

<210> SEQ ID NO 50
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctgacgttaa cgctcaggac aaattcggta agaccgcttt cgacatctcc atcgacaacg    60
gtaacgagg                                                           69

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic -continued

<400> SEQUENCE: 51
ttgcaggatt tcagccaggt cctcgttacc gttgtc        36

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tttgggaagc ttctattgca ggatttcagc        30

<210> SEQ ID NO 53
<211> LENGTH: 460
<212> TYPE: PRT
<213> ORGANISM: Homo sapiens

<400> SEQUENCE: 53

Ser Leu Asp Ile Gln Ser Leu Asp Ile Gln Cys Glu Glu Leu Ser Asp
 1               5                  10                  15

Ala Arg Trp Ala Glu Leu Leu Pro Leu Leu Gln Gln Cys Gln Val Val
            20                  25                  30

Arg Leu Asp Asp Cys Gly Leu Thr Glu Ala Arg Cys Lys Asp Ile Ser
        35                  40                  45

Ser Ala Leu Arg Val Asn Pro Ala Leu Ala Glu Leu Asn Leu Arg Ser
    50                  55                  60

Asn Glu Leu Gly Asp Val Gly Val His Cys Val Leu Gln Gly Leu Gln
65                  70                  75                  80

Thr Pro Ser Cys Lys Ile Gln Lys Leu Ser Leu Gln Asn Cys Cys Leu
                85                  90                  95

Thr Gly Ala Gly Cys Gly Val Leu Ser Ser Thr Leu Arg Thr Leu Pro
            100                 105                 110

Thr Leu Gln Glu Leu His Leu Ser Asp Asn Leu Leu Gly Asp Ala Gly
        115                 120                 125

Leu Gln Leu Leu Cys Glu Gly Leu Leu Asp Pro Gln Cys Arg Leu Glu
    130                 135                 140

Lys Leu Gln Leu Glu Tyr Cys Ser Leu Ser Ala Ala Ser Cys Glu Pro
145                 150                 155                 160

Leu Ala Ser Val Leu Arg Ala Lys Pro Asp Phe Lys Glu Leu Thr Val
                165                 170                 175

Ser Asn Asn Asp Ile Asn Glu Ala Gly Val Arg Val Leu Cys Gln Gly
            180                 185                 190

Leu Lys Asp Ser Pro Cys Gln Leu Glu Ala Leu Lys Leu Glu Ser Cys
        195                 200                 205

Gly Val Thr Ser Asp Asn Cys Arg Asp Leu Cys Gly Ile Val Ala Ser
    210                 215                 220

Lys Ala Ser Leu Arg Glu Leu Ala Leu Gly Ser Asn Lys Leu Gly Asp
225                 230                 235                 240

Val Gly Met Ala Glu Leu Cys Pro Gly Leu Leu His Pro Ser Ser Arg
                245                 250                 255

Leu Arg Thr Leu Trp Ile Trp Glu Cys Gly Ile Thr Ala Lys Gly Cys
            260                 265                 270

Gly Asp Leu Cys Arg Val Leu Arg Ala Lys Glu Ser Leu Lys Glu Leu

```
                275                 280                 285
Ser Leu Ala Gly Asn Glu Leu Gly Asp Glu Gly Ala Arg Leu Leu Cys
            290                 295                 300

Glu Thr Leu Leu Glu Pro Gly Cys Gln Leu Glu Ser Leu Trp Val Lys
305                 310                 315                 320

Ser Cys Ser Phe Thr Ala Ala Cys Cys Ser His Phe Ser Ser Val Leu
            325                 330                 335

Ala Gln Asn Arg Phe Leu Leu Glu Leu Gln Ile Ser Asn Asn Arg Leu
            340                 345                 350

Glu Asp Ala Gly Val Arg Glu Leu Cys Gln Gly Leu Gly Gln Pro Gly
            355                 360                 365

Ser Val Leu Arg Val Leu Trp Leu Ala Asp Cys Asp Val Ser Asp Ser
            370                 375                 380

Ser Cys Ser Ser Leu Ala Ala Thr Leu Leu Ala Asn His Ser Leu Arg
385                 390                 395                 400

Glu Leu Asp Leu Ser Asn Asn Cys Leu Gly Asp Ala Gly Ile Leu Gln
            405                 410                 415

Leu Val Glu Ser Val Arg Gln Pro Gly Cys Leu Leu Glu Gln Leu Val
            420                 425                 430

Leu Tyr Asp Ile Tyr Trp Ser Glu Glu Met Glu Asp Arg Leu Gln Ala
            435                 440                 445

Leu Glu Lys Asp Lys Pro Ser Leu Arg Val Ile Ser
            450                 455                 460

<210> SEQ ID NO 54
<211> LENGTH: 225
<212> TYPE: PRT
<213> ORGANISM: Homo sapiens

<400> SEQUENCE: 54

Met Ser Leu Gln Val Val Arg Leu Asp Asp Cys Gly Leu Thr Glu Ala
1               5                   10                  15

Arg Cys Lys Asp Ile Ser Ser Ala Leu Arg Val Asn Pro Lys Ile Gln
            20                  25                  30

Lys Leu Ser Leu Gln Asn Cys Cys Leu Thr Gly Ala Gly Cys Gly Val
        35                  40                  45

Leu Ser Ser Thr Leu Arg Thr Leu Pro Arg Leu Glu Lys Leu Gln Leu
    50                  55                  60

Glu Tyr Cys Ser Leu Ser Ala Ala Ser Cys Glu Pro Leu Ala Ser Val
65                  70                  75                  80

Leu Arg Ala Lys Pro Gln Leu Glu Ala Leu Lys Leu Glu Ser Cys Gly
                85                  90                  95

Val Thr Ser Asp Asn Cys Arg Asp Leu Cys Gly Ile Val Ala Ser Lys
            100                 105                 110

Ala Arg Leu Arg Thr Leu Trp Ile Trp Glu Cys Gly Ile Thr Ala Lys
            115                 120                 125

Gly Cys Gly Asp Leu Cys Arg Val Leu Arg Ala Lys Glu Gln Leu Glu
        130                 135                 140

Ser Leu Trp Val Lys Ser Cys Ser Phe Thr Ala Ala Cys Cys Ser His
145                 150                 155                 160

Phe Ser Ser Val Leu Ala Gln Asn Arg Val Leu Arg Val Leu Trp Leu
                165                 170                 175

Ala Asp Cys Asp Val Ser Asp Ser Ser Cys Ser Ser Leu Ala Ala Thr
            180                 185                 190
```

```
Leu Leu Ala Asn His Leu Leu Glu Gln Leu Val Leu Tyr Asp Ile Tyr
        195                 200                 205

Trp Ser Glu Glu Met Glu Asp Arg Leu Gln Ala Leu Glu Lys Asp Lys
210                 215                 220

Pro
225

<210> SEQ ID NO 55
<211> LENGTH: 222
<212> TYPE: PRT
<213> ORGANISM: Sus scrofa

<400> SEQUENCE: 55

Glu Val Val Arg Leu Asp Asp Cys Gly Leu Thr Glu Glu His Cys Lys
1               5                   10                  15

Asp Ile Gly Ser Ala Leu Arg Ala Asn Pro Lys Ile Gln Lys Leu Ser
            20                  25                  30

Leu Gln Asn Cys Ser Leu Thr Glu Ala Gly Cys Gly Val Leu Pro Ser
        35                  40                  45

Thr Leu Arg Ser Leu Pro His Leu Glu Lys Leu Gln Leu Glu Tyr Cys
    50                  55                  60

Arg Leu Thr Ala Ala Ser Cys Glu Pro Leu Ala Ser Val Leu Arg Ala
65                  70                  75                  80

Thr Arg Gln Leu Glu Thr Leu Arg Leu Glu Asn Cys Gly Leu Thr Pro
                85                  90                  95

Ala Asn Cys Lys Asp Leu Cys Gly Ile Val Ala Ser Gln Ala Arg Leu
            100                 105                 110

Lys Thr Leu Trp Leu Trp Glu Cys Asp Ile Thr Ala Ser Gly Cys Arg
        115                 120                 125

Asp Leu Cys Arg Val Leu Gln Ala Lys Glu Gln Leu Glu Ser Leu Trp
    130                 135                 140

Val Lys Ser Cys Ser Leu Thr Ala Ala Cys Cys Gln His Val Ser Leu
145                 150                 155                 160

Met Leu Thr Gln Asn Lys Thr Leu Arg Val Leu Cys Leu Gly Asp Cys
                165                 170                 175

Glu Val Thr Asn Ser Gly Cys Ser Ser Leu Ala Ser Leu Leu Leu Ala
            180                 185                 190

Asn Arg Ala Leu Glu Gln Leu Val Leu Tyr Asp Thr Tyr Trp Thr Glu
        195                 200                 205

Glu Val Glu Asp Arg Leu Gln Ala Leu Glu Gly Ser Lys Pro
    210                 215                 220

<210> SEQ ID NO 56
<211> LENGTH: 221
<212> TYPE: PRT
<213> ORGANISM: Rattus sp.

<400> SEQUENCE: 56

Gln Val Val Arg Leu Asp Asp Cys Gly Leu Thr Glu Val Arg Cys Lys
1               5                   10                  15

Asp Ile Arg Ser Ala Ile Gln Ala Asn Pro Lys Ile Gln Lys Leu Ser
            20                  25                  30

Leu Gln Asn Cys Ser Leu Thr Glu Ala Gly Cys Gly Val Leu Pro Asp
        35                  40                  45

Val Leu Arg Ser Leu Ser Leu Glu Lys Leu Gln Leu Glu Tyr Cys Asn
    50                  55                  60
```

```
Leu Thr Ala Thr Ser Cys Glu Pro Leu Ala Ser Val Leu Arg Val Lys
 65                  70                  75                  80

Pro Gln Leu Glu Ser Leu Lys Leu Glu Asn Cys Gly Ile Thr Ser Ala
                 85                  90                  95

Asn Cys Lys Asp Leu Cys Asp Val Val Ala Ser Lys Ala Arg Leu Arg
            100                 105                 110

Thr Leu Trp Leu Trp Asp Cys Asp Val Thr Ala Glu Gly Cys Lys Asp
        115                 120                 125

Leu Cys Arg Val Leu Arg Ala Lys Gln Gln Leu Glu Ser Leu Trp Val
    130                 135                 140

Lys Thr Cys Ser Leu Thr Ala Ala Ser Cys Pro His Phe Cys Ser Val
145                 150                 155                 160

Leu Thr Lys Asn Ser Val Leu Arg Val Leu Trp Leu Gly Asp Cys Asp
                165                 170                 175

Val Thr Asp Ser Gly Cys Ser Ser Leu Ala Thr Val Leu Leu Ala Asn
            180                 185                 190

Arg Ile Leu Gln Gln Leu Val Leu Tyr Asp Ile Tyr Trp Thr Asp Glu
        195                 200                 205

Val Glu Asp Gln Leu Arg Ala Leu Glu Glu Arg Pro
    210                 215                 220

<210> SEQ ID NO 57
<211> LENGTH: 222
<212> TYPE: PRT
<213> ORGANISM: Mus musculus

<400> SEQUENCE: 57

Glu Val Val Arg Leu Asp Asp Cys Gly Leu Thr Glu Val Arg Cys Lys
  1               5                  10                  15

Asp Ile Ser Ser Ala Val Gln Ala Asn Pro Lys Ile Gln Lys Leu Ser
             20                  25                  30

Leu Gln Asn Cys Gly Leu Thr Glu Ala Gly Cys Gly Ile Leu Pro Gly
         35                  40                  45

Met Leu Arg Ser Leu Ser Arg Leu Glu Lys Leu Gln Leu Glu Tyr Cys
     50                  55                  60

Asn Leu Thr Ala Thr Ser Cys Glu Pro Leu Ala Ser Val Leu Arg Val
 65                  70                  75                  80

Lys Ala Gln Leu Glu Ser Leu Lys Leu Glu Asn Cys Gly Ile Thr Ala
                 85                  90                  95

Ala Asn Cys Lys Asp Leu Cys Asp Val Val Ala Ser Lys Ala Lys Leu
            100                 105                 110

Gly Thr Leu Trp Leu Trp Glu Cys Asp Ile Thr Ala Glu Gly Cys Lys
        115                 120                 125

Asp Leu Cys Arg Val Leu Arg Ala Asn Gln Gln Leu Glu Ser Leu Trp
    130                 135                 140

Ile Lys Thr Cys Ser Leu Thr Ala Ala Ser Cys Pro Tyr Phe Cys Ser
145                 150                 155                 160

Val Leu Thr Lys Ser Arg Val Leu Arg Glu Leu Trp Leu Gly Asp Cys
                165                 170                 175

Asp Val Thr Asn Ser Gly Cys Ser Ser Leu Ala Asn Val Leu Leu Ala
            180                 185                 190

Asn Arg Thr Leu Gln Gln Leu Val Leu Tyr Asp Ile Tyr Trp Thr Asn
        195                 200                 205

Glu Val Glu Gln Leu Arg Ala Leu Glu Glu Gly Arg Pro
    210                 215                 220
```

<210> SEQ ID NO 58
<211> LENGTH: 234
<212> TYPE: PRT
<213> ORGANISM: Homo sapiens

<400> SEQUENCE: 58

Asp Ile Gln Ser Leu Asp Ile Gln Cys Glu Glu Leu Ser Asp Ala Arg
1               5                   10                  15

Trp Ala Glu Leu Leu Pro Leu Leu Gln Gln Cys Ala Leu Ala Glu Leu
            20                  25                  30

Asn Leu Arg Ser Asn Glu Leu Gly Asp Val Gly Val His Cys Val Leu
        35                  40                  45

Gln Gly Leu Gln Thr Pro Ser Cys Thr Leu Gln Glu Leu His Leu Ser
    50                  55                  60

Asp Asn Leu Leu Gly Asp Ala Leu Gln Leu Leu Cys Glu Gly Leu Leu
65                  70                  75                  80

Asp Pro Gln Cys Asp Phe Lys Glu Leu Thr Val Ser Asn Asn Asp Ile
                85                  90                  95

Asn Glu Ala Gly Val Arg Val Leu Cys Gln Gly Leu Lys Asp Ser Pro
            100                 105                 110

Cys Ser Leu Arg Glu Leu Ala Leu Gly Ser Asn Lys Leu Gly Asp Val
        115                 120                 125

Gly Met Ala Glu Leu Cys Pro Gly Leu His Pro Ser Ser Ser Leu Lys
    130                 135                 140

Glu Leu Ser Leu Ala Gly Asn Glu Leu Gly Asp Glu Gly Ala Arg Leu
145                 150                 155                 160

Leu Cys Glu Thr Leu Leu Glu Pro Gly Cys Phe Leu Glu Leu Gln
                165                 170                 175

Ile Ser Asn Asn Arg Leu Glu Asp Ala Gly Val Arg Glu Leu Cys Gln
            180                 185                 190

Gly Leu Gly Gln Pro Gly Ser Ser Leu Arg Glu Leu Asp Leu Ser Asn
        195                 200                 205

Asn Cys Leu Gly Asp Ala Gly Ile Leu Gln Leu Val Glu Ser Val Arg
    210                 215                 220

Gln Pro Gly Cys Ser Leu Arg Val Ile Ser
225                 230

<210> SEQ ID NO 59
<211> LENGTH: 234
<212> TYPE: PRT
<213> ORGANISM: Sus scrofa

<400> SEQUENCE: 59

Met Asn Leu Asp Ile His Cys Glu Gln Leu Ser Asp Ala Arg Trp Thr
1               5                   10                  15

Glu Leu Leu Pro Leu Leu Gln Gln Tyr Ser Leu Thr Glu Leu Cys Leu
            20                  25                  30

Arg Thr Asn Glu Leu Gly Asp Ala Gly Val His Leu Val Leu Gln Gly
        35                  40                  45

Leu Gln Ser Pro Thr Cys Thr Leu Arg Glu Leu His Leu Ser Asp Asn
    50                  55                  60

Pro Leu Gly Asp Ala Gly Leu Arg Leu Leu Cys Glu Gly Leu Leu Asp
65                  70                  75                  80

Pro Gln Cys Ala Leu Lys Glu Leu Thr Val Ser Asn Asn Asp Ile Gly
                85                  90                  95

```
Glu Ala Gly Ala Arg Val Leu Gly Gln Gly Leu Ala Asp Ser Ala Cys
                100                 105                 110

Ser Leu Arg Glu Leu Asp Leu Gly Ser Asn Gly Leu Gly Asp Ala Gly
            115                 120                 125

Ile Ala Glu Leu Cys Pro Gly Leu Leu Ser Pro Ala Ser Thr Leu Lys
        130                 135                 140

Glu Leu Ser Leu Ala Gly Asn Lys Leu Gly Asp Glu Gly Ala Arg Leu
145                 150                 155                 160

Leu Cys Glu Ser Leu Leu Gln Pro Gly Cys His Leu Leu Glu Leu Gln
                165                 170                 175

Leu Ser Ser Asn Lys Leu Gly Asp Ser Gly Ile Gln Glu Leu Cys Gln
            180                 185                 190

Ala Leu Ser Gln Pro Gly Thr Ser Leu Arg Glu Leu Asp Leu Ser Asn
        195                 200                 205

Asn Cys Val Gly Asp Pro Gly Val Leu Gln Leu Leu Gly Ser Leu Glu
    210                 215                 220

Gln Pro Gly Cys Gly Leu Arg Val Ile Ser
225                 230

<210> SEQ ID NO 60
<211> LENGTH: 234
<212> TYPE: PRT
<213> ORGANISM: Rattus sp.

<400> SEQUENCE: 60

Met Ser Leu Asp Ile Gln Cys Glu Gln Leu Ser Asp Ala Arg Trp Thr
  1               5                  10                  15

Glu Leu Leu Pro Leu Ile Gln Gln Tyr Ala Leu Thr Glu Leu Ser Leu
             20                  25                  30

Arg Thr Asn Glu Leu Gly Asp Ala Gly Val Gly Leu Val Leu Gln Gly
         35                  40                  45

Leu Gln Asn Pro Thr Cys Thr Leu Arg Glu Leu His Leu Asn Asp Asn
 50                  55                  60

Pro Leu Gly Asp Glu Gly Leu Lys Leu Leu Cys Glu Gly Leu Arg Asp
 65                  70                  75                  80

Pro Gln Cys Asp Phe Lys Glu Leu Val Leu Ser Asn Asn Asp Phe His
                 85                  90                  95

Glu Ala Gly Ile His Thr Leu Cys Gln Gly Leu Lys Asp Ser Ala Cys
                100                 105                 110

Ser Leu Gln Glu Leu Asp Leu Gly Ser Asn Lys Leu Gly Asn Thr Gly
            115                 120                 125

Ile Ala Ala Leu Cys Ser Gly Leu Leu Pro Ser Cys Ser Leu Lys
        130                 135                 140

Glu Leu Ser Leu Ala Gly Asn Glu Leu Lys Asp Glu Gly Ala Gln Leu
145                 150                 155                 160

Leu Cys Glu Ser Leu Leu Glu Pro Gly Cys Ser Leu Phe Glu Leu Gln
                165                 170                 175

Met Ser Ser Asn Pro Leu Gly Asp Ser Gly Val Val Glu Leu Cys Lys
            180                 185                 190

Ala Leu Gly Tyr Pro Asp Thr Ser Leu Arg Glu Leu Asp Leu Ser Asn
        195                 200                 205

Asn Cys Met Gly Asp Asn Gly Val Leu Gln Leu Leu Glu Ser Leu Lys
    210                 215                 220

Gln Pro Ser Cys Ser Leu Arg Ile Ile Ser
225                 230
```

```
                        225                 230

<210> SEQ ID NO 61
<211> LENGTH: 233
<212> TYPE: PRT
<213> ORGANISM: Mus musculus
<220> FEATURE:
<221> NAME/KEY: MOD_RES
<222> LOCATION: (168)
<223> OTHER INFORMATION: Variable amino acid

<400> SEQUENCE: 61

Met Ser Leu Asp Ile Gln Cys Glu Gln Leu Gly Asp Ala Arg Trp Thr
 1               5                  10                  15

Glu Leu Leu Pro Leu Ile Gln Gln Tyr Ala Leu Thr Glu Leu Ser Leu
            20                  25                  30

Arg Thr Asn Glu Leu Gly Asp Gly Gly Ala Gly Leu Val Leu Gln Gly
        35                  40                  45

Leu Gln Asn Pro Thr Cys Thr Leu Arg Glu Leu His Leu Asn Asp Asn
    50                  55                  60

Pro Met Gly Asp Ala Gly Leu Lys Leu Leu Cys Glu Gly Leu Gln Asp
65                  70                  75                  80

Pro Gln Cys Asp Phe Lys Glu Leu Val Ser Asn Asn Asp Leu His Glu
                85                  90                  95

Pro Gly Val Arg Ile Leu Cys Gln Gly Leu Lys Asp Ser Ala Cys Ser
            100                 105                 110

Leu Gln Glu Leu Asp Leu Ser Ser Asn Lys Leu Gly Asn Ala Gly Ile
        115                 120                 125

Ala Ala Leu Cys Pro Gly Leu Leu Leu Pro Ser Cys Ser Leu Lys Glu
    130                 135                 140

Leu Ser Leu Ala Ser Asn Glu Leu Lys Asp Glu Gly Ala Arg Leu Leu
145                 150                 155                 160

Cys Glu Ser Leu Leu Glu Pro Xaa Cys Ser Leu Leu Glu Leu Gln Met
                165                 170                 175

Ser Ser Asn Pro Leu Gly Asp Glu Gly Val Gln Glu Leu Cys Lys Ala
            180                 185                 190

Leu Ser Gln Pro Asp Thr Ser Leu Arg Glu Leu Asp Leu Ser Asn Asn
        195                 200                 205

Cys Met Gly Gly Pro Gly Val Leu Gln Leu Leu Glu Ser Leu Lys Gln
    210                 215                 220

Pro Ser Cys Ser Leu Arg Ile Ile Ser
225                 230

<210> SEQ ID NO 62
<211> LENGTH: 460
<212> TYPE: DNA
<213> ORGANISM: Artificial Sequence
<220> FEATURE:
<223> OTHER INFORMATION: Description of Artificial Sequence: Synthetic
      NcoI-HindIII insert
<220> FEATURE:
<221> NAME/KEY: CDS
<222> LOCATION: (4)..(450)
<220> FEATURE:
<221> NAME/KEY: modified_base
<222> LOCATION: (142)..(144)
<223> OTHER INFORMATION: a, c, g or t
<220> FEATURE:
<221> NAME/KEY: modified_base
<222> LOCATION: (148)..(150)
<223> OTHER INFORMATION: a, c, g or t
<220> FEATURE:
```

<221> NAME/KEY: modified_base
<222> LOCATION: (154)..(162)
<223> OTHER INFORMATION: a, c, g or t
<220> FEATURE:
<221> NAME/KEY: modified_base
<222> LOCATION: (181)
<223> OTHER INFORMATION: a, c, g or t
<220> FEATURE:
<221> NAME/KEY: modified_base
<222> LOCATION: (232)..(234)
<223> OTHER INFORMATION: a, c, g or t
<220> FEATURE:
<221> NAME/KEY: modified_base
<222> LOCATION: (241)..(243)
<223> OTHER INFORMATION: a, c, g or t

<400> SEQUENCE: 62

```
tcc atg gac tac aag gat cat cac cat cac cat cac gga tcc ctg gac      48
    Met Asp Tyr Lys Asp His His His His His His Gly Ser Leu Asp
    1               5                   10                  15 atc cag agc ctg gac atc cag tgt gag gag ctg agc gac gct aga tgg      96
Ile Gln Ser Leu Asp Ile Gln Cys Glu Glu Leu Ser Asp Ala Arg Trp
            20                  25                  30 gcc gag ctc ctc cct ctg ctc cag cag ccc tac gcg cgc ctg gag nnn     144
Ala Glu Leu Leu Pro Leu Leu Gln Gln Pro Tyr Ala Arg Leu Glu Xaa
        35                  40                  45 ctg nnn ctg nnn nnn nnn gac ctc acc gag gcc ggc ntg aag gac ctg     192
Leu Xaa Leu Xaa Xaa Xaa Asp Leu Thr Glu Ala Gly Xaa Lys Asp Leu
    50                  55                  60 gcc agc gtg ctc cgc tcc aac ccg agc ctg cgg gag ctg nnn ctg agc     240
Ala Ser Val Leu Arg Ser Asn Pro Ser Leu Arg Glu Leu Xaa Leu Ser
65                  70                  75                  80 nnn aac aag ctc ggc gat gca ggc gtg cgg ctg ctc ttg cag ggg ctg     288
Xaa Asn Lys Leu Gly Asp Ala Gly Val Arg Leu Leu Leu Gln Gly Leu
                85                  90                  95 ctg gac ccc ggc acg cgt ctc gag cag ctg gtc ctg tac gac att tac     336
Leu Asp Pro Gly Thr Arg Leu Glu Gln Leu Val Leu Tyr Asp Ile Tyr
            100                 105                 110 tgg tct gag gag atg gag gac cgg ctg cag gcc ctg gag aag gac aag     384
Trp Ser Glu Glu Met Glu Asp Arg Leu Gln Ala Leu Glu Lys Asp Lys
        115                 120                 125 cca tcc ctg agg gtc atc tcc ggt tcc gct ggc tcc gct gct ggt tct     432
Pro Ser Leu Arg Val Ile Ser Gly Ser Ala Gly Ser Ala Ala Gly Ser
    130                 135                 140 ggc gag gct agc gaa ttc tgataagctt                                   460
Gly Glu Ala Ser Glu Phe
    145
```

<210> SEQ ID NO 63
<211> LENGTH: 149
<212> TYPE: PRT
<213> ORGANISM: Artificial Sequence
<220> FEATURE:
<223> OTHER INFORMATION: Description of Artificial Sequence: Translated amino acid sequence of the synthetic NcoI-HindIII insert
<220> FEATURE:
<221> NAME/KEY: MOD_RES
<222> LOCATION: (47)
<223> OTHER INFORMATION: Variable amino acid
<220> FEATURE:
<221> NAME/KEY: MOD_RES
<222> LOCATION: (49)
<223> OTHER INFORMATION: Variable amino acid
<220> FEATURE:
<221> NAME/KEY: MOD_RES
<222> LOCATION: (51)..(53)
<223> OTHER INFORMATION: Variable amino acid

```
<220> FEATURE:
<221> NAME/KEY: MOD_RES
<222> LOCATION: (60)
<223> OTHER INFORMATION: Variable amino acid
<220> FEATURE:
<221> NAME/KEY: MOD_RES
<222> LOCATION: (77)
<223> OTHER INFORMATION: Variable amino acid
<220> FEATURE:
<221> NAME/KEY: MOD_RES
<222> LOCATION: (80)
<223> OTHER INFORMATION: Variable amino acid

<400> SEQUENCE: 63

Met Asp Tyr Lys Asp His His His His His Gly Ser Leu Asp Ile
 1               5                  10                  15

Gln Ser Leu Asp Ile Gln Cys Glu Glu Leu Ser Asp Ala Arg Trp Ala
            20                  25                  30

Glu Leu Leu Pro Leu Leu Gln Gln Pro Tyr Ala Arg Leu Glu Xaa Leu
        35                  40                  45

Xaa Leu Xaa Xaa Xaa Asp Leu Thr Glu Ala Gly Xaa Lys Asp Leu Ala
    50                  55                  60

Ser Val Leu Arg Ser Asn Pro Ser Leu Arg Glu Leu Xaa Leu Ser Xaa
 65                  70                  75                  80

Asn Lys Leu Gly Asp Ala Gly Val Arg Leu Leu Leu Gln Gly Leu Leu
                85                  90                  95

Asp Pro Gly Thr Arg Leu Glu Gln Leu Val Leu Tyr Asp Ile Tyr Trp
            100                 105                 110

Ser Glu Glu Met Glu Asp Arg Leu Gln Ala Leu Glu Lys Asp Lys Pro
        115                 120                 125

Ser Leu Arg Val Ile Ser Gly Ser Ala Gly Ser Ala Ala Gly Ser Gly
    130                 135                 140

Glu Ala Ser Glu Phe
145

<210> SEQ ID NO 64
<211> LENGTH: 927
<212> TYPE: DNA
<213> ORGANISM: Artificial Sequence
<220> FEATURE:
<223> OTHER INFORMATION: Description of Artificial Sequence: Synthetic
      NcoI-HindIII insert
<220> FEATURE:
<221> NAME/KEY: CDS
<222> LOCATION: (3)..(917)

<400> SEQUENCE: 64 cc atg gac tac aag gat cat cac cat cac cat cac gga tcc ctg gac       47
   Met Asp Tyr Lys Asp His His His His His His Gly Ser Leu Asp
    1               5                  10                  15 atc cag agc ctg gac atc cag tgt gag gag ctg agc gac gct aga tgg      95
Ile Gln Ser Leu Asp Ile Gln Cys Glu Glu Leu Ser Asp Ala Arg Trp
            20                  25                  30 gcc gag ctc ctc cct ctg ctc cag cag ccc tac gcg cgc ctg gag aag     143
Ala Glu Leu Leu Pro Leu Leu Gln Gln Pro Tyr Ala Arg Leu Glu Lys
        35                  40                  45 ctg gat ctg aat gat act gac ctc acc gag gcc ggc gtg aag gac ctg     191
Leu Asp Leu Asn Asp Thr Asp Leu Thr Glu Ala Gly Val Lys Asp Leu
    50                  55                  60 gcc agc gtg ctc cgc tcc aac ccg agc ctg cgg gag ctg tct ctg agc     239
Ala Ser Val Leu Arg Ser Asn Pro Ser Leu Arg Glu Leu Ser Leu Ser
 65                  70                  75
```

```
act aac aag ctc ggc gat gca ggc gtg cgg ctg ctc ttg cag ggg ctg      287
Thr Asn Lys Leu Gly Asp Ala Gly Val Arg Leu Leu Leu Gln Gly Leu
 80              85                  90                  95 ctg gac ccc ggc acg cgc ctg gag aag ctg tat ctg gag cat aat gac      335
Leu Asp Pro Gly Thr Arg Leu Glu Lys Leu Tyr Leu Glu His Asn Asp
            100                 105                 110 ctc acc gag gcc ggc ctg aag gac ctg gcc agc gtg ctc cgc tcc aac      383
Leu Thr Glu Ala Gly Leu Lys Asp Leu Ala Ser Val Leu Arg Ser Asn
        115                 120                 125 ccg agc ctg cgg gag ctg aat ctg agc gat aac aag ctc ggc gat gca      431
Pro Ser Leu Arg Glu Leu Asn Leu Ser Asp Asn Lys Leu Gly Asp Ala
    130                 135                 140 ggc gtg cgg ctg ctc ttg cag ggg ctg ctg gac ccc ggc acg cgc ctg      479
Gly Val Arg Leu Leu Leu Gln Gly Leu Leu Asp Pro Gly Thr Arg Leu
145                 150                 155 gag gag ctg cag ctg cgt aat act gac ctc acc gag gcc ggc gtg gag      527
Glu Glu Leu Gln Leu Arg Asn Thr Asp Leu Thr Glu Ala Gly Val Glu
160                 165                 170                 175 gac ctg gcc agc gtg ctc cgc tcc aac ccg agc ctg cgg gag ctg tct      575
Asp Leu Ala Ser Val Leu Arg Ser Asn Pro Ser Leu Arg Glu Leu Ser
            180                 185                 190 ctg agc aat aac aag ctc ggc gat gca ggc gtg cgg ctg ctc ttg cag      623
Leu Ser Asn Asn Lys Leu Gly Asp Ala Gly Val Arg Leu Leu Leu Gln
        195                 200                 205 ggg ctg ctg gac ccc ggc acg cgc ctg gag aag ctg tat ctg cgt aat      671
Gly Leu Leu Asp Pro Gly Thr Arg Leu Glu Lys Leu Tyr Leu Arg Asn
    210                 215                 220 act gac ctc acc gag gcc ggc atg aag gac ctg gcc agc gtg ctc cgc      719
Thr Asp Leu Thr Glu Ala Gly Met Lys Asp Leu Ala Ser Val Leu Arg
225                 230                 235 tcc aac ccg agc ctg cgg gag ctg tct ctg agc act aac aag ctc ggc      767
Ser Asn Pro Ser Leu Arg Glu Leu Ser Leu Ser Thr Asn Lys Leu Gly
240                 245                 250                 255 gat gca ggc gtg cgg ctg ctc ttg cag ggg ctg ctg gac ctc ggc acg      815
Asp Ala Gly Val Arg Leu Leu Leu Gln Gly Leu Leu Asp Leu Gly Thr
            260                 265                 270 cgc ctc gag cag ctg gtc ctg tac gac att tac tgg tct gag gag atg      863
Arg Leu Glu Gln Leu Val Leu Tyr Asp Ile Tyr Trp Ser Glu Glu Met
        275                 280                 285 gag gac cgg ctg cag gcc ctg gag aag gac aag cca tcc ctg agg gtc      911
Glu Asp Arg Leu Gln Ala Leu Glu Lys Asp Lys Pro Ser Leu Arg Val
    290                 295                 300 atc tcc tgataagctt                                                    927
Ile Ser
    305
```

<210> SEQ ID NO 65
<211> LENGTH: 305
<212> TYPE: PRT
<213> ORGANISM: Artificial Sequence
<220> FEATURE:
<223> OTHER INFORMATION: Description of Artificial Sequence: Translated
      amino acid sequence of the synthetic NcoI-
      HindIII insert

<400> SEQUENCE: 65

```
Met Asp Tyr Lys Asp His His His His His Gly Ser Leu Asp Ile
 1               5                  10                  15

Gln Ser Leu Asp Ile Gln Cys Glu Glu Leu Ser Asp Ala Arg Trp Ala
            20                  25                  30

Glu Leu Leu Pro Leu Leu Gln Gln Pro Tyr Ala Arg Leu Glu Lys Leu
```

```
                35                  40                  45
Asp Leu Asn Asp Thr Asp Leu Thr Glu Ala Gly Val Lys Asp Leu Ala
             50                  55                  60

Ser Val Leu Arg Ser Asn Pro Ser Leu Arg Glu Leu Ser Leu Ser Thr
 65                  70                  75                  80

Asn Lys Leu Gly Asp Ala Gly Val Arg Leu Leu Gln Gly Leu Leu
                 85                  90                  95

Asp Pro Gly Thr Arg Leu Glu Lys Leu Tyr Leu Glu His Asn Asp Leu
                100                 105                 110

Thr Glu Ala Gly Leu Lys Asp Leu Ala Ser Val Leu Arg Ser Asn Pro
                115                 120                 125

Ser Leu Arg Glu Leu Asn Leu Ser Asp Asn Lys Leu Gly Asp Ala Gly
            130                 135                 140

Val Arg Leu Leu Leu Gln Gly Leu Leu Asp Pro Gly Thr Arg Leu Glu
145                 150                 155                 160

Glu Leu Gln Leu Arg Asn Thr Asp Leu Thr Glu Ala Gly Val Glu Asp
                165                 170                 175

Leu Ala Ser Val Leu Arg Ser Asn Pro Ser Leu Arg Glu Leu Ser Leu
            180                 185                 190

Ser Asn Asn Lys Leu Gly Asp Ala Gly Val Arg Leu Leu Leu Gln Gly
            195                 200                 205

Leu Leu Asp Pro Gly Thr Arg Leu Glu Lys Leu Tyr Leu Arg Asn Thr
            210                 215                 220

Asp Leu Thr Glu Ala Gly Met Lys Asp Leu Ala Ser Val Leu Arg Ser
225                 230                 235                 240

Asn Pro Ser Leu Arg Glu Leu Ser Leu Ser Thr Asn Lys Leu Gly Asp
                245                 250                 255

Ala Gly Val Arg Leu Leu Leu Gln Gly Leu Leu Asp Leu Gly Thr Arg
                260                 265                 270

Leu Glu Gln Leu Val Leu Tyr Asp Ile Tyr Trp Ser Glu Glu Met Glu
            275                 280                 285

Asp Arg Leu Gln Ala Leu Glu Lys Asp Lys Pro Ser Leu Arg Val Ile
    290                 295                 300

Ser
305

<210> SEQ ID NO 66
<211> LENGTH: 12
<212> TYPE: DNA
<213> ORGANISM: Artificial Sequence
<220> FEATURE:
<223> OTHER INFORMATION: Description of Artificial Sequence: Synthetic
                        construct; type IIs restriction enzyme
<220> FEATURE:
<221> NAME/KEY: modified_base
<222> LOCATION: (7)..(12)
<223> OTHER INFORMATION: a, c, g or t

<400> SEQUENCE: 66
gaagacnnnn nn                                                          12

<210> SEQ ID NO 67
<211> LENGTH: 11
<212> TYPE: DNA
<213> ORGANISM: Artificial Sequence
<220> FEATURE:
<223> OTHER INFORMATION: Description of Artificial Sequence: Synthetic
                        construct; type IIs restriction enzyme
<220> FEATURE:
```

```
<221> NAME/KEY: modified_base
<222> LOCATION: (7)..(11)
<223> OTHER INFORMATION: a, c, g or t

<400> SEQUENCE: 67
ggtctcnnnn n                                                            11

<210> SEQ ID NO 68
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (3)
<223> OTHER INFORMATION: Variable amino acid
<220> FEATURE:
<221> NAME/KEY: MOD_RES
<222> LOCATION: (11)..(12)
<223> OTHER INFORMATION: Variable amino acid
<220> FEATURE:
<221> NAME/KEY: MOD_RES
<222> LOCATION: (15)
<223> OTHER INFORMATION: Variable amino acid
<220> FEATURE:
<221> NAME/KEY: MOD_RES
<222> LOCATION: (23)..(24)
<223> OTHER INFORMATION: Variable amino acid
<220> FEATURE:
<221> NAME/KEY: MOD_RES
<222> LOCATION: (30)
<223> OTHER INFORMATION: Variable amino acid

<400> SEQUENCE: 68

Xaa Gly Xaa Thr Pro Leu His Leu Ala Ala Xaa Xaa Gly His Xaa Glu
 1               5                  10                  15

Val Val Lys Leu Leu Leu Xaa Xaa Gly Ala Asp Val Asn Xaa
            20                  25                  30

<210> SEQ ID NO 69
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (13)..(14)
<223> OTHER INFORMATION: Variable amino acid
<220> FEATURE:
<221> NAME/KEY: MOD_RES
<222> LOCATION: (33)
<223> OTHER INFORMATION: Variable amino acid

<400> SEQUENCE: 69

Asp Xaa Xaa Gly Xaa Thr Pro Leu His Leu Ala Ala Xaa Xaa Gly His
 1               5                  10                  15
```

Leu Glu Val Val Lys Leu Leu Leu Glu Asn Gly Ala Asp Val Asn Ala
            20                  25                  30

Xaa

<210> SEQ ID NO 70
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 70

Val Lys Leu Leu Leu Glu Ala Gly Ala Asp Val Asn Ala Arg Asp Ser
 1               5                  10                  15

Asp Gly Asn Thr Pro Leu His Leu Ala Ala Glu Asn Gly Gln Leu Glu
            20                  25                  30

Val

<210> SEQ ID NO 71
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide construct
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (13)..(14)
<223> OTHER INFORMATION: Variable amino acid
<220> FEATURE:
<221> NAME/KEY: MOD_RES
<222> LOCATION: (33)
<223> OTHER INFORMATION: Variable amino acid

<400> SEQUENCE: 71

Asp Xaa Xaa Gly Xaa Thr Pro Leu His Leu Ala Ala Xaa Xaa Gly His
 1               5                  10                  15

Leu Glu Val Val Glu Val Leu Leu Lys His Gly Ala Asp Val Asn Ala
            20                  25                  30

Xaa

<210> SEQ ID NO 72
<211> LENGTH: 33
<212> TYPE: PRT
<213> ORGANISM: Artificial Sequence
<220> FEATURE:
<223> OTHER INFORMATION: Description of Artificial Sequence: Synthetic
      ankyrin repeat motif sequence
<220> FEATURE:
<221> NAME/KEY: MOD_RES
<222> LOCATION: (4)
<223> OTHER INFORMATION: May be Ala, Asp, Glu, Phe, His, Ile, Lys, Leu,
      Met, Asn, Gln, Arg, Ser, Thr, Val, Trp or Tyr
<220> FEATURE:
<221> NAME/KEY: MOD_RES
<222> LOCATION: (6)..(7)
<223> OTHER INFORMATION: May be Ala, Asp, Glu, Phe, His, Ile, Lys, Leu,
      Met, Asn, Gln, Arg, Ser, Thr, Val, Trp or Tyr
<220> FEATURE:
<221> NAME/KEY: MOD_RES

```
<222> LOCATION: (9)
<223> OTHER INFORMATION: May be Ala, Asp, Glu, Phe, His, Ile, Lys, Leu,
                        Met, Asn, Gln, Arg, Ser, Thr, Val, Trp or Tyr
<220> FEATURE:
<221> NAME/KEY: MOD_RES
<222> LOCATION: (17)..(18)
<223> OTHER INFORMATION: May be Ala, Asp, Glu, Phe, His, Ile, Lys, Leu,
                        Met, Asn, Gln, Arg, Ser, Thr, Val, Trp or Tyr
<220> FEATURE:
<221> NAME/KEY: MOD_RES
<222> LOCATION: (30)
<223> OTHER INFORMATION: May be Asn, Tyr or His

<400> SEQUENCE: 72

Val Asn Ala Xaa Asp Xaa Xaa Gly Xaa Thr Pro Leu His Leu Ala Ala
  1               5                  10                  15

Xaa Xaa Gly His Leu Glu Ile Val Glu Val Leu Leu Lys Xaa Gly Ala
             20                  25                  30

Asp

<210> SEQ ID NO 73
<211> LENGTH: 166
<212> TYPE: PRT
<213> ORGANISM: Artificial Sequence
<220> FEATURE:
<223> OTHER INFORMATION: Description of Artificial Sequence: Synthetic
                        E3-5 amino acid sequence

<400> SEQUENCE: 73

Met Arg Gly Ser His His His His His His Gly Ser Asp Leu Gly Lys
  1               5                  10                  15

Lys Leu Leu Glu Ala Ala Arg Ala Gly Gln Asp Asp Glu Val Arg Ile
             20                  25                  30

Leu Met Ala Asn Gly Ala Asp Val Asn Ala Thr Asp Asn Asp Gly Tyr
         35                  40                  45

Thr Pro Leu His Leu Ala Ala Ser Asn Gly His Leu Glu Ile Val Glu
     50                  55                  60

Val Leu Leu Lys Asn Gly Ala Asp Val Asn Ala Ser Asp Leu Thr Gly
 65                  70                  75                  80

Ile Thr Pro Leu His Leu Ala Ala Thr Gly His Leu Glu Ile Val
                 85                  90                  95

Glu Val Leu Leu Lys His Gly Ala Asp Val Asn Ala Tyr Asp Asn Asp
            100                 105                 110

Gly His Thr Pro Leu His Leu Ala Ala Lys Tyr Gly His Leu Glu Ile
        115                 120                 125

Val Glu Val Leu Leu Lys His Gly Ala Asp Val Asn Ala Gln Asp Lys
    130                 135                 140

Phe Gly Lys Thr Ala Phe Asp Ile Ser Ile Asp Asn Gly Asn Glu Asp
145                 150                 155                 160

Leu Ala Glu Ile Leu Gln
                165

<210> SEQ ID NO 74
<211> LENGTH: 153
<212> TYPE: PRT
<213> ORGANISM: Mus musculus

<400> SEQUENCE: 74

Asp Leu Gly Lys Lys Leu Leu Glu Ala Ala Arg Ala Gly Gln Asp Asp
  1               5                  10                  15

Glu Val Arg Ile Leu Met Ala Asn Gly Ala Pro Phe Thr Thr Asp Trp
```

```
                20                  25                  30
Leu Gly Thr Ser Pro Leu His Leu Ala Ala Gln Tyr Gly His Phe Ser
            35                  40                  45

Thr Thr Glu Val Leu Leu Arg Ala Gly Val Ser Arg Asp Ala Arg Thr
        50                  55                  60

Lys Val Asp Arg Thr Pro Leu His Met Ala Ala Ser Glu Gly His Ala
 65                  70                  75                  80

Asn Ile Val Glu Val Leu Leu Lys His Gly Ala Asp Val Asn Ala Lys
                85                  90                  95

Asp Met Leu Lys Met Thr Ala Leu His Trp Ala Thr Glu His Asn His
            100                 105                 110

Gln Glu Val Val Glu Leu Leu Ile Lys Tyr Gly Ala Asp Val His Thr
        115                 120                 125

Gln Ser Lys Phe Cys Lys Thr Ala Phe Asp Ile Ser Ile Asp Asn Gly
    130                 135                 140

Asn Glu Asp Leu Ala Glu Ile Leu Gln
145                 150

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 75

Pro Tyr Ala Arg
  1

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His tag

<400> SEQUENCE: 76

His His His His His His
  1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      flag-tag sequence

<400> SEQUENCE: 77

Met Asp Tyr Lys Asp
  1               5
```